(12) United States Patent
Puig Duran et al.

(10) Patent No.: US 10,005,771 B2
(45) Date of Patent: Jun. 26, 2018

(54) BICYCLIC DERIVATIVES HAVING β2 ADRENERGIC AGONIST AND M3 MUSCARINIC ANTAGONIST ACTIVITIES

(71) Applicant: Almirall, S.A., Barcelona (ES)

(72) Inventors: Carlos Puig Duran, Barcelona (ES); Jose Aiguade Bosch, Barcelona (ES); Silvia Gual Roig, Barcelona (ES); Maria Prat Quiñones, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days. days.

(21) Appl. No.: 15/514,294

(22) PCT Filed: Sep. 25, 2015

(86) PCT No.: PCT/EP2015/072158
§ 371 (c)(1),
(2) Date: Mar. 24, 2017

(87) PCT Pub. No.: WO2016/046390
PCT Pub. Date: Mar. 31, 2016

(65) Prior Publication Data
US 2017/0275277 A1 Sep. 28, 2017

(30) Foreign Application Priority Data
Sep. 26, 2014 (EP) .................................... 14382372

(51) Int. Cl.
*C07D 453/02* (2006.01)
*A61K 31/439* (2006.01)

(52) U.S. Cl.
CPC ................................ *C07D 453/02* (2013.01)

(58) Field of Classification Search
CPC ........................... C07D 453/02; A61K 31/439
USPC ................................................. 546/152, 133
See application file for complete search history.

(56) References Cited

U.S. PATENT DOCUMENTS

| | | | |
|---|---|---|---|
| 2,404,588 A * | 7/1946 | Martin | C07C 61/39 560/102 |
| 4,556,653 A | 12/1985 | Giani et al. | |
| 5,397,800 A | 3/1995 | Alker et al. | |
| 6,673,908 B1 | 1/2004 | Stanton, Jr. | |
| 9,072,734 B2 | 7/2015 | Mitsuyama et al. | |
| 9,233,108 B2 | 1/2016 | Aiguade Bosch et al. | |
| 9,315,463 B2 | 4/2016 | Prat Quinones et al. | |
| 9,518,050 B2 | 12/2016 | Sole Feu et al. | |
| 9,549,934 B2 | 1/2017 | Aiguade Bosch et al. | |
| 9,562,039 B2 | 2/2017 | Julia Jane et al. | |
| 9,579,316 B2 | 2/2017 | Julia Jane et al. | |
| 9,643,961 B2 | 5/2017 | Prat Quinones et al. | |
| 9,757,383 B2 | 9/2017 | Aiguade Bosch et al. | |
| 2012/0046467 A1 | 2/2012 | Mitsuyama et al. | |
| 2013/0053359 A1 | 2/2013 | Prat Quinones et al. | |
| 2013/0281415 A9 | 10/2013 | Prat Quinones et al. | |
| 2014/0303127 A1 | 10/2014 | Bosch et al. | |
| 2014/0378421 A1 | 12/2014 | Bosch et al. | |
| 2015/0329535 A1 | 11/2015 | Sole Feu et al. | |
| 2016/0009698 A1 | 1/2016 | Julia Jane et al. | |
| 2016/0015704 A1 | 1/2016 | Aparici Virgili et al. | |
| 2016/0143915 A1 | 5/2016 | Aiguade Bosch et al. | |
| 2016/0166566 A1 | 6/2016 | Julia Jane et al. | |
| 2016/0175295 A1 | 6/2016 | Aparici Virgili et al. | |
| 2016/0200718 A1 | 7/2016 | Aiguade Bosch et al. | |
| 2016/0264557 A1 | 9/2016 | Prat Quinones et al. | |
| 2018/0015097 A1 | 1/2018 | Aiguade Bosch et al. | |

FOREIGN PATENT DOCUMENTS

| | | |
|---|---|---|
| CN | 101544572 A | 9/2009 |
| EP | 0147475 | 10/1985 |
| EP | 1 078 629 | 2/2001 |
| EP | 1 894 568 | 3/2008 |
| EP | 2 386 555 | 11/2011 |
| EP | 2 426 121 | 3/2012 |
| EP | 2 592 077 | 5/2013 |
| EP | 2 592 078 | 5/2013 |
| JP | 2011-524897 | 9/2011 |
| WO | WO 98/09632 | 3/1998 |
| WO | WO 99/30703 | 6/1999 |
| WO | WO 00/12067 | 3/2000 |
| WO | WO 01/14339 | 3/2001 |
| WO | WO 2004/074246 | 9/2004 |
| WO | WO 2004/074276 | 9/2004 |
| WO | WO 2004/074812 | 9/2004 |
| WO | WO 2004/089892 | 10/2004 |
| WO | WO 2004/106333 | 12/2004 |
| WO | WO 2005/080375 | 9/2005 |
| WO | WO 2005/111004 | 11/2005 |
| WO | WO 2005/123693 | 12/2005 |
| WO | WO 2006/023454 | 3/2006 |
| WO | WO 2006/023457 | 3/2006 |

(Continued)

OTHER PUBLICATIONS

International Search Report PCT/EP2011/002376, dated Aug. 1, 2011.
International Search Report PCT/EP2012/072311, dated Dec. 10, 2012.
International Search Report PCT/EP2012/072309, dated Dec. 18, 2012.
International Search Report PCT/EP2013/076973, dated Mar. 11, 2014.
International Search Report PCT/EP2014/053871, dated Mar. 27, 2014.
International Search Report PCT/EP2014/053874, dated Apr. 17, 2014.
International Search Report PCT/EP2014/065966, dated Aug. 19, 2014.
International Search Report PCT/EP2014/065965, dated Sep. 18, 2014.
Non-Final Office Action dated Aug. 4, 2015, for U.S. Appl. No. 13/697,060.
Non-Final Office Action dated Mar. 8, 2016, for U.S. Appl. No. 14/956,836.

(Continued)

*Primary Examiner* — Niloofar Rahmani
(74) *Attorney, Agent, or Firm* — Finnegan, Henderson, Farabow, Garrett & Dunner, LLP

(57) ABSTRACT

The present invention relates to novel compounds having β2 adrenergic agonist and M3 muscarinic antagonist dual activity, to pharmaceutical compositions containing them, to the process for their preparation and to their use in respiratory therapies.

26 Claims, No Drawings

(56) References Cited

FOREIGN PATENT DOCUMENTS

| WO | WO 2006/023460 | 3/2006 |
|---|---|---|
| WO | WO 2007/017670 | 2/2007 |
| WO | WO 2007/090859 | 8/2007 |
| WO | WO 2007/107828 | 9/2007 |
| WO | WO 2008/000483 | 1/2008 |
| WO | WO 2008/017824 | 2/2008 |
| WO | WO 2008/017827 | 2/2008 |
| WO | WO 2008/041095 | 4/2008 |
| WO | WO 2008/087437 | 7/2008 |
| WO | WO 2008/096127 | 8/2008 |
| WO | WO 2008/096129 | 8/2008 |
| WO | WO 2008/149110 | 12/2008 |
| WO | WO 2009/013244 | 1/2009 |
| WO | WO 2009/017813 A1 | 2/2009 |
| WO | WO 2009/098448 | 8/2009 |
| WO | WO 2009/139709 | 11/2009 |
| WO | WO 2009/154562 A1 | 12/2009 |
| WO | WO 2010/004517 | 1/2010 |
| WO | WO 2010/015792 | 2/2010 |
| WO | WO 2010/069504 | 6/2010 |
| WO | WO 2010/123766 | 10/2010 |
| WO | WO 2011/012897 | 2/2011 |
| WO | WO 01/14339 | 3/2011 |
| WO | WO 2011/141180 | 11/2011 |
| WO | WO 2012/044825 | 4/2012 |
| WO | WO 2012/085582 | 6/2012 |
| WO | WO 2012/085583 | 6/2012 |
| WO | WO 2012/168349 | 12/2012 |
| WO | WO 2012/168359 | 12/2012 |
| WO | WO 2013/068552 A1 | 5/2013 |
| WO | WO 2013/068554 A1 | 5/2013 |
| WO | WO 2013/068875 | 5/2013 |
| WO | WO 2013/071009 | 5/2013 |
| WO | WO 2013/071169 | 5/2013 |
| WO | WO 2014/086924 | 6/2014 |
| WO | WO 2014/086927 | 6/2014 |
| WO | WO 2014/095920 | 6/2014 |
| WO | WO2014095700 A1 | 6/2014 |
| WO | WO2014100158 A1 | 6/2014 |
| WO | WO 2014/131851 | 9/2014 |
| WO | WO 2014/131852 | 9/2014 |
| WO | WO 2015/011244 | 1/2015 |
| WO | WO 2015/011245 | 1/2015 |
| WO | WO2015049574 A1 | 4/2015 |

OTHER PUBLICATIONS

Non-Final Office Action dated Mar. 21, 2016, for U.S. Appl. No. 14/653,048.
Non-Final Office Action dated May 5, 2016, for U.S. Appl. No. 14/770,206.
Non-Final Office Action dated Jun. 10, 2016, for U.S. Appl. No. 14/770,200.
Non-Final Office Action dated Jul. 8, 2016, for U.S. Appl. No. 14/956,767.
Non-Final Office Action dated Jul. 11, 2016, in U.S. Appl. No. 15/068,926.
Non-Final Office Action Aug. 11, 2016 in U.S. Appl. No. 14/906,991.
Notice of Allowance dated Sep. 2, 2015, in U.S. Appl. No. 14/357,344.
Notice of Allowance dated Dec. 15, 2015, in U.S. Appl. No. 13/697,060.
Notice of Allowance dated Aug. 3, 2016, in U.S. Appl. No. 14/653,048.
Notice of Allowance dated Sep. 13, 2016, in U.S. Appl. No. 14/956,836.
Notice of Allowance dated Sep. 26, 2016, in U.S. Appl. No. 14/770,206.
Notice of Allowance dated May 5, 2017, in U.S. Appl. No. 14/956,767.
Office Action dated Feb. 3, 2015, U.S. Application No. 14/357,344.
Office Action dated Jun. 2, 2015, U.S. Application No. 14/357,344.
Final Office Action dated Nov. 30, 2016, for U.S. Appl. No. 14/770,200.
Final Office Action dated Dec. 1, 2016, for U.S. Appl. No. 14/956,767.
Requirement for Restriction/Election dated Feb. 11, 2016, for U.S. Appl. No. 14/770,200.
Requirement for Restriction/Election dated Mar. 21, 2016, for U.S. Appl. No. 14/956,767.
Requirement for Restriction/Election dated Sep. 22, 2016, for U.S. Appl. No. 14/906,957.
Restriction Requirement dated Feb. 18, 2015, in U.S. Appl. No. 14/357,400.
Restriction Requirement dated Feb. 20, 2015, in U.S. Appl. No. 13/697,060.
U.S. Appl. No. 13/697,060, filed Nov. 9, 2012.
U.S. Appl. No. 14/357,344, filed May 9, 2014.
U.S. Appl. No. 14/357,400, filed May 9, 2014.
U.S. Appl. No. 14/653,048, filed Jun. 17, 2015.
U.S. Appl. No. 14/770,200, filed Aug. 27, 2015.
U.S. Appl. No. 14/770,206, filed Aug. 27, 2015.
U.S. Appl. No. 14/956,767, filed Dec. 2, 2015.
U.S. Appl. No. 14/956,836, filed Dec. 2, 2015.
U.S. Appl. No. 14/906,957, filed Jan. 22, 2016.
U.S. Appl. No. 14/906,991, filed Jan. 22, 2016.
U.S. Appl. No. 15/068,926, filed Mar. 14, 2016.
Banerjee, R. et al., Synthon robustness in saccharinate salts of some substituted pyridines, CrystEngComm, 8: pp. 680-685 (2006).
Barnes, Peter J., "Airway Pharmacology," Textbook of Respiratory Medicine, 3rd Edition, Chapter 11, 2000, pp. 267-272.
Bastin, R.J., et al., "Salt Selection and Optimisation Procedures for Pharmaceutical New Chemical Entities," Org. Process Res. Dev. 4, pp. 427-435 (2000).
Bateman, E.D., "Pharmacodynamics of GSK961081, a bi-functional molecule, in patients with COPD," Pulmonary Pharmacology & Therapeutics, vol. 26, pp. 581-587 (2013).
Berge, S., el al., Pharmaceut. Sc., 1977, vol. 66(1), pp. 1-19.
Chung, K.F., "p38 Mitogen-Activated Protein Kinase Pathways in Asthma and COPD," Chest, 139(6); pp. 1470-1479(2011).
Glossop, Paul A., et al., "Progress in the Development of Inhaled, Long-Acting β2-Adrenoceptor Agonists," Annual Reports in Medicinal Chemistry, vol. 41, 2006, pp. 237-248.
Hoffman, Brian B., "Catecholamines, Sympathomimetic Drugs, and Adrenergic Receptor Antagonists," Goodman & Gilman'S The Pharmacological Basis of Therapeutics $10^{th}$ Edition, Chapter 10, pp. 215-232, 2001.
Hughes, A.D., "Discovery of Muscarinic Acetylcholine Receptor Antagonist and Beta-2 Adrenoceptor Agonist (MABA) Dual Pharmacology Molecules," Respiratory Drug Delivery Europe, pp. 47-58 (2013).
Hughes, A.D., et al., "Multivalent Dual Pharmacology Muscarinic Antagonist and β2 Agonist (MABA) Molecules for the Treatment of COPD, Progress in Medicinal Chemistry," vol. 51, pp. 71-95 (2012).
Hughes, Adam, et al., "Dual-pharmacology Muscarinic Antagonist and β2 Agonist Molecules for the Treatment of Chronic Obstructive Pulmonary Disease," Future Med. Chem., (2011), 3(13), pp. 1585-1605.
Jacobsen, John R., "Third-generation Long-Acting β2 Adrenoceptor Agonists: Medicinal Chemistry Strategies Employed in the identification of Once-Daily Inhaled β2-Adrenoceptor Agonists," Future Med. Chem., 2011, 3(13), pp. 1607-1622.
McNamara, A., et al., "Preclinical Efficacy of THRX-200495, a Dual Pharmacology Muscarinic Receptor Antagonist and β2-Adrenoceptor Agonist (MABA)," Pulmonary Pharmacology & Therapeutics, 25 (5), pp. 357-363, (2012).
Miller-Larsson, A., "Advances in Asthma and COPD Treatment: Combination Therapy with Inhaled Corticosteroids and Long-Acting β2 Agonists," Curr. Pharm. Des. 12(25): pp. 3261-3279 (2006).
Naito, Roy, et al., "Synthesis and Antimuscarinic Properties of Quinuclidin-3-yl 1,2,3,4-Tetrahydroisoquinoline-2-carboxylate Derivatives as Novel Muscarinic Receptor Antagonists," J. Med. Chem., 2005, 48, pp. 6597-6606.

(56) References Cited

OTHER PUBLICATIONS

Norman, P., "Evaluation of WO-2012085582 and WO-2012085583 two identified MABAs: backups to AZD-2115?" Expert Opin. Ther. Patents, 22(11), pp. 1377-1383 (2012).
Norman, P., "Novel dihydroquinoline-based MABAs; clues to the identity of LAS-190792: evaluation of WO20111411802," Expert Opin. Ther. Patents, 22 (2), pp. 185-192 (2012).
Norris, V., et al., "Bronchodilation and Safety of Supratherapeutic Doses of Salbutamol or Ipratropium Bromide Added to Single Dose GSK961081 in Patients with Moderate to Severe COPD," Pulmonary Pharmacology and Therapeutics, vol. 26, pp. 574-580 (2013).
Ray, Nicholas C., et al., "Muscarinic antagonist-β-adrenergic agonist dual pharmacology molecules as bronchodilators: a patent review," Informa Healthcare, vol. 19, No. 1, pp. 1-12 (2009).
Rogers. D.F., "Tachykinin Receptor Antagonists for Asthma and COPD," Exert Opin. Ther. Patents, 11(7) pp. 1097-1121 (2001).
Shan, W., et al., "Dual β2-adrenoceptor Agonists-PDE4 inhibitors for the Treatment of Asthma and COPD," Bioorg. Med. Chem. Lett., 22: pp. 1523-1526 (2012).
P. Heinrich Stahl, Camille G. Wermuth. Handbook of Pharmaceutical Salts. Properties, Selection, and Use. Chapter 12, "Monographs on Acids and Bases", pp. 264-267, 283, 284, 290-293 and 300; Chapter 7, "A procedure for Salt Selection and Optimization", pp. 162-177 and 183-188; Chapter 2, "Solubility and Dissolution of Weak Acids, Bases and Salts"; pp. 19 and 28; Wiley-VCH; 2002.
Thorsson, L., "Factors guiding the choice of delivery device for inhaled corticosteroids in the long-term management of stable asthma and COPD: Focus on budesonide," Respir. Med. 99: pp. 836-849 (2005).
Van Noord, J.A., "Comparison of tiotropium once Daily, Formoterol Twice Daily and Both Combined Once Daily in Patients with COPD," European Respiratory Journal, vol. 26, No. 2, pp. 214-222, 2005.

Wielders, Pascal L.M.L. et al., "A New class of bronchodilator improves lung function in COPD: a trial with GSK961081," Eur Respir J, 42: pp. 972-981 (2013).
International Search Report of International Application No. PCT/EP2015/072158, dated Nov. 2, 2015.
Written Opinion of the International Searching Authority for International Application No. PCT/EP2015/072158.
Brittain, Harry G., "Theory and Principles of Polymorphic Systems," Polymorphism in Pharmaceutical Solids, Second Addition, Drus and the Pharmaceutical Sciences, vol. 192, pp. 1-4, 15-19, 318-430 (2009).
Banerjee, Rahul et al., "Saccharin Salts of Active Pharmaceutical Ingredients, Their Crystal Structures, and Increase water Solubilities," Crystal Growth and Design, vol. 5, No. 6, pp. 2299-2309 (2005).
Hughes, Adam D. et al., "Discovery of muscarinic acetylcholine receptor antagonist and beta 2 adrenoceptor agonist (MABA) dual pharmacology molecules," Bioorganic & Medicinal Chemistry Letters 21, pp. 1354-1358 (2011).
Milara J. et al., Neutrophil Activation in Severe, Early-Onset COPD Patients versus Healthy Non-Smoker Subjects in vitro: Effects of Antioxidant Therapy, Respiration (2012), 83, 147-158.
Nocker R. E. et al., Interleukin-8 in airway inflammation in patients with asthma and chronic obstructive pulmonary disease, International Archives of Allergy and Immunology, 1996, 109 (2): 183-91.
Paulekuhn, G. Steffen et al., "Trends in Active Pharmaceutical Ingredient Salt Selection based on Analysis of the Orange Book Database," J. Med. Chem, vol. 50, pp. 6665-6672 (2007).
Yamamoto C. et al., Airway inflammation in COPD assessed by sputum levels of interleukin-8*; Chest, 1997, 112 (2): 505-10.
Office Action dated Jun. 15, 2017 in U.S. Appl. No. 14/906,957.
Restriction Requirement dated Oct. 20, 2017, in U.S. Appl. No. 15/668,817.

* cited by examiner

BICYCLIC DERIVATIVES HAVING β2 ADRENERGIC AGONIST AND M3 MUSCARINIC ANTAGONIST ACTIVITIES

This application is a national stage filing under 35 U.S.C. § 371 of International Application No. PCT/EP2015/072758, filed on Sep. 25, 2015, which claims priority of European Patent Application No. 14382372.2, filed Sep. 26, 2014. The contents of these applications are each incorporated herein by reference.

FIELD OF THE INVENTION

The present invention relates to novel compounds having β2 adrenergic agonist and M3 muscarinic antagonist dual activity. This invention also relates to pharmaceutical compositions containing them, process for their preparation and their use in respiratory therapies.

BACKGROUND OF THE INVENTION

Bronchodilator agents play an outstanding role in the treatment of such respiratory disorders such as COPD and asthma. Beta-adrenergic agonists and cholinergic muscarinic antagonists are well established bronchodilator agents in widespread clinical use. Beta-adrenergic agonists currently used by the inhaled route include short-acting agents such as salbutamol (qid) or terbutaline (tid) and long-acting agents as salmeterol and formoterol (bid). These agents produce bronchodilation through stimulation of adrenergic receptors on airway smooth muscle, reversing the bronchoconstrictor responses to a variety of mediators, such as acetylcholine. Inhaled muscarinic antagonists currently used include the short-acting ipratropium bromide or oxitropium bromide (qid) and the long-acting tiotropium (qd). These agents produce bronchodilation by reducing vagal cholinergic tone of airway smooth muscle. In addition to improve lung function these agents also improve quality of life and reduce exacerbations. There are in the clinical literature a number of studies strongly demonstrating that the administration of a combination of a beta-2 agonist and a M3 antagonist is more efficacious for the treatment of COPD than either of the components alone (for example, van Noord, J. A., et al., Eur. Respir. J., 26, 214-222). Pharmaceutical compositions containing a combination of both types of bronchodilator agents are also known in the art for use in respiratory therapy. As an example, WO2009013244 discloses a medical composition containing salmeterol as beta-adrenergic agonist agent and tiotropium as antimuscarinic agent.

A single molecule possessing dual activity at muscarinic M3 and adrenergic β2 receptors (MABA) would be desirable both in terms of efficacy and side-effects in the treatment of COPD. It would show also a relevant advantage in terms of formulation compared with the two-component combination. It would be also easier to co-formulate with other therapeutic agents to create triple therapy combinations. Thus there is a need for new compounds having both beta2 receptor agonist and muscarinic activity and being suitable for the treatment of respiratory diseases, such as asthma and COPD.

SUMMARY OF THE INVENTION

The invention provides novel compounds that possess both β2 adrenergic receptor agonist and muscarinic receptor antagonist activities. Accordingly, there is provided a compound of formula (A), or a pharmaceutically acceptable salt, or N-oxide, or isotopically-labeled derivate thereof,

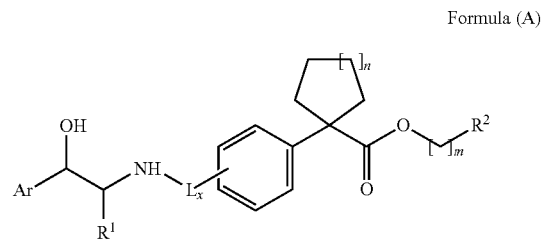

Formula (A)

Wherein

Ar is selected from the group consisting of a $C_{3-10}$ saturated or unsaturated, mono- or bicyclic cycloalkyl group, a $C_5$-$C_{14}$ mono- or bicyclic aryl group, a 3 to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and wherein the cyclic groups independently are optionally substituted with one or more substituents selected from a halogen atom, a cyano group, a nitro group, an oxo group, a carboxy group, a $C_{1-4}$ alkyl group, a $C_{1-4}$ alkoxy group, —$CF_3$, —$OCF_3$, —$NR^eR^f$, —$(CH_2)_p$—OH, —$NR^e(CO)R^f$, —$NR^e$—$SO_2$—$R^g$, —$SO_2NR^eR^f$, —$OC(O)R^h$ and $NR^e(CH_2)_{(0-2)}$—$R^i$, wherein p has a value of 0, 1 or 2 and wherein:

$R^e$ and $R^f$ independently represent a hydrogen atom or a linear or branched $C_{1-4}$ alkyl group, $R^g$ is selected from the group consisting of a linear or branched $C_{1-4}$ alkyl group, a $C_{6-5}$ aryl group, a saturated or unsaturated $C_{3-8}$ cycloalkyl, wherein the cyclic groups independently are optionally substituted with one or more substituents selected from a halogen atom, a $C_{1-4}$ alkyl group and a $C_{1-4}$ alkoxy group, $R^h$ is selected from a hydrogen atom, —$NR^eR^f$ and a $C_{5-6}$ aryl group which is optionally substituted with one or more substituents selected from a $C_{1-4}$ alkyl group and a $C_{1-4}$ alkoxy group, $R^i$ is selected from the group consisting of a $C_{5-6}$ aryl group, a $C_{3-8}$ cycloalkyl group and a 3 to 8 membered saturated or unsaturated heterocyclyl group, which groups independently are optionally substituted with one or more substituents selected from a halogen atom, a $C_{1-4}$ alkyl group and a $C_{1-4}$ alkoxy group, $R^1$ is selected from the group consisting of a hydrogen atom, a linear or branched $C_{1-4}$ alkyl group and a linear or branched $C_{1-4}$ alkoxy group, $R^2$ represents a group of formula:

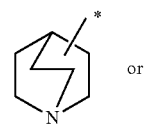

a) or b)

wherein:
R' represents a hydrogen atom or a linear or branched $C_{1-4}$ alkyl group,
* represents the point of attachment of $R^2$ to the remainder of the molecule of formula (A),
n has a value of 0, 1, 2 or 3,
m has a value of 0, 1 or 2,
$L_x$ is a suitable covalent linker.
$L_x$ is a linker space defined as a covalent bond between the —NH— moiety and the phenylene moiety of formula (A).
In one embodiment of the present invention, the linker $L_x$ has the following formula:

Formula (La)

or

Formula (Lb)

wherein k1, k2, s1, s2, l2, t1 and t2 independently have a value of 0 or 1;
$A_1$, $A_2$, $A_3$, $A_4$ and $A_5$ each independently are selected from the group consisting of a direct bond, a $C_{1-10}$ alkylene group, a $C_{2-10}$ alkenylene group and a $C_{2-10}$ alkynylene group, wherein said groups are optionally substituted with one or more substituents selected from a halogen atom, a hydroxy group, a linear or branched $C_{1-4}$ alkyl group, a linear or branched $C_{1-4}$ alkoxy group, a $C_{5-6}$ aryl group and a $C_{3-7}$ cycloalkyl group,
L, $L_1$ and $L_2$ independently are selected from a direct bond, —O—, —$NR^c$—, —S—, —S(O)—, —$SO_2$—, —$NR^c(CO)$—, —(CO)$NR^c$—, —$NR^c(CO)(CH_2)_q$O—, —O(CH$_2$)$_q$(CO)$NR^c$—, —O(CH$_2$)$_q$(CO)O—, —O(CO)(CH$_2$)$_q$O—, —$NR^c$(CH$_2$)$_q$(CO)$NR^c$—, —$NR^c$(CO)(CH$_2$)$_q$$NR^c$(CO)—, —O(CH$_2$)$_q$$NR^c$—, —$NR^c$(CH$_2$)$_q$O—, —$NR^c$(CO)$NR^d$—, —C(O)—, —OC(O)—, —S(O)$_2$$NR^c$—, —$NR^c$S(O)$_2$—, —$NR^c$S(O)$_2$$NR^d$—, —C(O)$NR^c$S(O)$_2$— and —S(O)$_2$$NR^c$C(O)—, wherein $R^c$ and $R^d$ are independently selected from a hydrogen atom and a linear or branched $C_{1-4}$ alkyl group and q has a value of 0, 1, 2, 3 or 4.
G and $G_2$ independently are selected from the group consisting of a direct bond, a $C_{3-10}$ mono- or bicyclic cycloalkyl group, a $C_5$-$C_{14}$ mono- or bicyclic aryl group, a 3 to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and a bicyclic ring system comprising two monocyclic ring systems which are linked between each other by a covalent bond wherein said monocyclic ring systems are independently selected from a $C_{3-8}$ cycloalkyl group, a $C_{5-6}$ aryl group, a 3 to 8-membered saturated or unsaturated heterocyclyl group having one or more heteroatoms selected from N, S and O and a 5- to 6-membered heteroaryl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a carboxy group, a cyano group, a nitro group, a hydroxy group, an oxo group, a trifluoromethyl group and a trifluoromethoxy group.

In a preferred embodiment, all of k1, k2, s1, s2, l2, t1 and t2 have a value of 0

In a still preferred embodiment the linker L has the following formula (Lb1):

Formula (Lb1)

wherein $A_1$, $A_2$, L and G are as defined above.

In a preferred embodiment, compounds of the present invention have the following formula (B):

Formula (B)

Wherein Ar, $A_1$, $A_2$, $R^1$, L, G, n and $R^2$ are as defined above.

The invention also provides synthetic processes and intermediates described herein, which are useful for preparing compounds of the invention.

The invention further provides a pharmaceutical composition comprising at least a compound of the invention and a pharmaceutically-acceptable carrier.

The invention also provides a compound of the invention as described herein for use in the treatment of human or animal body by therapy.

The invention is also directed to the compounds as described herein, for use in the treatment of a pathological condition or disease associated with dual β2 adrenergic receptor and muscarinic receptor activities in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease.

The invention also provides the use of the compounds of the invention as described herein, for the manufacture of a medicament for the treatment of a pathological condition or disease associated with dual β2 adrenergic receptor and muscarinic receptor activities, in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease.

The invention is also directed to a method of treatment of a pathological condition or disease associated with dual β2 adrenergic receptor and muscarinic receptor activities, in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease, comprising administering a therapeutically effective amount of the compounds of the invention or a pharmaceutical composition of the invention to a subject in need of such treatment.

The invention also provides a combination product comprising (i) at least a compound of the invention as described herein; and (ii) one or more active ingredients for simultaneous, separate or sequential use in the treatment of the human or animal body.

DETAILED DESCRIPTION OF THE INVENTION

When describing the compounds, compositions and methods of the invention, the following terms have the following meanings, unless otherwise indicated.

As used herein the term $C_{1-4}$ alkyl embraces linear or branched radicals having 1 to 4 carbon atoms. Examples include methyl, ethyl, n-propyl, i-propyl, n-butyl, sec-butyl, t-butyl, As used herein, the term $C_1$-$C_{10}$ alkylene embraces divalent alkyl moieties typically having from 1 to 10 carbon atoms, preferably from 1 to 6 carbon atoms, more preferably from 1 to 4 carbons atoms. Examples of $C_1$-$C_{10}$ alkylene radicals include methylene, ethylene, propylene, butylene, pentylene and hexylene radicals.

As used herein, the term $C_2$-$C_{10}$ alkenylene embraces divalent alkenyl moieties typically having from 2 to 10 carbon atoms, preferably from 2 to 6 carbon atoms, more preferably from 2 to 4 carbons atoms. Examples of $C_2$-$C_{10}$ alkenylene radicals include vinylene, propenylene, butenylene, pentenylene, hexenylene, heptenylene, octenylenyl radicals.

As used herein, the term $C_2$-$C_{10}$ alkynylene embraces divalent alkynyl moieties having 2 to 10 carbon atoms, preferably from 2 to 6 carbon atoms, more preferably from 2 to 4 carbons atoms. Examples include propynylene, butynylene, heptynylene, octynylene.

As used herein, the term $C_{1-4}$ alkoxy (or alkyloxy) embraces optionally substituted, linear or branched oxy-containing radicals each having alkyl portions of 1 to 4 carbon atoms. Preferred alkoxy radicals include methoxy, ethoxy, n-propoxy, i-propoxy, n-butoxy, sec-butoxy and t-butoxy.

As used herein, the term $C_{3-10}$ cycloalkyl radical embraces saturated monocyclic or polycyclic carbocyclic radicals having from 3 to 10 carbon atoms, preferably from 3 to 7 carbon atoms. Polycyclic cycloalkyl radicals contain two or more fused cycloalkyl groups, preferably two cycloalkyl groups. Examples of cycloalkyl groups include cyclopropyl, cyclobutyl, cyclopentyl, cyclohexyl, cycloheptyl, cyclooctyl, cyclononyl, decahydronaphthyl (decalyl), bicyclo[2.2.2]octyl, adamantyl, camphyl and bornyl.

As used herein, the term $C_5$-$C_{14}$ aryl radical embraces typically a $C_5$-$C_{14}$, preferably a $C_6$-$C_{14}$, more preferably a $C_6$-$C_{10}$ monocyclic or polycyclic aryl radical. Examples of aryl radicals include phenyl, naphthyl, naphthalenyl, anthranyl and phenanthryl.

As used herein, the term 5- to 14-membered heteroaryl radical embraces typically a 5- to 14-membered ring system comprising at least one heteroaromatic ring and containing at least one heteroatom selected from O, S and N. A 5- to 14-membered heteroaryl radical may be a single ring or two or more fused rings wherein at least one ring contains a heteroatom.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl and the various pyrrolopyridyl radicals.

As used herein, the term 3- to 14-membered heterocyclyl radical embraces typically a non-aromatic, saturated or unsaturated $C_3$-$C_{14}$ carbocyclic ring system in which one or more, for example 1, 2, 3 or 4 of the carbon atoms preferably 1 or 2 of the carbon atoms are replaced by a heteroatom selected from N, O and S. A heterocyclic radical may be a single ring or two or more fused rings wherein at least one ring contains a heteroatom, and may have one or more double bonds Examples of 3 to 14-membered heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, thiaranyl, aziridinyl, oxetanyl, thiatanyl, azetidinyl, 4,5-dihydro-oxazolyl, 2-benzofuran-1(3H)-one, 1,3-dioxol-2-one, tetrahydrofuranyl, 3-aza-tetrahydrofuranyl, tetrahydrothiophenyl, tetrahydropyranyl, tetrahydrothiopyranyl, 1,4-azathianyl, oxepanyl, thiephanyl, azepanyl, 1,4-dioxepanyl, 1,4-oxathiepanyl, 1,4-oxaazepanyl, 1,4-dithiepanyl, 1,4-thiezepanyl, 1,4-diazepanyl, tropanyl, (1S,5R)-3-aza-bicyclo[3.1.0]hexyl, 3,4-dihydro-2H-pyranyl, 5,6-dihydro-2H-pyranyl, 2H-pyranyl, 2,3-hydrobenzofuranyl, 1,2,3,4-tetrahydropyridinyl, 1,2,5,6-tetrahydropyridinyl, isoindolinyl and indolinyl.

As used herein, the term halogen atom embraces chlorine, fluorine, bromine or iodine atoms typically a fluorine, chlorine or bromine atom. The term halo when used as a prefix has the same meaning.

Also included within the scope of the invention are the isomers, polymorphs, pharmaceutically acceptable salts, N-oxides, isotopes, solvates and prodrugs of the compounds of formula (A). Any reference to a compound of formula (A) throughout the present specification includes a reference to any isomer, polymorph, pharmaceutically acceptable salt, N-oxide, isotope, solvate or prodrug of such compound of formula (A).

Isomers

Compounds containing one or more chiral centre may be used in enantiomerically or diastereoisomerically pure form, in the form of racemic mixtures and in the form of mixtures enriched in one or more stereoisomer. The compounds of the present invention as described and claimed encompass the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

The compounds of Formula (A) may exhibit the phenomena of tautomerism and structural isomerism. Tautomers exist as mixtures of a tautomeric set in solution. In solid form, usually one tautomer predominates. Even though one tautomer may be described, the present invention includes all tautomers of the compounds of Formula (A).

Polymorphs

The compounds of the present invention may exist in different physical forms, i.e. amorphous and crystalline forms.

Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of the present invention, including all polymorphic forms ("polymorphs") thereof, are included within the scope of the invention.

Salts

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid; and organic acids, for example citric, fumaric, gluconic, glutamic, lactic, maleic, malic, mandelic, mucic, ascorbic, oxalic, pantothenic, succinic, tartaric, benzoic, acetic, methanesulphonic, ethanesulphonic, benzenesulphonic, p-toluenesulphonic acid, xinafoic (1-hydroxy-2-naphthoic acid), napadisilic (1,5-naphthalenedisulfonic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to the invention are quaternary ammonium compounds wherein an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

N-oxides

As used herein, an N-oxide is formed from the tertiary basic amines or imines present in the molecule, using a convenient oxidising agent.

Isotopes

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}K$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of the invention. As used herein, the term deuterated derivative embraces compounds of the invention where in a particular position at least one hydrogen atom is replaced by deuterium. Deuterium (D or $^2$H) is present at a natural abundance of 0.015 molar %.

Solvates

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-solvate form of the compounds.

Prodrugs

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'pro-moieties' as described, for example, in Design of Prodrugs by H. Bundgaard (Elsevier, 1985).

Typically, Ar represents a group of formula:

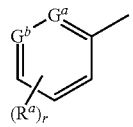

(a)

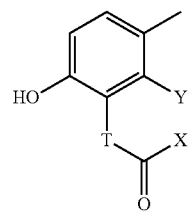

(b)

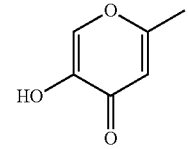

(c)

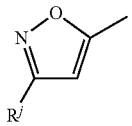

(d)

wherein $G^a$ and $G^b$ independently are selected from a nitrogen atom and a carbon atom, r has a value of 0, 1, 2 or 3 and $R^a$ is selected from the group consisting of a halogen atom, an amino group, a cyano group, a nitro group, an oxo group, a carboxy group, a $C_{1-4}$ alkyl group, a $C_{1-4}$ alkoxy group, —CF$_3$, —OCF$_3$, —(CH$_2$)$_p$—OH, —NH(CO)H, —NH—SO$_2$—R$^g$, —SO$_2$NH$_2$, —OC(O)H, —O(CO)-(4-methyl)phenyl, —O(CO)—N(CH$_3$)$_2$, —OC(O)NH$_2$ and —NH(CH$_2$)$_{(1-2)}$—R$^i$, group, wherein p is as defined above and R$^g$ and R$^i$ independently are selected from a phenyl group optionally substituted with a one substituent selected from a methyl group or a methoxy group, R$^j$ represents a halogen atom, T is selected from the group consisting of —CH$_2$— and —NH—, Both X and Y represent a hydrogen atom or X together with Y form the group CH$_2$—CH$_2$—, —CH=CH—, —CH$_2$—O— or —S—, wherein in the case of —CH$_2$—O— the methylene group is bound to the carbonyl group holding X and the oxygen atom is bound to the carbon atom in the phenyl ring holding Y, Preferably, Ar represents a compound of formula (a) or (b) wherein:

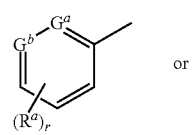

(a)

or

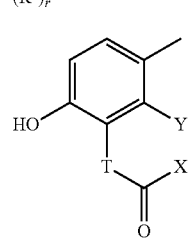

(b)

Both $G^a$ and $G^b$ represent a carbon atom, $R^a$ is selected from the group consisting of halogen atom, amino group, cyano group, nitro group, —$(CH_2)_p$—OH, —NH(CO)H, —NH—$SO_2$—$CH_3$, —$SO_2NH_2$, —OC(O)H, —O(CO)-(4-methyl)phenyl, —O(CO)—N$(CH_3)_2$, —OC(O)$NH_2$ and —$CF_3$ group, wherein p has a value of 0, 1 or 2, T represents —NH— group, Both X and Y represent a hydrogen atom or X together with Y form the group —CH=CH—, —$CH_2$—$CH_2$—, —$CH_2$—O— or —S—, wherein in the case of —$CH_2$—O— the methylene group is bound to the carbon atom in the amido substituent holding X and the oxygen atom is bound to the carbon atom in the phenyl ring holding Y In a still preferred embodiment Ar is selected from the group consisting of 3-bromoisoxazol-5-yl, 3,4-dihydroxyphenyl, 4-hydroxy-3-(methylsulfonamido)phenyl, 3,4-bis(4-methylbenzoyloxy)phenyl, 3,5-bis(dimethylcarbamoyloxy)phenyl, (5-hydroxy-6-hydroxymethyl)pyrid-2-yl, (4-amino-3,5-dichloro)phenyl, 4-hydroxyphenyl, 4-hydroxy-3-(2-hydroxyethyl)phenyl, 4-hydroxy-3-(hydroxymethyl)phenyl, [4-amino-3-chloro-5-(trifluoromethyl)]phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl, 5-hydroxy-3-oxo-3,4-dihydro-2H-benzo[b][1,4]oxazin-8-yl, 4-hydroxy-2-oxo-2,3-dihydrobenzo[d]thiazol-7-yl. Preferably Ar is selected from the group consisting of 4-hydroxy-3-(hydroxymethyl)phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl and 5-hydroxy-3-oxo-3,4-dihydro-2H-benzo[b][1,4]oxazin-8-yl.

In another embodiment Ar represents a compound of formula (b) wherein X and Y are as defined above and T represents a —NH— group.

Still in another embodiment of the present invention, compounds of the present invention have the following formula (I):

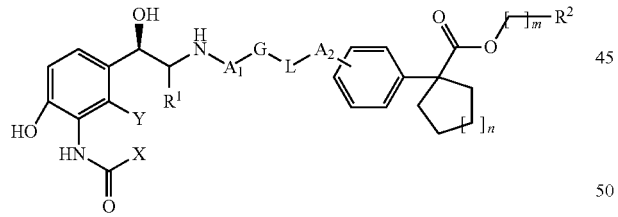

Formula (I)

Wherein:
X and Y are both hydrogen atoms or X together with Y form the group —CH=CH—, —$CH_2$—O— or —S—, wherein in the case of —$CH_2$—O— the methylene group is bound to the carbon atom in the amido substituent holding X and the oxygen atom is bound to the carbon atom in the phenyl ring holding Y, $A_1$ and $A_2$ independently are selected from the group consisting of a direct bond, a $C_{1-10}$ alkylene group, a $C_{2-10}$ alkenylene group and a $C_{2-10}$ alkynylene group, wherein said groups are optionally substituted with one or more substituents selected from a halogen atom, a hydroxy group, a linear or branched $C_{1-4}$ alkyl group, a linear or branched a $C_{1-4}$ alkoxy group, a $C_{5-6}$ aryl group and a $C_{3-7}$ cycloalkyl group, G is selected from the group consisting of a direct bond, a $C_{3-10}$ mono- or bicyclic cycloalkyl group, a $C_{5-14}$ mono- or bicyclic aryl group, a 3- to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and a bicyclic ring system consisting of two monocyclic ring systems which are linked between each other by a covalent bond wherein said monocyclic ring systems are independently selected from a $C_{3-8}$ cycloalkyl group, a $C_{5-6}$ aryl group, a 3- to 8-membered saturated or unsaturated heterocyclyl group having one or more heteroatoms selected from N, S and O and a 5- to 6-membered heteroaryl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a carboxy, group, a cyano group, a nitro group, a hydroxy group, an oxo group, a trifluoromethyl group and a trifluoromethoxy group, L is selected from a direct bond, —O—, —$NR^c$—, —S—, —S(O)—, —$SO_2$—, —$NR^c$(CO)—, —(CO)$NR^c$—, —$NR^c$(CO)($CH_2)_q$O—, —O($CH_2)_q$(CO)$NR^c$—, —O($CH_2)_q$(CO)O—, —O(CO)($CH_2)_q$O—, —$NR^c$($CH_2)_q$(CO)$NR^c$—, —$NR^c$(CO)($CH_2)_q$$NR^c$(CO)—, —O($CH_2)_q$$NR^c$—, —$NR^c$($CH_2)_q$O—, —$NR^c$(CO)$NR^d$—, —C(O)—, —C(O)O—, —OC(O)—, —$S(O)_2$$NR^c$—, —$NR^c$$S(O)_2$—, —$NR^c$$S(O)_2$$NR^d$—, —C(O)$NR^c$$S(O)_2$— and —$S(O)_2$$NR^c$C(O)—, wherein $R^c$ and $R^d$ are independently selected from a hydrogen atom and a linear or branched $C_{1-4}$ alkyl group and q has a value of 0, 1, 2, 3 or 4, n has a value of 0, 1, 2 or 3, m has a value of 0, 1 or 2, $R^2$ represents a group of formula:

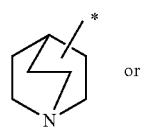

a)

or

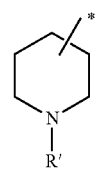

b)

Wherein
R' represents a hydrogen atom or a $C_{1-4}$ alkyl group, and

* represents the point of attachment to the remainder of the molecule.

Still in another embodiment of the present invention, compounds of the present invention have the following formula (I*):

Formula (I*)

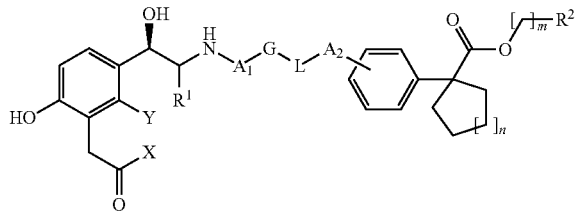

Wherein:
- X and Y are both hydrogen atoms or X together with Y form the group —CH=CH—, —CH$_2$—O— or —S—, wherein in the case of —CH$_2$—O— the methylene group is bound to the carbon atom in the amido substituent holding X and the oxygen atom is bound to the carbon atom in the phenyl ring holding Y,
- A$_1$ and A$_2$ independently are selected from the group consisting of a direct bond, a C$_{1-10}$ alkylene group, a C$_{2-10}$ alkenylene group and a C$_{2-10}$ alkynylene group, wherein said groups are optionally substituted with one or more substituents selected from a halogen atom, a hydroxy group, a linear or branched C$_{1-4}$ alkyl group, a linear or branched a C$_{1-4}$ alkoxy group, a C$_{5-6}$ aryl group and a C$_{3-7}$ cycloalkyl group,
- G is selected from the group consisting of a direct bond, a C$_{3-10}$ mono- or bicyclic cycloalkyl group, a C$_{5-14}$ mono- or bicyclic aryl group, a 3- to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and a bicyclic ring system consisting of two monocyclic ring systems which are linked between each other by a covalent bond wherein said monocyclic ring systems are independently selected from a C$_{3-8}$ cycloalkyl group, a C$_{5-6}$ aryl group, a 3- to 8-membered saturated or unsaturated heterocyclyl group having one or more heteroatoms selected from N, S and O and a 5- to 6-membered heteroaryl group having one or more heteroatoms selected from N, S and O, wherein the cyclic groups independently are optionally substituted with one or more substituents selected from a halogen atom, a C$_{1-4}$ alkyl group, a C$_{1-4}$ alkoxy group, a carboxy group, a cyano group, a nitro group, a hydroxy group, an oxo group, a trifluoromethyl group and a trifluoromethoxy group,
- L is selected from a direct bond, —O—, —NR$^c$—, —S—, —S(O)—, —SO$_2$—, —NR$^c$(CO)—, —(CO)NR$^c$—, —NR$^c$(CO)(CH$_2$)$_q$O—, —O(CH$_2$)$_q$(CO)NR$^c$—, —O(CH$_2$)$_q$(CO)O—, —O(CO)(CH$_2$)$_q$O—, —NR$^c$(CH$_2$)$_q$(CO)NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, —OC(O)—, —S(O)$_2$NR$^c$—, —NR$^c$S(O)$_2$—, —NR$^c$S(O)$_2$NR$^d$—, —C(O)NR$^c$S(O)$_2$— and —S(O)$_2$NR$^c$C(O)—, wherein R$^c$ and R$^d$ are independently selected from a hydrogen atom and a linear or branched C$_{1-4}$ alkyl group and q has a value of 0, 1, 2, 3 or 4,
- n has a value of 0, 1, 2 or 3,
- m has a value of 0, 1 or 2, R$^2$ represents a group of formula:

a)

or

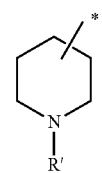
b)

Wherein
R' represents a hydrogen atom or a C$_{1-4}$ alkyl group, and
* represents the point of attachment to the remainder of the molecule.

Typically, A$_1$ and A$_2$ independently are selected from the group consisting of C$_{1-6}$ alkylene group, C$_{1-6}$ alkenylene group and C$_{1-6}$ alkynylene group, wherein said groups are optionally substituted with one or more substituents selected from a halogen atom, a hydroxy group, a C$_{1-2}$ alkyl group, a C$_{1-2}$ alkoxy group, a C$_{5-6}$ aryl group and a C$_{3-6}$ cycloalkyl group.

Preferably, A$_1$ and A$_2$ independently represent a C$_{1-6}$ alkylene group optionally substituted with one or more substituents selected from a C$_{1-2}$ alkyl group and a C$_{1-2}$ alkoxy group, preferably A$_1$ and A$_2$ independently represent a C$_{1-4}$ alkylene group, more preferably, the alkylene groups are independently unsubstituted.

Typically, X together with Y form the group —CH=CH— or —CH$_2$—O—. Preferably, X together with Y form the group —CH=CH—.

Typically, L is selected from the group consisting a direct bond, —O—, —NR$^c$—, —S—, —S(O)—, —SO$_2$—, —NR$^c$(CO)—, —(CO)NR$^c$—, —NR$^c$(CO)(CH$_2$)$_q$O—, —O(CH$_2$)$_q$(CO)NR$^c$—, —O(CH$_2$)$_q$(CO)O—, —NR$^c$(CH$_2$)$_q$(CO)NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, —OC(O)—, —S(O)$_2$NR$^c$—, —NR$^c$S(O)$_2$—, —C(O)NR$^c$S(O)$_2$— and —S(O)$_2$NR$^c$C(O)—, wherein R$^c$ and R$^d$ are independently selected from a hydrogen atom and a C$_{1-2}$ alkyl group and q has a value of 0, 1, 2 or 3.

Preferably, L is selected from the group consisting of direct bond, —O—, —NR$^c$—, —NR$^c$(CO)—, —(CO)NR$^c$—, —NR$^c$(CO)(CH$_2$)$_q$O—, —O(CH$_2$)$_q$(CO)NR$^c$—, —O(CH$_2$)$_q$(CO)O—, —NR$^c$(CH$_2$)$_q$(CO)NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, —OC(O)— wherein R$^c$ and R$^d$ independently are selected from a hydrogen atom and a methyl group, and q has a value of 0, 1 or 2.

Preferably L is selected from a direct bond, —NR$^c$(CO)—, —(CO)NR$^c$—, —NR$^c$(CO)(CH$_2$)$_q$O—, —O(CH$_2$)$_q$(CO)NR$^c$— and —C(O)O—, wherein R$^c$ represents a hydrogen atom and a methyl group. More preferably L is selected from —NR$^c$(CO)—, —(CO)NR$^c$—, —O(CH$_2$)$_q$(CO)NR$^c$— and —C(O)O—, and q has a value of 1 or 2.

Typically G is selected from the group consisting of a direct bond, a C$_{3-7}$ cycloalkyl group, a C$_{5-14}$ mono- or bicyclic aryl group, a 3- to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a carboxy, group, a cyano group, a nitro group, a hydroxy group and an oxo group.

Preferably G is selected from the group consisting of a $C_{3-7}$ cycloalkyl group, a $C_5$-$C_6$ aryl group, a 8- to 10-membered saturated or unsaturated bicyclic heterocyclyl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a hydroxy group and an oxo group, more preferably G represents a phenyl group optionally substituted with one or two substituents selected from a halogen atom, a $C_{1-4}$ alkyl group and a $C_{1-4}$ alkoxy group, preferably the phenyl group is substituted with two substituents selected from a methyl group, a methoxy group and a chlorine atom, being preferably chlorine atom and methoxy group.

Typically $R^2$ represents a group of formula:

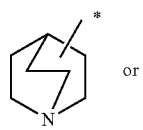

a) or

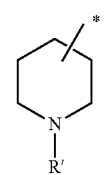

b)

Wherein R' represents a hydrogen atom or a methyl group,

Preferably $R^2$ represents the quinuclidine derivative group of formula a):

Preferably the asymmetric carbon atom of the quinuclidine ring to which the remaining molecule is attached has the (R) Configuration.

Still in another embodiment of the present invention, compounds of the present invention have the following formula (I):

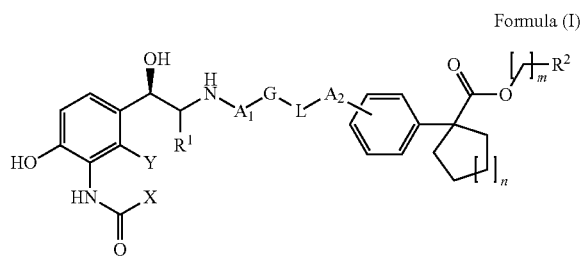

Formula (I)

Wherein:

X together with Y form the group —CH═CH—, $A_1$ and $A_2$ independently represents a $C_{1-4}$ alkylene group, $R^1$ represents a hydrogen atom, G is selected from the group consisting of a direct bond, a cyclohexyl group, a phenyl group, a 6- to 10-membered saturated or unsaturated mono- or bicyclic heterocyclyl group having one or more heteroatoms selected from N and O and a 5- to 10-membered mono- or bicyclic heteroaryl group having one or more heteroatoms selected from N, S and O, wherein the cyclic groups independently are optionally substituted with one or more substituents selected from a chlorine atom, a methoxy group, a hydroxyl group and an oxo group, L is selected from a direct bond, —O—, —$NR^c$(CO)—, —(CO)$NR^c$—, —O(CH$_2$)$_q$(CO)$NR^c$—, —O(CH$_2$)$_q$(CO)O—, —$NR^c$(CH$_2$)$_q$(CO)$NR^c$—, —$NR^c$(CO)(CH$_2$)$_q$$NR^c$(CO)—, —C(O)—, —C(O))—, wherein $R^c$ represents a hydrogen atom or a methyl group and q has a value of 0, 1 or 4, n has a value of 1 or 2, m has a value of 0 or 1, $R^2$ represents a group of formula:

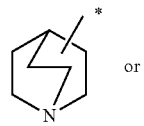

a) or

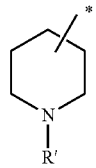

b)

Wherein

R' represents a hydrogen atom or a methyl group, and

* represents the point of attachment to the remainder of the molecule.

Still in another embodiment of the present invention, compounds of the present invention have the following formula (I*):

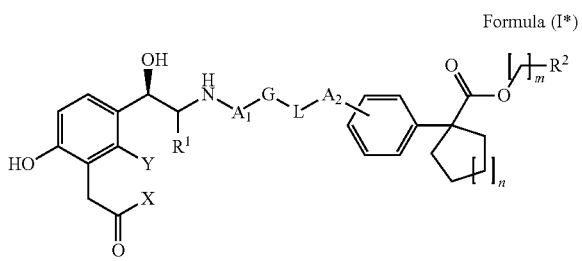

Formula (I*)

Wherein:

X together with Y form the group —CH═CH—,

A₁ and A₂ independently represents a $C_{1-4}$ alkylene group,

R¹ represents a hydrogen atom,

G is selected from the group consisting of a direct bond, a cyclohexyl group, a phenyl group, a 6- to 10-membered saturated or unsaturated mono- or bicyclic heterocyclyl group having one or more heteroatoms selected from N and O and a 5- to 10-membered mono- or bicyclic heteroaryl group having one or more heteroatoms selected from N, S and O, wherein the cyclic groups independently are optionally substituted with one or more substituents selected from a chlorine atom, a methoxy group, a hydroxyl group and an oxo group, L is selected from a direct bond, —O—, —NR$^c$(CO)—, —(CO)NR$^c$—, —O(CH$_2$)$_q$(CO)NR$^c$—, —O(CH$_2$)$_q$(CO)O—, —NR$^c$(CH$_2$)$_q$(CO)NR$^c$—, —NR$^c$(CO)(CH$_2$)$_q$NR$^c$(CO)—, —C(O)—, —C(O)O—, wherein R$^c$ represents a hydrogen atom or a methyl group and q has a value of 0, 1 or 4, n has a value of 1 or 2, m has a value of 0 or 1, R² represents a group of formula:

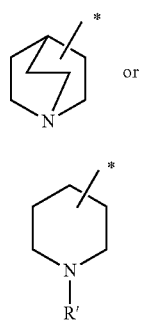

a)

or b)

Wherein

R' represents a hydrogen atom or a methyl group, and

* represents the point of attachment to the remainder of the molecule.

In a still preferred embodiment of the present invention, compounds of the present invention have the following formula (I):

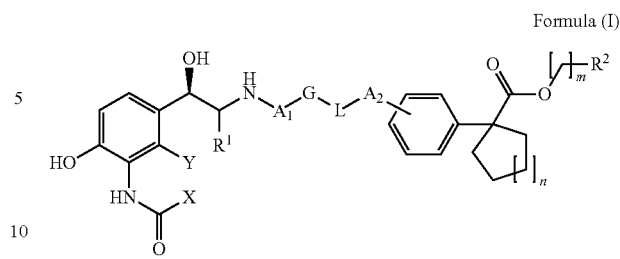

Formula (I)

Wherein:

X together with Y form the group —CH═CH—,

A₁ and A₂ independently represents a $C_{1-4}$ alkylene group,

G represents a phenyl group substituted with two substituents selected from a methoxy group and a chlorine atom, L is selected from —NR$^c$(CO)—, —(CO)NR$^c$—, —O(CH$_2$)$_q$(CO)NR$^c$— and —C(O)O—, and q has a value of 1 or 2, n has a value of 2, m has a value of 0, R² represents the quinuclidine derivative group of formula a):

wherein the asymmetric carbon atom of the quinuclidine ring to which the remaining molecule is attached has the (R) configuration.

In a still preferred embodiment of the present invention, compounds of the present invention have the following formula (I*):

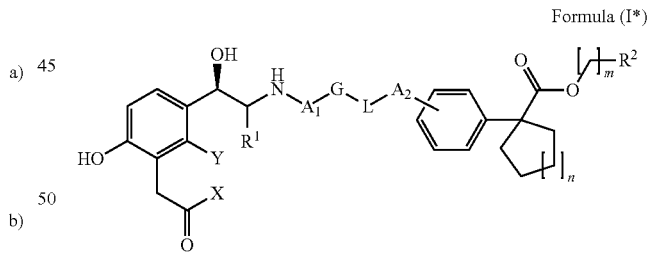

Formula (I*)

Wherein:

X together with Y form the group —CH═CH—,

A₁ and A₂ independently represents a $C_{1-4}$ alkylene group,

G represents a phenyl group substituted with two substituents selected from a methoxy group and a chlorine atom, L is selected from —NR$^c$(CO)—, —(CO)NR$^c$—, —O(CH$_2$)$_q$(CO)NR$^c$— and —C(O)O—, and q has a value of 1 or 2, n has a value of 2, m has a value of 0, R² represents the quinuclidine derivative group of formula a):

wherein the asymmetric carbon atom of the quinuclidine ring to which the remaining molecule is attached has the (R) configuration.

In another embodiment of the present invention, compounds of the present invention have the following formula (Ia):

Formula (Ia)

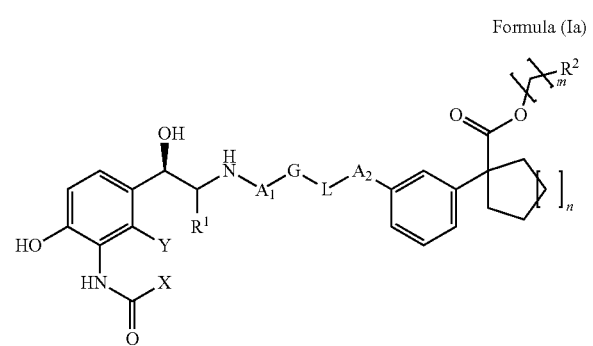

wherein X, Y, $R^1$, $R^2$, $A_1$, $A_2$, G, L, n and m are as defined above.

In another embodiment of the present invention, compounds of the present invention have the following formula (Ia*):

Formula (Ia*)

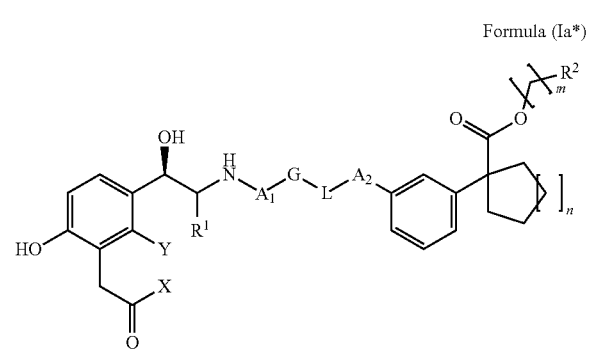

wherein X, Y, $R^1$, $R^2$, $A_1$, $A_2$, G, L, n and m are as defined above.

Particular individual compounds of the invention include:
(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}phenyl)cyclohexanecarboxylate, (3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate, (3R)-1-azabicyclo[2.2.2]oct-3-yl 1-(3-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)phenyl]cyclohexanecarboxylate, (3R)-1-azabicyclo[2.2.2]oct-3-yl 1-(3-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]propyl}phenyl)cyclohexanecarboxylate, (3R)-1-azabicyclo[2.2.2]oct-3-yl 1-(3-{4-[5-({[(2R)-2-hydroxy-2-(8-hydroxy-2-oxo-1,2-dihydroquinolin-5-yl)ethyl]amino}methyl)-1H-1,2,3-benzotriazol-1-yl]butyl}phenyl)cyclohexanecarboxylate, (3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxo-3,4-dihydroquinolin-1(2H)-yl]butyl}phenyl)cyclohexanecarboxylate, (3R)-1-azabicyclo[2.2.2]oct-3-yl 1-(3-{4-[5-{[(2R)-2-hydroxy-2-(8-hydroxy-2-oxo-1,2-dihydroquinolin-5-yl)ethyl]amino}pentyl)amino]-4-oxobutyl}phenyl)cyclohexanecarboxylate, (3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxoquinolin-1(2H)-yl]butyl}phenyl)cyclohexanecarboxylate, (3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)phenyl]cyclohexanecarboxylate, (3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}oxy)propyl]phenyl}cyclohexanecarboxylate, (3R)-1-azabicyclo[2.2.2]oct-3-yl 1-[3-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)phenyl]cyclohexanecarboxylate, (3R)-1-azabicyclo[2.2.2]oct-3-yl 1-(3-{3-[[2-chloro-4-({[(2R)-2-hydroxy-2-(8-hydroxy-2-oxo-1,2-dihydroquinolin-5-yl)ethyl]amino}methyl)-5-methoxybenzoyl](methyl)amino]propyl}phenyl)cyclohexanecarboxylate, 3-[3-(1-{[(3R)-1-azabicyclo[2.2.2]oct-3-yloxy]carbonyl}cyclohexyl)phenyl]propyl 2-chloro-4-({[(2R)-2-hydroxy-2-(8-hydroxy-2-oxo-1,2-dihydroquinolin-5-yl)ethyl]amino}methyl)-5-methoxybenzoate, (3R)-1-azabicyclo[2.2.2]oct-3-yl 1-(3-{[4-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}oxy)cyclohexyl]methyl}phenyl)cyclohexanecarboxylate, 3-[3-(1-{[(3R)-1-azabicyclo[2.2.2]oct-3-yloxy]carbonyl}cyclohexyl)phenyl]propyl 6-({[(2R)-2-hydroxy-2-(8-hydroxy-2-oxo-1,2-dihydroquinolin-5-yl)ethyl]amino}methyl)nicotinate, (3R)-1-azabicyclo[2.2.2]oct-3-yl 1-(3-{4-[4-(2-{[(2R)-2-hydroxy-2-(8-hydroxy-2-oxo-1,2-dihydroquinolin-5-yl)ethyl]amino}ethyl)piperidin-1-yl]-4-oxobutyl}phenyl)cyclohexanecarboxylate, (3R)-1-azabicyclo[2.2.2]oct-3-yl 1-(3-{4-[(5-{[4-({[(2R)-2-hydroxy-2-(8-hydroxy-2-oxo-1,2-dihydroquinolin-5-yl)ethyl]amino}methyl)phenyl]amino}-5-oxopentyl)(methyl)amino]-4-oxobutyl}phenyl)cyclohexanecarboxylate, 1-azabicyclo[2.2.2]oct-4-ylmethyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate, (3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}amino)propyl]phenyl}cyclohexanecarboxylate, (3R)-1-azabicyclo[2.2.2]oct-3-yl 1-[3-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl)phenyl]cyclohexanecarboxylate,
(3R)-1-azabicyclo[2.2.2]oct-3-yl 1-{3-[4-({[6-({[(2R)-2-hydroxy-2-(8-hydroxy-2-oxo-1,2-dihydroquinolin-5-yl)ethyl]amino}methyl)pyridin-3-yl]carbonyl}amino)butyl]phenyl}cyclohexanecarboxylate,
4-[3-(1-{[(3R)-1-azabicyclo[2.2.2]oct-3-yloxy]carbonyl}cyclohexyl)phenyl]butyl 2-chloro-4-({[(2R)-2-hydroxy-2-(8-hydroxy-2-oxo-1,2-dihydroquinolin-5-yl)ethyl]amino}methyl)-5-methoxybenzoate,
(3R)-1-azabicyclo[2.2.2]oct-3-yl 1-(3-{4-[5-({[(2R)-2-hydroxy-2-(8-hydroxy-2-oxo-1,2-dihydroquinolin-5-yl)ethyl]amino}methyl)-1-oxo-1,3-dihydro-2H-isoindol-2-yl]butyl}phenyl)cyclohexanecarboxylate,
(3R)-1-azabicyclo[2.2.2]oct-3-yl 1-{3-[4-({[2-chloro-4-({[2-hydroxy-2-(8-hydroxy-2-oxo-1,2-dihydroquinolin-5-yl)ethyl]amino}methyl)-5-methoxyphenoxy]acetyl}amino)butyl]phenyl}cyclohexanecarboxylate,
(3R)-1-azabicyclo[2.2.2]oct-3-yl 1-{3-[3-({[6-({[(2R)-2-hydroxy-2-(8-hydroxy-2-oxo-1,2-dihydroquinolin-5-yl)ethyl]amino}methyl)pyridin-3-yl]carbonyl}amino)propyl]phenyl}cyclohexanecarboxylate,
(3R)-1-azabicyclo[2.2.2]oct-3-yl 1-(3-{4-[{[2-chloro-4-({[2-hydroxy-2-(8-hydroxy-2-oxo-1,2-dihydroquinolin-5-yl)ethyl]amino}methyl)-5-methoxyphenoxy]acetyl}(methyl)amino]butyl}phenyl)cyclohexanecarboxylate,
(3R)-1-azabicyclo[2.2.2]oct-3-yl 1-[3-(4-{[5-({[(2R)-2-hydroxy-2-(8-hydroxy-2-oxo-1,2-dihydroquinolin-5-yl)ethyl]amino}methyl)-1,3-thiazol-2-yl]amino}-4-oxobutyl)phenyl]cyclohexanecarboxylate,
piperidin-4-ylmethyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate,
(1-methylpiperidin-4-yl)methyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate,
(3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenyl]glycyl}amino)propyl]phenyl}cyclohexanecarboxylate
(3R)-1-azabicyclo[2.2.2]oct-3-yl 1-[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate, and
(3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclopentanecarboxylate,
or a pharmaceutically acceptable salt, or N-oxide, or isotopically-labeled derivate thereof.

Of particular interest are the compounds:
(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}phenyl)cyclohexanecarboxylate,
(3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate,
(3R)-1-azabicyclo[2.2.2]oct-3-yl 1-[3-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)phenyl]cyclohexanecarboxylate,
(3R)-1-azabicyclo[2.2.2]oct-3-yl 1-[3-(4-{[2-chloro-4-({[(2R)-2-hydroxy-2-(8-hydroxy-2-oxo-1,2-dihydroqui-nolin-5-yl)ethyl]amino}methyl)-5-methoxybenzoyl]amino}butyl)phenyl]cyclohexanecarboxylate,
3-[3-(1-{[(3R)-1-azabicyclo[2.2.2]oct-3-yloxy]carbonyl}cyclohexyl)phenyl]propyl 2-chloro-4-({[(2R)-2-hydroxy-2-(8-hydroxy-2-oxo-1,2-dihydroquinolin-5-yl)ethyl]amino}methyl)-5-methoxybenzoate,
1-azabicyclo[2.2.2]oct-4-ylmethyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate,
(3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}amino)propyl]phenyl}cyclohexanecarboxylate,
(3R)-1-azabicyclo[2.2.2]oct-3-yl 1-[3-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl)phenyl]cyclohexanecarboxylate,
(3R)-1-azabicyclo[2.2.2]oct-3-yl 1-{3-[4-({[2-chloro-4-({[2-hydroxy-2-(8-hydroxy-2-oxo-1,2-dihydroquinolin-5-yl)ethyl]amino}methyl)-5-methoxyphenoxy]acetyl}amino)butyl]phenyl}cyclohexanecarboxylate,
(3R)-1-azabicyclo[2.2.2]oct-3-yl 1-(3-{4-({[2-chloro-4-({[2-hydroxy-2-(8-hydroxy-2-oxo-1,2-dihydroquinolin-5-yl)ethyl]amino}methyl)-5-methoxyphenoxy]acetyl}(methyl)amino]butyl}phenyl)cyclohexanecarboxylate,
piperidin-4-ylmethyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate,
(1-methylpiperidin-4-yl)methyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate, and
(3R)-1-azabicyclo[2.2.2]oct-3-yl 1-[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate,
or a pharmaceutically acceptable salt, or N-oxide, or isotopically-labeled derivate thereof.

The invention is also directed to a compound of the invention as described herein for use in the treatment of the human or animal body by therapy.

According to another embodiment the present invention covers pharmaceutical compositions comprising at least a compound of the invention, as herein above described, in admixture with pharmaceutically acceptable diluents or carriers.

In an embodiment of the present invention the pharmaceutical composition further comprises a therapeutically effective amount of one or more other therapeutic agents.

It is also an embodiment of the present invention that the pharmaceutical composition is formulated for administration by inhalation.

The compounds of the present invention as herein above defined may also be combined with one or more other therapeutic agents, for simultaneous, separate or sequential use in the treatment of the human or animal body.

The invention is also directed to compounds of the present invention for use in the treatment of a pathological condition or disease associated with both β2 adrenergic receptor and muscarinic receptor activities such as a pulmonary disease. In particular the pulmonary disease is asthma or chronic obstructive pulmonary disease.

The pathological condition or disease can also be applied within the scope of the present invention to the treatment of a disease or condition selected from the group consisting of pre-term labor, glaucoma, neurological disorders, cardiac disorders, and inflammation, urological disorders such as urinary incontinence and gastrointestinal disorders such as irritable bowel syndrome or spastic colitis.

The invention is also directed to the use of compounds of the present invention for the manufacture of a medicament for the treatment of pathological condition or disease associated with one or both β2 adrenergic receptor and muscarinic receptor activities such as a pulmonary disease, in particular asthma or chronic obstructive pulmonary disease, pre-term labor, glaucoma, neurological disorders, cardiac disorders, inflammation, urological disorders and gastrointestinal disorders, preferably, asthma and chronic obstructive pulmonary disease.

The invention is also directed to a method of treating these diseases, which comprises administering a therapeutically effective amount of a pharmaceutical composition comprising a dual β2 adrenergic receptor agonists and muscarinic receptor antagonists according to the present invention. The method further comprises administering a therapeutically effective amount of one or more other therapeutic agent.

The invention is also directed to a method of modulating the activity of a β2 adrenergic and/or a M3 receptor, the method comprising stimulating a β2 adrenergic receptor and/or blocking a M3 receptor with a modulatory amount of compounds of the present invention.

The term "therapeutically effective amount" refers to an amount sufficient to effect treatment when administered to a patient in need of treatment.

The term "treatment" as used herein refers to the treatment of a disease or medical condition in a human patient which includes:
(a) preventing the disease or medical condition from occurring, i.e., prophylactic treatment of a patient;
(b) ameliorating the disease or medical condition, i.e., causing regression of the disease or medical condition in a patient;
(c) suppressing the disease or medical condition, i.e., slowing the development of the disease or medical condition in a patient; or
(d) alleviating the symptoms of the disease or medical condition in a patient.

The phrase "disease or condition associated with β2 adrenergic receptor and muscarinic activities" includes all disease states and/or conditions that are acknowledged now, or that are found in the future, to be associated with both β2 adrenergic receptor and muscarinic receptor activity. Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

On the other hand M3 receptor activity is associated with gastrointestinal-tract disorders such as Irritable bowel syndrome (IBS) (see, for ex., U.S. Pat. No. 5,397,800), GI ulcers, spastic colitis (see, for ex., U.S. Pat. No. 4,556,653); urinary-tract disorders such as urinary incontinence (see, for ex., J. Med. Chem., 2005, 48, 6597-6606), pollakiuria; motion sickness and vagally induced sinus bradycardia.

General Synthetic Procedures

The compounds of the invention can be prepared using the methods and procedures described herein, or using similar methods and procedures. It will be appreciated that typical or preferred process conditions (i.e., reaction temperatures, times, mole ratios of reactants, solvents, pressures, etc.) are given. Other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

Processes for preparing compounds of the invention are provided as further embodiments of the invention and are illustrated by the procedures below.

One of the most convenient route for the preparation of compounds of formula (I) is depicted in Scheme 1.

Scheme 1

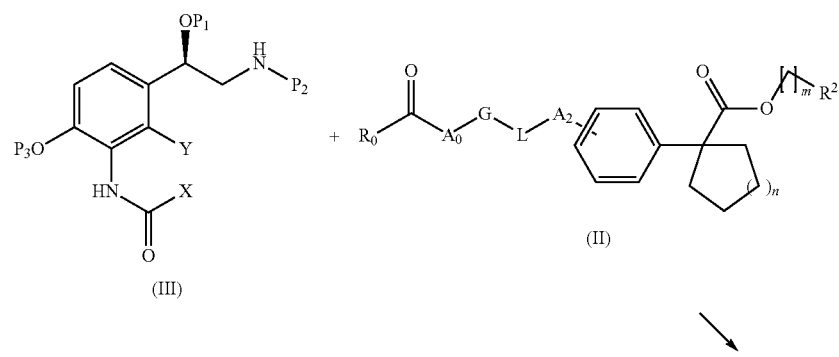

-continued

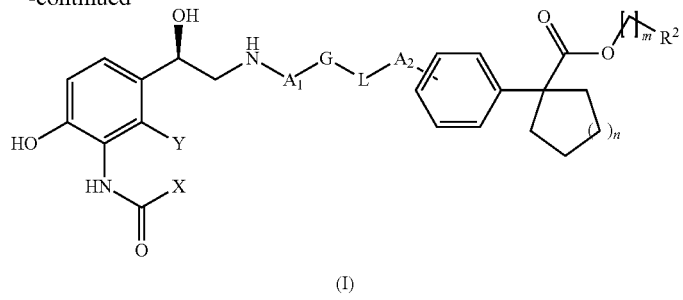

(I)

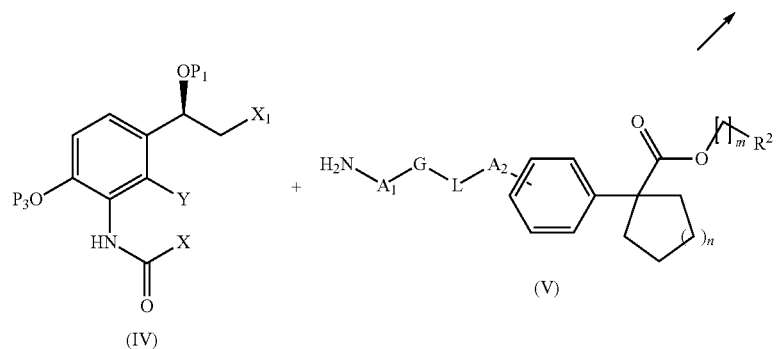

Compounds of formula (I) may be prepared by reacting intermediates of formula (II) wherein $A_0$ represents a group that together with the adjacent methylene newly formed affords the $A_1$ group, being $R_0$ hydrogen or lower alkyl group and $R^2$ and n are as defined above, with intermediates of formula (III) wherein $P_1$ and $P_3$ independently represent a hydrogen atom or a oxygen-protecting group such as a silyl or benzyl ether and $P_2$ represents a hydrogen atom or a nitrogen-protecting group such as for example a benzyl group. This reaction is best carried out in a solvent or mixture of solvents like THF, methanol, dichloromethane, dichloroethane or DMSO at a temperature between 0° C. and 60° C. using a hydride like sodium borohydride or sodium triacetoxyborohydride as reducing agent.

Alternatively, compounds of formula (I) may also be prepared by reacting intermediates of formula (V) with intermediates of formula (IV) wherein $X_1$ represents a leaving group such as a halogen atom, $P_1$ and $P_3$ have the same meaning as disclosed above, following the same synthetic procedure; and subsequently removing whichever protecting group present in the intermediate to provide a compound of formula (I). Such deprotection processes involve, for example, a desilylation process, by using triethylamine trihydrofluoride, TBAF, hydrogen chloride or other acidic reagents in an inert solvent like THF or dioxane, in a range of temperatures between 0° C. and 50° C. The deprotection could also be carried out by a debenzylation process, for example, by hydrogenating the compound in the presence of a catalyst such as palladium on charcoal in an inert solvent like ethanol or THF or a mixture of solvents. This reaction is typically carried out at a hydrogen pressure between 10 and 60 psi and in a range of temperatures between room temperature and 50° C.

Intermediates of formula (II) may be prepared, as depicted in Scheme 2, from bromoaryl derivatives (VI) and a suitable olefinic fragment (VII), where $A_3$ is defined as $A_2$ except from the terminal vinyl group, via a coupling reaction such as, for ex., a Heck reaction, carried out in the presence of a palladium salt, a phosphine ligand and a base, for ex., palladium acetate, tri-o-tolylphosphine and diisopropylethylamine in a solvent like acetonitrile or THF in a range of temperatures between room temperature and 120° C. Alternatively, Intermediates of formula (II) may be prepared from the corresponding hydroxyl derivatives (VIII) by oxidation with Dess-Martin periodinane or manganese dioxide in solvents such as chloroform or THF an temperatures ranging from ambient temperature to 50° C. Hydroxyl derivatives (VIII) can be prepared from their suitably protected hydroxides (IX), for example a silyl protected ($P_4$) hydroxide (IX) form by a deprotection reaction known to those skilled in the art, for example treatment with triethylamine trihydrofluoride, TBAF, hydrogen chloride or other acidic reagents in an inert solvent like THF or dioxane, in a range of temperatures between 0° C. and 50° C. Additionally, intermediates of formula (IX) can be prepared from bromoaryl derivatives (VI) and a suitable hydroxyl protected olefinic fragment (X), where $A_3$ is as defined above, and using the same coupling protocol as defined above.

Scheme 2

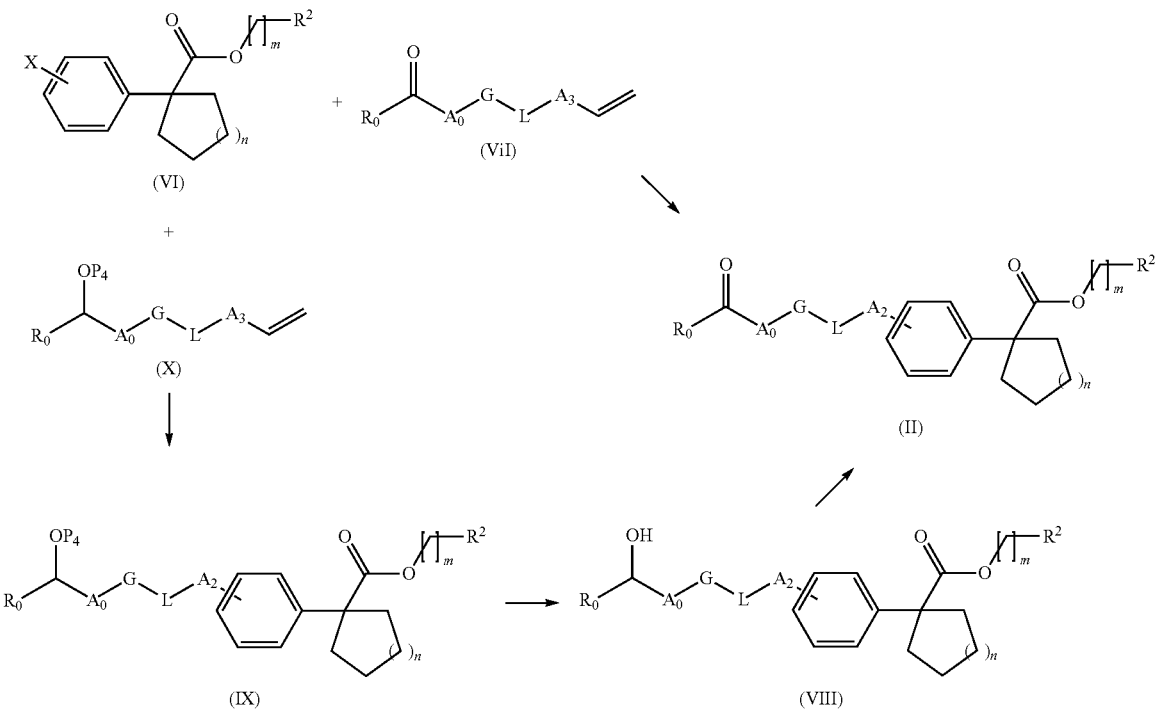

Additionally, following the synthetic sequence described in Scheme 3, intermediates of formula (IX) can be prepared by coupling the G-L bond at a later step, via an amide or ester bond between intermediates of formula (XI) where the terminal part of G (N) is a NHR (R=H or Me), COOH or OH group, and intermediates of formula (XII) where the terminal part of L (F) is a COOH or $NH_2$ group. In this formula (XI) can be prepared from a coupling reaction such as a Heck reaction between intermediates of formula (VI) and vinyl derivatives of formula (XIII) using the same coupling conditions described above followed by a hydrogenation reaction using standard procedures as described above.

Scheme 3.

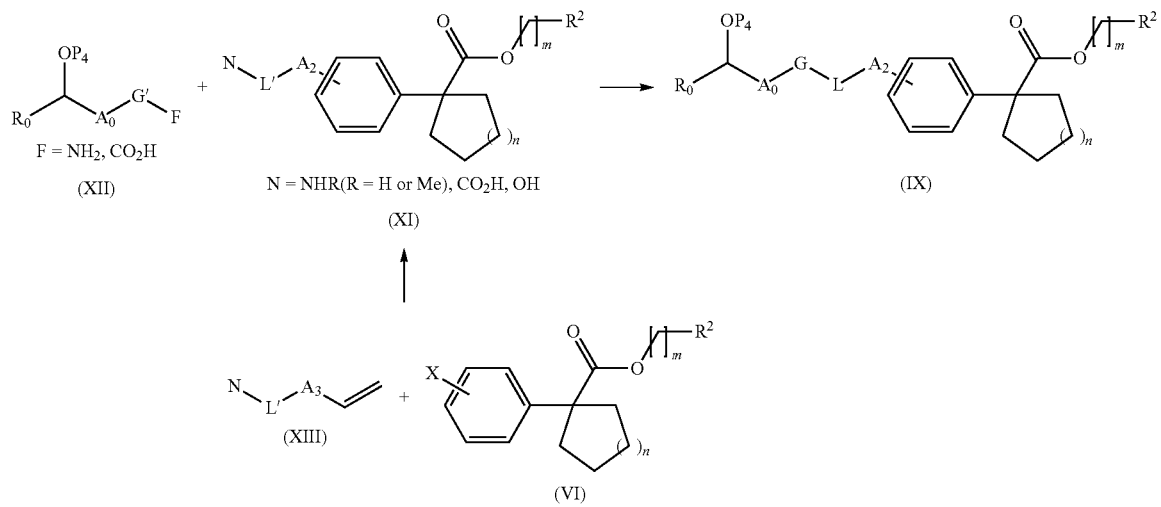

instance, amide and ester bond formation is carried out using common methods for those skilled in the art, with coupling reagents such as HATU, or via acid chloride derivatives and solvents such as chloroform, THF or DMF. Intermediates of In some instances, a more direct approach can be used to obtain intermediates of formula (II), as depicted in Scheme 4, by coupling the G-L bond via an amide or ester bond between intermediates of formula (XI) where the terminal part of G (N) is a NHR (R=H or Me), COOH or OH group, and intermediates of formula (XIV) where the terminal part of L is a COOH or NH2 group using the methodology described above.

Scheme 4.

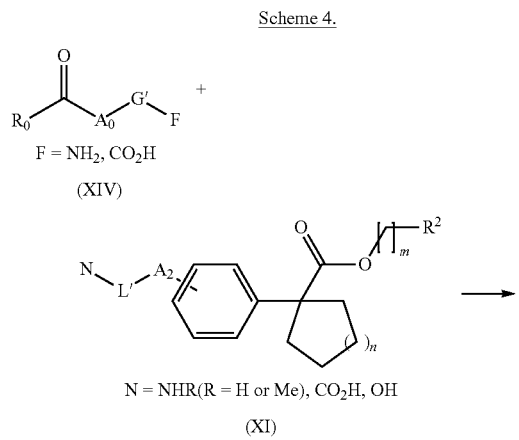

F = NH$_2$, CO$_2$H
(XIV)

N = NHR(R = H or Me), CO$_2$H, OH
(XI)

Finally, intermediates of formula (VI) from Schemes 2 and 3 can be prepared as depicted in Scheme 5, starting from known arylacetonitrile derivatives (XV) through initial conversion to α,α-disubstituted derivatives (XVI) using dihaloalkyl derivatives and a suitable base such as sodium hydride or lithium or sodium bis(trimethylsilyl)amide in a solvent such as THF or DMF, followed by hydrolysis of the cyano group to the corresponding carboxylic acid (XVII) in the presence of a base such as KOH and using solvents such as EtOH or ethylene glycol and temperatures ranging from 80 to 120° C.; or alternatively by using an acidic reagent as hydrobromic acid in a solvent such as acetic acid or mixtures of acetic acid and water at temperatures ranging from 50° C. to 120° C. Esterification reaction with the corresponding substituted alcohol (ROH) can be performed under basic conditions using a base such as sodium hydride, lithium or sodium bis(trimethylsilyl)amide, or butyl lithium and the acid chloride derivative or another suitable common activating reagent for those skilled in the art, using a mixture of solvents such as of THF and toluene.

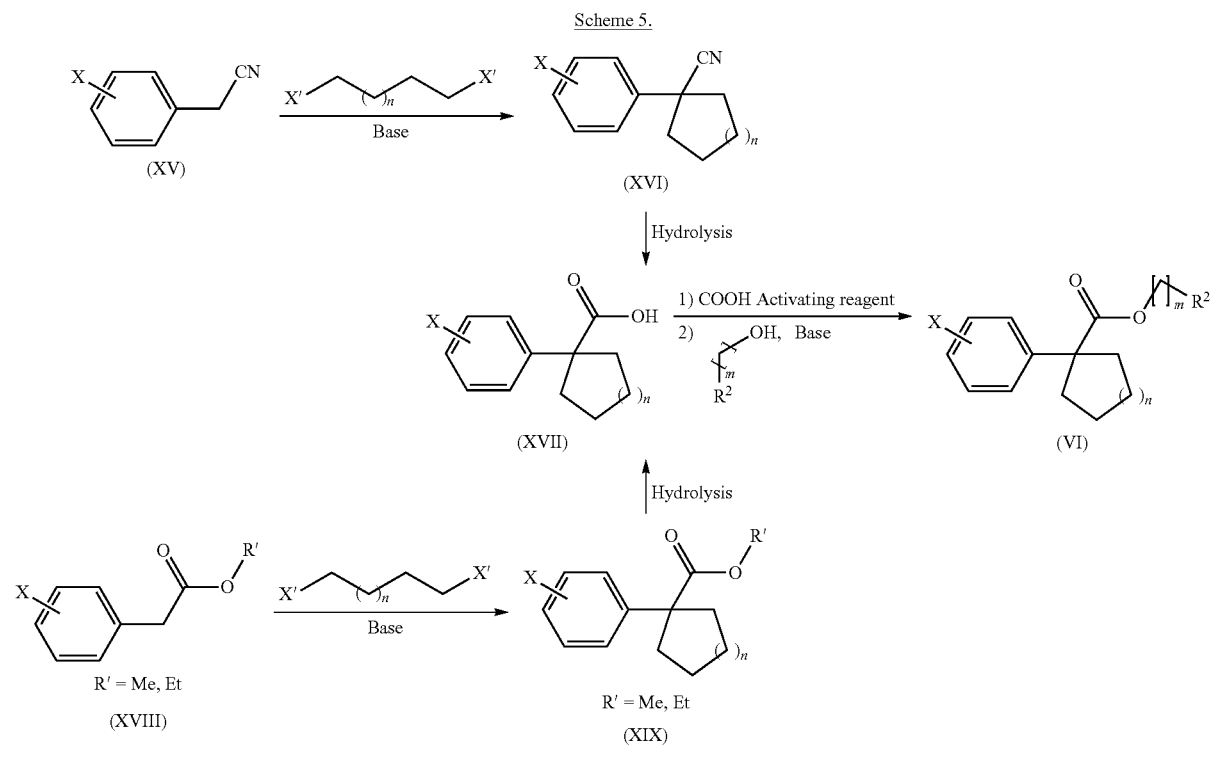

Moreover, carboxylic acid intermediates of formula (XVII) can be alternatively prepared from the corresponding esters (XIX) using common procedures for ester hydrolysis. These ester intermediates can be obtained from the corresponding known arylacetate esters (XVIII) using the same alkylation protocol as described above.

EXAMPLES

General. Reagents, starting materials, and solvents were purchased from commercial suppliers and used as received.

Concentration refers to evaporation under vacuum using a Büchi rotatory evaporator. Reaction products were purified, when necessary, by flash chromatography on silica gel (40-63 μm) with the solvent system indicated or using preparative HPLC conditions (see bellow description of two systems used). Spectroscopic data were recorded on a Varian Gemini 300 spectrometer. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector.

HPLC System 1:

C-18 reverse phase column silica from MERCK, water/acetonitrile (without buffer) as eluents using a gradient from 0% to 100%.

HPLC System 2:

C-18 reversed phase column silica from MERCK, water/acetonitrile as eluents [0.1% v/v ammonium formate buffered] using a gradient from 0% to 100%.

Intermediate 1

1-(3-bromophenyl)cyclohexanecarbonitrile

A solution of 2-(3-bromophenyl)acetonitrile (20 g, 0.1 mol) and 1,5-dibromopentane (14.4 mL, 0.11 mol) in THF (140 mL) was added dropwise, over a period of 1 hour and under inert atmosphere, over a refluxing suspension of sodium hydride (10.2 g, 0.26 mol of a 60% dispersion in oil) in THF (140 mL). The resulting reaction mixture was refluxed overnight and then allowed to cool down to ambient temperature. A mixture of ice and water was added to the reaction mixture and the organic solvent was evaporated. The remaining residue was dissolved in chloroform (250 mL) and the organic phase was washed with water (3×100 mL) and brine (100 mL), dried over anhydrous sodium sulphate, treated with active carbon, filtered and concentrated to dryness to afford the title compound as a colorless oil (27.5 g, 97%). The compound was used without any further purification.

1H NMR (300 MHz, cdcl3) δ 7.61 (t, J=1.9 Hz, 1H), 7.45 (ddd, J=7.9, 1.9, 1.0 Hz, 2H), 7.26 (t, J=7.9 Hz, 1H), 2.19-2.09 (m, 2H), 1.94-1.79 (m, 4H), 1.79-1.66 (m, 2H), 1.27 (m, 2H).

Intermediate 2

1-(3-bromophenyl)cyclohexanecarboxylic acid

To a suspension of 1-(3-bromophenyl)cyclohexanecarbonitrile (Intermediate 1, 18.4 g, 0.07 mol) in ethyleneglycol (202 mL) was added KOH (115 mL of a 10M aqueous solution, 16.5 mol) and the resulting mixture was stirred at 130° C. for 36 hours. Upon complete consumption of starting material, the reaction vessel was allowed to cool to r.t. and water was added (260 mL). The aqueous phase was washed with diethyl ether (3×200 mL) and the resulting aqueous phase was acidified with concentrated HCl until pH=3. The resulting white suspension was extracted with diethyl ether (5×150 mL), washed with brine, filtered and concentrated to dryness to afford the title compound as a white solid (18.2 g, 88%).

LRMS (m/z): 281/283 (M−1)−; 327/329 (M+45 [HCOO−])−

Intermediate 3

(3R)-1-azabicyclo[2.2.2]oct-3-yl 1-(3-bromophenyl) cyclohexanecarboxylate

A solution of 1-(3-bromophenyl)cyclohexanecarboxylic acid (Intermediate 2, 6.1 g, 21.5 mmol) in thionyl chloride (75 mL) was heated to 100° C. until formation of the intermediate acid chloride was completed (ca. 16 h). Then, the solvent was evaporated and the residue was treated with toluene and concentrated to dryness (this operation was performed two times). The solid residue obtained is dissolved in toluene (105 mL), and added dropwise, over a 0° C. preformed solution of (3R)-1-azabicyclo[2.2.2]octan-3-ol (previously dried with co-evaporations in toluene, 2.74 g, 21.5 mmol) and butyllithium (17.5 mL of a 1.6M solution in hexanes, 28.0 mmol) in THF (105 mL) and the reaction mixture was allowed to warm up to r.t. and stirring was continued at this temperature for 2 additional hours. Then, water was added and the organic solvents were removed under reduced pressure. The oily residue was diluted in toluene (ca. 100 mL) and 2N aqueous HCl was added obtaining a white solid which was filtered off. The phases were separated and the organic phase was further extracted with aqueous 2N HCl (3×50 mL). The combined aqueous extracts, together with the previously filtered solid, were basified with solid sodium carbonate until pH=12 and extracted with chloroform (3×150 mL). The combined organic phases were washed with water and brine, treated with active carbon, dried over anhydrous sodium sulphate and concentrated to dryness to obtain the title compound as a white solid (6.7 g, 79%).

LRMS (m/z): 392/394 (M/M+2)+

Intermediate 4

2-oxo-2,3-dihydro-1,3-benzoxazole-6-carbaldehyde

To a suspension of 6-bromobenzo[d]oxazol-2(3H)-one (6.12 g, 28.6 mmol) in THF (60 mL) was added, at −78° C. and under argon atmosphere, methylmagnesium bromide (10.6 mL of a 3M solution in diethyl ether, 31.8 mmol) and the reaction mixture was stirred at this temperature fro 30 min. The, an additional amount of THF (240 mL) was added at a rate that the internal temperature was below −50° C. Then, tert-butyllithium (60.6 mL of a 1.7 M solution in pentane, 103 mmol) was slowly added and stirred for 45 min at −78° C. To the yellow suspension DMF (13.4 mL, 181 mmol) was then added, and the reaction mixtures was allowed to warm up to room temperature and stirring was continued for 3 additional hours. Water (300 mL) was then added to the crude mixture and the organic solvent was removed under reduced pressure. To the remaining aqueous phase, ethyl acetate (500 mL) and 1N HCl (150 mL) were added and the mixture was vigorously stirred and the organic phase was separated. The aqueous phase was further extracted with ethyl acetate (3×100 mL) and the combined organic extracts were washed with water, brine, dried over anhydrous sodium sulphate, filtered and concentrated under reduced pressure to yield the title compound (4.75 g, 96%, 94% purity by UPLC). The compound was used as this without further purification.

LRMS (m/z): 162 (M−1)−

Intermediate 5

3-but-3-en-1-yl-2-oxo-2,3-dihydro-1,3-benzoxazole-6-carbaldehyde 2-oxo-2,3-dihydro-1,3-benzoxazole-6-carbaldehyde (Intermediate 4, 2.0 g, 12.3 mmol), 4-bromo-1-butene (6.2 mL, 61.1 mmol) and potassium carbonate (1.7 g, 12.3 mmol) were suspended in DMF (14 mL) in a high pressure reaction vessel. The mixture was heated at 75° C. for 16 h. The solids were filtered, washed with dichloromethane and the filtrate was concentrated under vacuum. To solid residue obtained was purified by column chromatography over silica gel eluting with Hexane/Diethyl Ether (from 0 to 100% of Et2O) to yield the title compound as a brownish solid (2.0 g, 75%).

LRMS (m/z): 218 (M+1)+

Intermediate 6

(3R)-1-azabicyclo[2.2.2]oct-3-yl 1-{3-[(1E)-4-(6-formyl-2-oxo-1,3-benzoxazol-3(2H)-yl)but-1-en-1-yl]phenyl}cyclohexanecarboxylate To a suspension of (3R)-1-azabicyclo[2.2.2]oct-3-yl 1-(3-bromophenyl)cyclohexane carboxylate (Intermediate 3, 400 mg, 1.02 mmol) in acetonitrile (4 mL) were sequentially added 3-but-3-en-1-yl-2-oxo-2,3-dihydro-1,3-benzoxazole-6-carbaldehyde (Intermediate 5, 264 mg, 1.19 mmol), tri-ortho-tolylphosphine (312 mg, 1.02 mmol), DIEA (356 µL, 2.04 mmol) and palladium acetate (116 mg, 0.52 mmol). The flask was purged with nitrogen two times and the reaction mixture was heated to 90° C. for 45 min. The reaction mixture was then filtered and the filtrate was concentrated to dryness. To residue obtained was purified by column chromatography over silica gel eluting with Chloroform/Methanol (from 0 to 10% of Methanol) to afford the title compound as an orange oil (458 mg, 65%).

LRMS (m/z): 529 (M+1)+

Intermediate 7

(3R)-1-azabicyclo[2.2.2]oct-3-yl 1-{3-[4-(6-formyl-2-oxo-1,3-benzoxazol-3(2H)-yl)butyl]phenyl}cyclohexanecarboxylate To a solution of (3R)-1-azabicyclo[2.2.2]oct-3-yl 1-{3-[(1E)-4-(6-formyl-2-oxo-1,3-benzoxazol-3(2H)-yl)but-1-en-1-yl]phenyl}cyclohexanecarboxylate (Intermediate 6, 450 mg, 0.85 mmol) in acetic acid (10 mL) was added palladium on carbon (92 mg of a 10% by weight, 0.09 mmol) and the reaction mixtures was stirred under hydrogen atmosphere for 2 hours. The mixture was filtered through a 4µ PTFE membrane filter and the filtrate was concentrated to dryness. The obtained residue was dissolved in chloroform (20 mL) and 4% aqueous sodium bicarbonate (20 mL) was added. The phases were separated and the organic phase was washed with brine (15 mL), dried, filtered and concentrated under vacuum. The crude residue was further purified by column chromatography over silica gel eluting with Chloroform/Methanol (from 0 to 10% of Methanol) to afford the title compound as an light yellow oil (199 mg, 41%).

LRMS (m/z): 531 (M+1)+

Intermediate 8

(3R)-1-azabicyclo[2.2.2]oct-3-yl 1-(3-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]butyl}phenyl)cyclohexanecarboxylate To a solution of (3R)-1-azabicyclo[2.2.2]oct-3-yl 1-{3-[4-(6-formyl-2-oxo-1,3-benzoxazol-3(2H)-yl)butyl] phenyl}cyclohexanecarboxylate (Intermediate 7, 188 mg, 0.35 mmol) in a mixture of methanol (2 mL) and THF (1 mL) was added, under nitrogen atmosphere, 5-((1R)-2-amino-1-{[tert-butyl(dimethyl)-silyl]oxy}ethyl)-8-hydroxyquinolin-2(1H)-one acetate (prepared according to preparation 8 from US20060035931, 140 mg, 0.35 mmol) and the reaction mixtures was stirred for 3 h at room temperature. To this solution, sodium triacetoxyborohydride (283 mg, 1.34 mmol) was added at 0° C. portionwise. After the addition was complete, the mixtures was stirred at 0° C. for 5 min and allowed to stir to r.t. overnight. 4% aqueous sodium bicarbonate was slowly added to the mixture (20 mL) and then ethyl acetate was added and the phases separated. The aqueous phase was further extracted with ethyl acetate (2×20 mL) and the combined organic extracts were washed with 4% aqueous bicarbonate solution (20 mL), water and brine (20 mL each), dried and concentrated to dryness. The yellow oily residue obtained was further purified by column chromatography over silica gel using a gradient of eluents Chloroform/Methanol (from 0 to 100% of Methanol) to afford the title compound as a light yellow oil (234 mg of a 73% purity, 41%).

LRMS (m/z): 850 (M+1)+

Example 1

(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}phenyl)cyclohexanecarboxylate To a solution of (3R)-1-azabicyclo[2.2.2]oct-3-yl 1-(3-{4-[6-({[(2R)-2-{[tert-butyl(dimethyl)silyl]oxy}-2-(8-hydroxy-2-oxo-1,2-dihydroquinolin-5-yl)ethyl] amino}methyl)-2-oxo-1,3-benzoxazol-3(2H)-yl] butyl}phenyl)cyclohexanecarboxylate (Intermediate 8, 234 mg of a 73% purity, 0.27 mmol) in THF (9 mL) was added, under nitrogen atmosphere, triethylamine trihydrofluoride (225 µL, 1.38 mmol). The mixture was stirred overnight at room temperature. The solvent was removed and the residue was treated with acetonitrile giving a solid that was filtered and further washed with acetonitrile (3 times) and diethyl ether (3 times). The obtained solid was purified by column chromatography over silica gel using a gradient of eluents Chloroform and Chloroform/Methanol/ammonia (80:20:2) to afford the title compound as a yellow solid (74 mg, 46%).

LRMS (m/z): 736 (M+1)+

1H NMR (300 MHz, dmso) δ 10.42 (br s, 1H), 8.17 (d, 1H), 7.43 (s, 1H), 7.32-7.15 (m, 4H), 7.12-7.08 (m, 2H), 6.96 (d, 1H), 6.52 (d, 1H), 5.21 (t, 1H), 4.81-4.66 (m, 1H), 3.95 (s, 1H), 3.86 (t, 2H), 3.15 (ddd, 2H), 2.79 (d, 1H), 2.75-2.58 (m, 3H), 2.44-2.31 (m, 2H), 1.84-1.82 (m, 1H), 1.78-1.51 (m, 8H), 1.51-1.34 (m, 3H), 1.34-1.19 (m, 2H).

Intermediate 9

(3R)-1-azabicyclo[2.2.2]oct-3-yl 1-{3-[(1E)-4-tert-butoxy-4-oxobut-1-en-1-yl]phenyl}cyclohexanecarboxylate Obtained as a colorless foam (2.86 g, 100%) from (3R)-1-azabicyclo[2.2.2]oct-3-yl 1-(3-bromophenyl)cyclohexane carboxylate (Intermediate 3, 2.0 g, 5.1 mmol), tert-butyl but-3-enoate (0.87 mL, 5.38 mmol), tri-ortho-tolylphosphine (620 mg, 2.04 mmol), DIEA (1.61 mL, 9.2 mmol) and palladium acetate (230 mg, 1.02 mmol) in acetonitrile (18.6 mL), following the experimental procedure described for the synthesis of Intermediate 6. Purification of the crude residue was performed by column chromatography over silica gel using a gradient of eluents Hexane:Chloroform:Methanol.
LRMS (m/z): 454 (M+1)+

Intermediate 10

(3R)-1-azabicyclo[2.2.2]oct-3-yl 1-[3-(4-tert-butoxy-4-oxobutyl)phenyl]cyclo hexanecarboxylate Obtained as a brownish foam (4 g of a 92% purity, acetate salt, 100%) from (3R)-1-azabicyclo[2.2.2]oct-3-yl 1-{3-[(1E)-4-tert-butoxy-4-oxobut-1-en-1-yl]phenyl}cyclohexane carboxylate (Intermediate 9, 2.86 g, 6.3 mmol) and palladium on carbon (1.22 g of a 10% by weight, 0.115 mmol) in a mixture of acetic acid (25 mL) and THF (25 mL), following the experimental procedure described for the synthesis of Intermediate 7. The crude product was used without any further purification.
LRMS (m/z): 456 (M+1)+

Intermediate 11

4-[3-(1-{[(3R)-1-azabicyclo[2.2.2]oct-3-yloxy]carbonyl}cyclohexyl)phenyl]butanoic acid To a solution of (3R)-1-azabicyclo[2.2.2]oct-3-yl 1-[3-(4-tert-butoxy-4-oxobutyl)phenyl]cyclohexanecarboxylate (Intermediate 10, 3.25 g, 6.3 mmol) in chloroform (36 mL) was added, under argon atmosphere, trifluoroacetic acid (4.9 mL, 63.6 mmol) and the reaction mixture was stirred at room temperature overnight. The solvent is removed under reduced pressure and the residue was redissolved in chloroform (20 mL) and evaporated to dryness again (procedure performed 2 times). The residue was dissolved again in chloroform (30 mL) and active carbon was added to the solution. The suspension was filtered and evaporated to dryness to afford the title compound (2.88 g as a TFA salt, 86%) as a colorless gum. The compound was used without further purification.
LRMS (m/z): 400 (M+1)+

Intermediate 12

(3R)-1-azabicyclo[2.2.2]oct-3-yl 1-[3-(4-{[4-({[tert-butyl(dimethyl)silyl]oxy}methyl)-2-chloro-5-methoxyphenyl]amino}-4-oxobutyl)phenyl]cyclohexanecarboxylate To a solution of 4-[3-(1-{[(3R)-1-azabicyclo[2.2.2]oct-3-yloxy]carbonyl}cyclohexyl)phenyl]butanoic acid (Intermediate 11, 843 mg of the TFA salt, 1.64 mmol) in chloroform (9.6 mL) was added DIEA (0.98 mL, 5.58 mmol) and the reaction mixture was stirred at rt for 5 min. Then, 4-((tert-butyldimethylsilyloxy)methyl)-2-chloro-5-methoxyaniline (prepared according to experimental procedure described in patent WO201114180 for the synthesis of Intermediate 39, 430 mg, 1.42 mmol) was added followed by stepwise addition of HATU (613 mg, 1.61 mmol). Stirring was maintained, under nitrogen atmosphere, for 18 hours. The reaction mixture was diluted with chloroform and the organic phase was washed with 4% aqueous sodium bicarbonate solution (2×20 mL), water and brine (20 mL each), dried, filtered and concentrated under reduced pressure obtaining a brownish oil. The oil obtained was purified by column chromatography over silica gel using a gradient of eluents Hexane:Chloroform:Methanol to yield the title compound (646 mg, 74%) as a colorless oil.
LRMS (m/z): 684 (M+1)+

Intermediate 13

(3R)-1-azabicyclo[2.2.2]oct-3-yl 1-[3-(4-{[2-chloro-4-(hydroxymethyl)-5-methoxyphenyl]amino}-4-oxobutyl)phenyl]cyclohexanecarboxylate To a solution of (3R)-1-azabicyclo[2.2.2]oct-3-yl 1-[3-(4-{[4-({[tert-butyl(dimethyl)silyl]oxy}methyl)-2-chloro-5-methoxyphenyl]amino}-4-oxobutyl)phenyl]cyclohexane carboxylate (Intermediate 12, 640 mg, 0.94 mmol) in THF (18 mL) was added, under nitrogen atmosphere, the complex triethylamine trihydrofluoride (0.58 mL, 3.57 mmol) and the resulting solution was stirred at rt overnight. The THF was then removed under vacuum and the residue was dissolved in chloroform and 4% aqueous sodium bicarbonate was added. The biphasic mixture was vigorously stirred for 30 min and the organic phase was separated. The aqueous phase was further extracted with chloroform (2×30 mL) and the combined organic extracts were washed with water and brine (30 mL each), dried over anhydrous sodium sulphate, filtered and concentrated to dryness. The crude residue was purified by column chromatography over silica gel using a gradient of Chloroform/Methanol 25/1 to Chloroform/Methanol 15/1 in order to give the title compound (433 mg, 80%) as a colorless viscous oil.
LRMS (m/z): 569 (M+1)+

Intermediate 14

(3R)-1-azabicyclo[2.2.2]oct-3-yl 1-(3-{4-[(2-chloro-4-formyl-5-methoxyphenyl)amino]-4-oxobutyl}phenyl)cyclohexanecarboxylate (3R)-1-azabicyclo[2.2.2]oct-3-yl 1-[3-(4-{[2-chloro-4-(hydroxymethyl)-5-methoxyphenyl]amino}-4-oxobutyl)phenyl]cyclohexanecarboxylate (Intermediate 13, 433 mg, 0.76 mmol) was dissolved in chloroform (10 mL) and Dess-Martin periodinane reagent was added (403 mg, 1.25 mmol). The reaction mixture was placed under nitrogen atmosphere and was stirred for 3 hours. The reaction mixture was further diluted with chloroform (20 mL) and the organic phase was washed with 4% aqueous sodium bicarbonate (30 mL), water and brine (20 mL each), dried, filtered and concentrated under reduced pressure. The solid obtained was purified by column chromatography over silica gel using a gradient of Chloroform/Methanol 50/1 to Chloroform/Methanol 25/1 to Chloroform/Methanol 15/1 to provide the title compound (377 mg, 80%) as a colorless oil.
LRMS (m/z): 567 (M+1)+

Intermediate 15

(3R)-1-azabicyclo[2.2.2]oct-3-yl 1-[3-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl]cyclohexanecarboxylate Obtained as a yellow foam (421 mg of an 85% purity, 64%) from (3R)-1-azabicyclo[2.2.2]oct-3-yl 1-(3-{4-[(2-chloro-4-formyl-5-methoxyphenyl)amino]-4-oxobutyl}phenyl)cyclohexanecarboxylate (Intermediate 14, 362 mg, 0.64 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 250 mg, 0.63 mmol) and sodium triacetoxyborohydride (509 mg, 2.40 mmol) following the experimental procedure described for the synthesis of Intermediate 8, but using chloroform as organic solvent for the extraction step. Purification of the obtained residue was performed by column chromatography over silica gel using a gradient of Chloroform/Methanol going from 50/1 to 4/1.

LRMS (m/z): 886 (M+1)+; 884 (M−1)−

Example 2

(3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate Obtained as a white solid (277 mg as a dihydrofluoride salt, 70%) from (3R)-1-azabicyclo[2.2.2]oct-3-yl 1-[3-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl]cyclohexanecarboxylate (Intermediate 15, 417 mg, 0.47 mmol) and triethylamine trihydrofluoride (382 µL, 2.35 mmol) following the experimental procedure described for the synthesis of Example 1. In this instance no purification by column chromatography was required.

LRMS (m/z): 772 (M+1)+

1H NMR (300 MHz, dmso) δ 9.46 (br s, 1H), 8.16 (d, 1H), 7.43-7.20 (m, 4H), 7.15 (dd, 1H), 7.09 (d, 1H), 6.94 (d, 1H), 6.52 (d, 1H), 5.09 (dd, 1H), 4.77-4.67 (m, 1H), 3.77 (s, 3H), 3.73 (s, 1H), 3.09 (dd, 2H), 2.67 (m, 6H), 2.48-2.34 (m, 4H), 1.96-1.82 (m, 3H), 1.81-1.36 (m, 10H), 1.31-1.21 (m, 3H).

Intermediate 16 ethyl trans-4-aminocyclohexanecarboxylate

Concentrated hydrogen chloride (7 mL) was added to a suspension of (1r,4r)-4-aminocyclohexanecarboxylic acid hydrochloride (6.32 g, 0.035 mol) in ethanol (100 mL) and the mixture was stirred and heated to 60° C. and left overnight. The mixture was evaporated in vacuum, azeotroped the remaining water with further ethanol and finally toluene to give the title product as a white solid (7.2 g, 98%).

1H NMR (300 MHz, dmso) δ 4.05 (q, J=7.1 Hz, 2H), 2.95 (bs, 1H), 2.30-2.15 (m, 1H), 2.02-1.88 (m, 4H), 1.43-1.28 (m, 4H), 1.22-1.13 (t, J=6.9 Hz, 3H).

Intermediate 17

(trans-4-aminocyclohexyl)methanol

A suspension of ethyl trans-4-aminocyclohexanecarboxylate (Intermediate 16; 7.2 g, 0.034 mol) in THF (200 mL) was added to lithium aluminium hydride (69 mL of a 1M solution in THF, 0.069 mmol) at 0° C., and stirred 1 h at this temperature. The ice bath was then removed and the mixture was stirred at room temperature overnight. The stirred mixture was cooled in an ice bath and very carefully water (6.9 mL), 15% NaOH (21 mL) and water (21 mL) were added slowly. After stirring 30 minutes at room temperature the mixture was filtered through a thin layer (1 cm) of Celite and the filter cake was washed with THF. The combined filtrate and washings were evaporated to give a white solid as the title compound (4.4 g, 99%).

1H NMR (300 MHz, dmso) δ 3.18 (d, J=6.3 Hz, 2H), 2.42 (m, 1H), 1.79-1.60 (m, 4H), 1.30-1.13 (m, 1H), 1.05-0.72 (m, 4H).

Intermediate 18

(3R)-1-azabicyclo[2.2.2]oct-3-yl 1-[3-(4-{[trans-4-(hydroxymethyl)cyclohexyl]amino}-4-oxobutyl) phenyl]cyclohexanecarboxylate Obtained as a yellowish oil (166 mg of a 91% purity, 80%) from 4-[3-(1-{[(3R)-1-azabicyclo[2.2.2]oct-3-yloxy]carbonyl}cyclohexyl)phenyl]butanoic acid (Intermediate 11, 190 mg of the TFA salt, 0.37 mmol), (trans-4-aminocyclohexyl)methanol (Intermediate 17, 53 mg, 0.41 mmol), DIEA (0.29 mL, 1.67 mmol) and HATU (183 mg, 0.48 mmol) following the experimental procedure described for the synthesis of Intermediate 12. Purification of the crude residue was performed by column chromatography over silica gel using a gradient of Chloroform/Methanol going from 50/1 to 4/1.

LRMS (m/z): 512 (M+1)+

Intermediate 19

(3R)-1-azabicyclo[2.2.2]oct-3-yl 1-(3-{4-[(trans-4-formylcyclohexyl)amino]-4-oxobutyl}phenyl)cyclohexanecarboxylate Obtained as a yellow foam (162 mg of a 70% purity, 74%) from (3R)-1-azabicyclo[2.2.2]oct-3-yl 1-[3-(4-{[trans-4-(hydroxymethyl)cyclohexyl]amino}-4-oxobutyl)phenyl]cyclohexanecarboxylate (Intermediate 18, 155 mg, 0.3 mmol) and Dess-Martin periodinane reagent (161 mg, 0.38 mmol) following the experimental procedure described for the synthesis of Intermediate 14. The crude residue was purified by column chromatography over silica gel using a gradient of Chloroform/Methanol going from 50/1 to 4/1.

LRMS (m/z): 510 (M+1)+

Intermediate 20

(3R)-1-azabicyclo[2.2.2]oct-3-yl 1-[3-(4-{[trans-4-({[(2R)-2-{[tert-butyl(dimethyl) silyl]oxy}-2-(8-hydroxy-2-oxo-1,2-dihydroquinolin-5-yl)ethyl] amino}methyl)cyclohexyl]amino}-4-oxobutyl)phenyl]cyclohexane carboxylate Obtained as a yellowish foam (98 mg of an 80% purity, 43%) from (3R)-1-azabicyclo[2.2.2]oct-3-yl 1-(3-{4-[(trans-4-formylcyclohexyl)amino]-4-oxobutyl}phenyl)cyclohexanecarboxylate (Intermediate 19, 162 mg of a 70% purity, 0.22 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 88 mg, 0.22 mmol) and sodium triacetoxyborohydride (178 mg, 0.84 mmol) following the experimental procedure described for the synthesis of Intermediate 15. The crude residue was purified by column chromatography over silica gel using a gradient of Chloroform/Methanol going from 50/1 to 4/1.

LRMS (m/z): 828 (M+1)+

Example 3

(3R)-1-azabicyclo[2.2.2]oct-3-yl 1-[3-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)phenyl]cyclohexanecarboxylate Obtained as a light yellow solid (57 mg as a dihydrofluoride salt, 76%) from (3R)-1-azabicyclo[2.2.2]oct-3-yl 1-[3-(4-{[trans-4-({[(2R)-2-{[tert-butyl(dimethyl)silyl]oxy}-2-(8-hydroxy-2-oxo-1,2-dihydroquinolin-5-yl)ethyl]amino}methyl)cyclohexyl]amino}-4-oxobutyl)phenyl]cyclohexanecarboxylate (Intermediate 20, 98 mg of an 80% purity, 0.12 mmol) and triethylamine trihydrofluoride (96 µL, 0.59 mmol) following the experimental procedure described for the synthesis of Example 1. In this instance no purification by column chromatography was required.

LRMS (m/z): 714 (M+1)+

1H NMR (300 MHz, dmso) δ 8.16 (d, 1H), 7.66 (d, 1H), 7.29-7.15 (m, 2H), 7.11-7.04 (m, 2H), 6.94 (d, 1H), 6.54 (d, 1H), 5.13 (t, 1H), 4.73-4.58 (m, 1H), 3.08-3.01 (m, 1H), 2.78 (d, 2H), 2.65-2.22 (m, 11H), 2.02 (m, 2H), 1.79-1.20 (m, 14H), 0.96 (m, 2H)

Intermediate 21 tert-butyl allyl(methyl)carbamate

To a solution of N-methylprop-2-en-1-amine (1 g, 14.1 mmol) in dichloromethane (10 mL) was added triethylamine (2.35 mL, 16.9 mmol) and at 0° C. was added di-tert-butyl dicarbonate (3.06 g, 14.1 mmol) in portions. The reaction mixture was stirred 10 minutes at 0° C. and overnight at room temperature. The crude was partitioned between ethyl acetate and water (100 mL each), and the organic layer was washed with saturated ammonium chloride solution and brine (60 mL each). The organics were dried, filtered and the solvent was removed under reduced pressure giving the title compound as an oil (1.92 g, 80%).

Intermediate 22

(3R)-1-azabicyclo[2.2.2]oct-3-yl 1-(3-{(1E)-3-[(tert-butoxycarbonyl)(methyl)amino]prop-1-en-1-yl}phenyl)cyclohexanecarboxylate Obtained as a brownish foam (1.18 g, 89%) from (3R)-1-azabicyclo[2.2.2]oct-3-yl 1-(3-bromophenyl)cyclohexanecarboxylate (Intermediate 3, 1.01 g, 2.6 mmol), tert-butyl allyl(methyl)carbamate (Intermediate 21, 466 mg, 2.72 mmol), tri-ortho-tolylphosphine (792 mg, 2.6 mmol), DIEA (0.81 mL, 4.65 mmol) and palladium acetate (345 mg, 1.54 mmol), following the experimental procedure described for the synthesis of Intermediate 6. Purification of the crude residue was performed by column chromatography over silica gel using as a gradient a mixture of eluents Hexane:Chloroform:Methanol.

LRMS (m/z): 483 (M+1)+

Intermediate 23

(3R)-1-azabicyclo[2.2.2]oct-3-yl 1-(3-{3-[(tert-butoxycarbonyl)(methyl)amino]propyl}phenyl)cyclohexanecarboxylate Obtained as a colorless oil (518 mg of an 86% purity, acetate salt, 75%) from (3R)-1-azabicyclo[2.2.2]oct-3-yl 1-(3-{(1E)-3-[(tert-butoxycarbonyl)(methyl)amino]prop-1-en-1-yl}phenyl)cyclohexanecarboxylate (Intermediate 22, 589 mg, 1.22 mmol) and palladium on carbon (154 mg of a 10% by weight, 0.144 mmol) in acetic acid (14 mL), following the experimental procedure described for the synthesis of Intermediate 7. The crude product was purified by column chromatography over silica gel using a gradient of Chloroform:Methanol as eluent.

LRMS (m/z): 485 (M+1)+

Intermediate 24

(3R)-1-azabicyclo[2.2.2]oct-3-yl 1-{3-[3-(methylamino)propyl]phenyl}cyclohexane carboxylate To a solution of (3R)-1-azabicyclo[2.2.2]oct-3-yl 1-(3-{3-[(tert-butoxycarbonyl)(methyl)amino]propyl}phenyl)cyclohexanecarboxylate (Intermediate 23, 596 mg, 1.23 mmol) in chloroform (22 mL) was added, under nitrogen atmosphere, hydrochloric acid (1.85 mL of a 4M solution in Dioxane, 7.4 mmol) and the reaction mixture was allowed to stir at rt for 18 hours. The mixture was diluted with chloroform (30 mL) and washed with 4% aqueous sodium bicarbonate (50 mL). The aqueous phase was further extracted with chloroform (2×50 mL) and the combined organic extracts were washed with brine (50 mL), filtered and concentrated to dryness to yield the title compound as a yellowish solid (448 mg, 65%).

LRMS (m/z): 386 (M+1)+

Intermediate 25

Methyl 4-(benzyloxy)-2-hydroxybenzoate

To a stirred solution of methyl 2,4-dihydroxybenzoate (10 g, 59.5 mmol) in acetone (240 mL) was added potassium carbonate (9.0 g, 65.12 mmol) and the reaction mixture was placed under argon atmosphere. After 1 hour, sodium iodide (0.89 g, 5.94 mmol) and benzyl bromide (7.8 mL, 65.67 mmol) were added and the reaction mixture was heated to 80° C. for 4 hours. Then, dichloromethane (150 mL) was added and the organic phase was washed with water (2×100 mL), brine (100 mL), dried over sodium sulphate, filtered and concentrated to dryness to afford the title compound as a colorless oil (16.4 g of an 83% purity, 89%). The compound was used without any further purification.

LRMS (m/z): 257 (M−1)−

Intermediate 26

Methyl 4-(benzyloxy)-2-methoxybenzoate

Methyl 4-(benzyloxy)-2-hydroxybenzoate (Intermediate 25, 16.4 g, 63.4 mmol) was dissolved in acetone (40 mL) and potassium carbonate (10.3 g, 74.8 mmol), sodium iodide (0.86 g, 5.74 mmol) and dimethyl sulphate (7.55 mL, 79.8 mmol) were added to the reaction mixture under argon atmosphere. The mixture was heated to 80° C. for a period of 8 hours and then, the solvent was removed under reduced pressure. The residue was diluted with dichloromethane (150 mL) and the organic phase was washed with water (2×50 mL), brine (50 mL), dried over anhydrous sodium sulphate, filtered and concentrated under vacuum to provide the title compound as a colorless oil (16.8 g of an 84% purity, 99%).

LRMS (m/z): 273 (M+1)+

Intermediate 27

Methyl 4-hydroxy-2-methoxybenzoate

To a 60° C. preheated solution of methyl 4-(benzyloxy)-2-methoxybenzoate (Intermediate 26, 16.8 g, 61.8 mmol) in a mixture of THF (60 mL) and methanol (60 mL) was added palladium hydroxide on carbon (500 mg of a 20% weight loading, 3.56 mmol) and the reaction mixture was placed under hydrogen atmosphere at 45 psi for 24 hours. The reaction mixture was then filtered and the filtrate was concentrated to dryness. The crude residue was purified by column chromatography over silica gel using a gradient of dichloromethane and dichloromethane/methanol (9/1) to afford the title compound as a colorless oil (10.1 g, 85%).

LRMS (m/z): 183 (M+1)+; 181 (M−1)−

Intermediate 28

Methyl 5-chloro-4-hydroxy-2-methoxybenzoate

A suspension of methyl 4-hydroxy-2-methoxybenzoate (Intermediate 27, 10.0 g, 54.9 mmol) in acetic acid (57 mL) was heated to 70° C. until a clear solution was obtained. The reaction mixture was then allowed to cool to 35° C. and N-chlorosuccinimide (7.65 g, 57.3 mmol) was added. The mixture was heated at 55° C. and the reaction mixture was vigorously stirred at this temperature until the next day. The reaction mixture was allowed to cool to rt and water was added (570 mL). The suspension was filtered and the filter cake was washed with water. The solid obtained was redissolved in ethyl acetate (1.1 L) and the organic phase was washed with water (2×130 mL), brine (130 mL), dried over anhydrous sodium sulphate, filtered and concentrated in vacuo. The residue was then suspended in diethyl ether, filtered and the precipitate was dried obtaining the title compound as a white solid (8.9 g, 79%).

LRMS (m/z): 217 (M+1)+; 215 (M−1)−

Intermediate 29

2-chloro-4-(hydroxymethyl)-5-methoxyphenol

To a solution of methyl 5-chloro-4-hydroxy-2-methoxybenzoate (Intermediate 28; 2.5 g, 11.5 mmol) in THF (30 mL) was added dropwise at 0° C. lithium aluminium hydride (1 M in THF, 23.1 mL, 23.1 mmol). The reaction mixture was stirred 10 minutes at 0° C. and 2 hours at room temperature. The mixture was cooled at 0° C. and a saturated solution of sodium-potassium L-tartrate (100 mL) was added cautiously. Then Ethyl acetate was added and the mixture was stirred for 1 hour at room temperature. The organic layer was separated, dried, filtered and the solvent was removed under reduced pressure to give a crude, which was purified over silica gel eluting with Chloroform/Ethanol (100/0 to 0/100) to give the title compound as a foam (1.68 g, 69%).

LRMS (m/z): 171 (M-OH[tropilium cation])+; 187 (M−1)−

Intermediate 30 tert-butyl [2-chloro-4-(hydroxymethyl)-5-methoxyphenoxy]acetate

To a solution of 2-chloro-4-(hydroxymethyl)-5-methoxyphenol (Intermediate 29; 2.0 g, 10.6 mmol) in acetonitrile (6 mL) was added tert-butyl 2-bromoacetate (1.60 mL, 10.83 mmol) and potassium carbonate (1.50 g, 10.85 mmol) in a sealed tub. The mixture was stirred 4 hours at 90° C. The solid was filtered, washed with acetonitrile and the solvent of the filtrate was removed under reduced pressure giving the title compound as an oil (3.2 g of an 85% purity, 85%), which was used in the next step without further purification.

LRMS (m/z): 285 (M-OH[tropilium cation])+; 187 (M−1)−

Intermediate 31 tert-butyl (2-chloro-4-formyl-5-methoxyphenoxy)acetate

To a solution of tert-butyl [2-chloro-4-(hydroxymethyl)-5-methoxyphenoxy]acetate (Intermediate 30, 2.55 g, 8.42 mmol) in chloroform (10 mL) was added manganese dioxide (4.06 g, 46.7 mmol) and the resulting suspension was heated at 45° C. overnight. The suspension was then filtered through a pad of Celite® and the filtrate was concentrated to dryness. The orange precipitate obtained was treated with diethyl ether and the slurry obtained was filtered and the solid was washed with further diethyl ether which, after drying, provided the title compound as a yellow solid (1.67 g, 84%).

LRMS (m/z): 301 (M+1)+

Intermediate 32

(2-chloro-4-formyl-5-methoxyphenoxy)acetic acid

To a solution of tert-butyl (2-chloro-4-formyl-5-methoxyphenoxy)acetate (Intermediate 31; 1.15 g, 3.82 mmol) in chloroform (8 mL) was added trifluoroacetic acid (2.95 mL, 38.24 mmol). The reaction mixture was stirred for 4 hours at 45° C. The solvent was removed under reduced pressure and the residue was treated with diethyl ether, filtered and dried to give the title compound as a solid (870 mg, 93%), which was used in the next step without further purification.

LRMS (m/z): 245 (M+1)+

Intermediate 33

(3R)-1-azabicyclo[2.2.2]oct-3-yl 1-(3-{3-[[(2-chloro-4-formyl-5-methoxyphenoxy) acetyl](methyl)amino]propyl}phenyl)cyclohexanecarboxylate Obtained as a yellowish oil (406 mg, 87%) from (3R)-1-azabicyclo[2.2.2]oct-3-yl 1-{3-[3-(methylamino)propyl]phenyl}cyclohexanecarboxylate (Intermediate 24, 300 mg, 0.78 mmol), (2-chloro-4-formyl-5-methoxyphenoxy)acetic acid (Intermediate 32, 174 mg, 0.71 mmol), DIEA (560 µL, 3.2 mmol) and HATU (350 mg, 0.92 mmol) following the experimental procedure described for the synthesis of Intermediate 12. The crude residue was purified by column chromatography over silica gel using a gradient of Hexane/Chloroform/Methanol.

LRMS (m/z): 612 (M+1)+

Intermediate 34

(3R)-1-azabicyclo[2.2.2]oct-3-yl 1-(3-{3-[{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}(methyl)amino]propyl}phenyl)cyclohexanecarboxylate Obtained as a yellowish foam (508 mg, 61%) from (3R)-1-azabicyclo[2.2.2]oct-3-yl 1-(3-{3-[[(2-chloro-4- formyl-5-methoxyphenoxy)acetyl](methyl)amino]propyl}phenyl)cyclohexanecarboxylate (Intermediate 33, 526 mg, 0.86 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 339 mg, 0.86 mmol) and sodium triacetoxyborohydride (687 mg, 3.24 mmol) following the experimental procedure described for the synthesis of Intermediate 15. The crude residue was purified by column chromatography over silica gel using a gradient of Chloroform/Methanol.

LRMS (m/z): 930 (M+1)+

Example 4

(3R)-1-azabicyclo[2.2.2]oct-3-yl 1-(3-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]propyl}phenyl)cyclohexanecarboxylate Obtained as a light yellow solid (331 mg as a dihydrofluoride salt, 71%) from (3R)-1-azabicyclo[2.2.2]oct-3-yl 1-(3-{3-[{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}(methyl)amino]propyl}phenyl)cyclohexanecarboxylate (Intermediate 34, 505 mg, 0.54 mmol) and triethylamine trihydrofluoride (443 μL, 2.72 mmol) following the experimental procedure described for the synthesis of Example 1. The solid obtained was purified by reverse phase column chromatography over C18 modified silica gel using a gradient of water/methanol.

LRMS (m/z): 816 (M+1)+

1H NMR (300 MHz, dmso) δ 10.50-10.25 (bs, 1H), 8.10 (d, 1H), 7.39 (s, 1H), 7.24-7.16 (m, 3H), 7.09-7.03 (m, 2H), 6.92 (d, 1H), 6.64 (d, 1H), 6.50 (d 1H), 5.18 (t, 1H), 4.98 (s 2H), 4.80-4.70 (m, 1H), 3.85 (s, 3H), 3.70 (s, 3H), 2.99 (s, 3H), 2.81-2.71 (m, 3H), 2.60-2.56 (m, 2H), 2.41-2.33 (m, 3H), 1.88-1.80 (m 2H), 1.70-1.21 (m 16H)

Intermediate 35

4-(but-3-en-1-ylamino)-3-nitrobenzonitrile

To a solution of 4-amino-3-nitrobenzonitrile (1.63 g, 10.0 mmol) in dimethylacetamide (4 mL) was added 4-bromobut-1-ene (1.2 mL, 11.8 mmol) and potassium carbonate (7.05 g, 51.0 mmol). The mixture was stirred at 75° C. for 72 hours. The reaction was diluted with acetonitrile and filtered. The filtrate was concentrated under reduced pressure and the crude obtained was purified by column chromatography with silica gel, eluting with a mixture of hexane:chloroform to give the title compound as an oil (1.84 g, 85%).

LRMS (m/z): 218 (M+1)+

Intermediate 36

3-amino-4-(but-3-en-1-ylamino)benzonitrile

To a solution of 4-(but-3-en-1-ylamino)-3-nitrobenzonitrile (Intermediate 35; 2 g, 0.009 mol) in ethanol (20 mL) was added Tin(II)chloride (11.1 g, 0.049 mol). The reaction mixture was stirred at 90° C. for 4 hours. The solvent was partially removed and sodium hydroxide was added to precipitate salts, which were filtrated. The solvent was removed under reduced pressure to give the title compound (1.6 g, 92%), which was used in the next step without further purification.

LRMS (m/z): 188 (M+1)+

Intermediate 37

1-but-3-en-1-yl-1H-1,2,3-benzotriazole-5-carbonitrile 3-amino-4-(but-3-en-1-ylamino)benzonitrile (Intermediate 36; 1 g, 5.34 mmol) was dissolved in hydrogen chloride (5N aqueous solution, 9.6 mL). The reaction mixture was cooled to 0° C. and a solution of sodium nitrite (0.55 g, 8.01 mmol) in water (20 mL) was added. The reaction mixture was stirred for 2 hours at room temperature. Water was added into the mixture and the crude was extracted with chloroform. The solvent was removed under reduced pressure and the crude obtained was crystallized with pentane giving the title compound as a solid (0.84 g, 79%).

LRMS (m/z): 199 (M+1)+

Intermediate 38

1-but-3-en-1-yl-1H-1,2,3-benzotriazole-5-carbaldehyde 1-but-3-en-1-yl-1H-1,2,3-benzotriazole-5-carbonitrile (Intermediate 37; 1.0 g, 5.04 mmol) was dissolved in an aqueous solution of Formic Acid 75% w/w (8.7 mL) and a Niguel-Aluminium alloy (1.08 g, 12.6 mmol) was added. The mixture was stirred at 80° C. for 3 hours. The solids were removed by filtration through Celite and the solvent was removed under reduced pressure to provide a brownish oil that was purified by column chromatography over silica gel eluting with a gradient of Hexane:Ethyl acetate. The title compound was obtained as a colorless oil (480 mg of an 83% purity, 39% yield).

LRMS (m/z): 202 (M+1)+

Intermediate 39

(3R)-1-azabicyclo[2.2.2]oct-3-yl 1-{3-[(1E)-4-(5-formyl-1H-1,2,3-benzotriazol-1-yl) but-1-en-1-yl]phenyl}cyclohexanecarboxylate Obtained as a colorless solid (141 mg, 90%) from (3R)-1-azabicyclo[2.2.2]oct-3-yl 1-(3-bromophenyl)cyclohexanecarboxylate (Intermediate 3, 120 mg, 0.306 mmol), 1-but-3-en-1-yl-1H-1,2,3-benzotriazole-5-carbaldehyde (Intermediate 38, 65 mg, 0.32 mmol), tri-ortho-tolylphosphine (94 mg, 0.31 mmol), DIEA (96 μL, 0.55 mmol) and palladium acetate (41 mg, 0.18 mmol) in acetonitrile (1.3 mL) following the experimental procedure described for the synthesis of Intermediate 6. The crude residue obtained was purified by column chromatography over silica gel using a gradient of Chloroform/Methanol going from 50/1 to 4/1.

LRMS (m/z): 513 (M+1)+

Intermediate 40

(3R)-1-azabicyclo[2.2.2]oct-3-yl 1-{3-[4-(5-formyl-1H-1,2,3-benzotriazol-1-yl)butyl]phenyl}cyclohexanecarboxylate Obtained as a colorless oil (68 mg, 49%) from (3R)-1-azabicyclo[2.2.2]oct-3-yl 1-{3-[(1E)-4-(5-formyl-1H-1,2,3- benzotriazol-1-yl)but-1-en-1-yl]phenyl}cyclohexane carboxylate (Intermediate 39, 135 mg, 0.26 mmol) and palladium on carbon (28 mg of a 10% by weight, 0.026 mmol) in acetic acid (3 mL), following the experimental procedure described for the synthesis of Intermediate 7. The crude product was purified by column chromatography over silica gel using a gradient of Chloroform:Methanol as eluent.

LRMS (m/z): 515 (M+1)+

Intermediate 41

(3R)-1-azabicyclo[2.2.2]oct-3-yl 1-(3-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]butyl}phenyl)cyclohexanecarboxylate Obtained as a yellowish foam (194 mg, 77%) from (3R)-1-azabicyclo[2.2.2]oct-3-yl 1-{3-[4-(5-formyl-1H-1,2,3-benzotriazol-1-yl)butyl]phenyl}cyclohexanecarboxylate (Intermediate 40, 150 mg, 0.29 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 115 mg, 0.29 mmol) and sodium triacetoxyborohydride (233 mg, 1.1 mmol) following the experimental procedure described for the synthesis of Intermediate 15. The crude residue was purified by column chromatography over silica gel using a gradient of Chloroform/Methanol from 50/1 to 4/1.

LRMS (m/z): 833 (M+1)+

Example 5

(3R)-1-azabicyclo[2.2.2]oct-3-yl 1-(3-{4-[5-({[(2R)-2-hydroxy-2-(8-hydroxy-2-oxo-1,2-dihydroquinolin-5-yl)ethyl]amino}methyl)-1H-1,2,3-benzotriazol-1-yl]butyl}phenyl)cyclohexanecarboxylate Obtained as a white solid (104 mg as a dihydrofluoride salt, 58%) from (3R)-1-azabicyclo[2.2.2]oct-3-yl 1-(3-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]butyl}phenyl)cyclohexanecarboxylate (Intermediate 41, 190 mg, 0.23 mmol) and triethylamine trihydrofluoride (186 μL, 1.14 mmol) following the experimental procedure described for the synthesis of Example 1. No additional purification was required in this example.

LRMS (m/z): 720 (M+1)+

1H NMR (300 MHz, dmso) δ 8.12 (d, 1H), 7.95 (s 1H), 7.79 (d, 1H), 7.52 (d 1H), 7.26-7.11 (m, 3H), 7.07-7.00 (m, 2H), 6.90 (d, 1H), 6.42 (d, 1H), 5.10 (dd, 1H), 4.70 (t, 2H), 4.66-4.62 (m 1H), 3.94 (s, 2H), 3.06-2.98 (m 1H), 2.74-2.67 (m 2H), 2.61-2.54 (m 3H), 2.48-2.25 (m 5H), 1.89 (dd 2H), 1.73-1.21 (m 16H)

Intermediate 42

6-(chloroacetyl)-3,4-dihydroquinolin-2(1H)-one

A solution of chloroacetyl chloride (0.9 g, 11.32 mmol) in dichloromethane (7 mL) was added, under nitrogen atmosphere, over a suspension of aluminium trichloride (4.2 g, 31.5 mmol) in dichloromethane (30 mL) and the mixture was stirred at room temperature for 45 min. Then, a suspension of 3,4-dihydroquinolin-2(1H)-one (1.5 g, 10.2 mmol) in dichloromethane (17 mL+13 mL of washing) was slowly added to the mixture and stirring was continued for 2 hours at rt, heated for 2 additional hours at 40° C. and stirred at r.t. overnight. Cold water was added to the reaction mixture (30 mL) and the organic solvent was partially evaporated. The residue obtained was filtered and the filter cake was washed with cold water and diethyl ether, and dried overnight to afford the title compound (2.12 g, 93%) as a brown solid.

LRMS (m/z): 224 (M+1)+

Intermediate 43

2-oxo-1,2,3,4-tetrahydroquinoline-6-carboxylic acid 6-(chloroacetyl)-3,4-dihydroquinolin-2(1H)-one (Intermediate 42, 2.12 g, 9.5 mmol) was suspended over pyridine (10 mL) and THF was added (15 mL) to allow for vigorous stirring. The reaction mixture was then heated to 90° C. for 2.5 hours and left at 75° C. overnight. The suspension was allowed to cool to rt, filtered and oven-dried to afford a brown solid (2.56 g of the pyridinium salt derivative intermediate). This solid was then added over a 0.5M aqueous sodium hydroxide solution (32 mL) and the mixture was heated to 80° C. for 1 hour. After cooling to rt, the resulting brown solution was acidified with concentrated HCl until acidic pH was reached (pH=3-4) and stirring was continued overnight. The suspension was filtered and the precipitate obtained was washed with water, THF and diethyl ether to afford the title compound (1.38 g, 76%) as a brown oil.

LRMS (m/z): 190 (M−1)−

Intermediate 44

Methyl 2-oxo-1,2,3,4-tetrahydroquinoline-6-carboxylate 2-oxo-1,2,3,4-tetrahydroquinoline-6-carboxylic acid (Intermediate 43, 865 mg, 4.52 mmol) was suspended in methanol (35 mL) in a sealed tube and hydrochloric acid (8 mL of a 4M solution in dioxane, 32 mmol) was added. The mixture was heated to 100° C. for 2 hours and the solvent was evaporated to dryness. The solid residue was dissolved in chloroform (30 mL) and filtered. The filtrate was concentrated under reduced pressure and the precipitate obtained was washed with diethyl ether, which upon drying, afforded the title compound (788 mg, 83%) as a light yellow solid.

LRMS (m/z): 206 (M+1)+

Intermediate 45

6-(hydroxymethyl)-3,4-dihydroquinolin-2(1H)-one

To a suspension of methyl 2-oxo-1,2,3,4-tetrahydroquinoline-6-carboxylate (Intermediate 44, 230 mg, 1.12 mmol) in THF (6 mL) was added portionwise, at 0° C. and under nitrogen atmosphere, lithium aluminium hydride (85 mg, 2.24 mmol). After 30 min, the reaction mixture was treated with sequential addition of water (85 μL), 4N aqueous sodium hydroxide (85 μL) and water (255 μL), and the suspension was filtered through a pad of Celite® washing with additional THF. The filtrate was concentrated to dryness and the semi-solid obtained was treated with diethyl ether and, upon filtration, provided the title compound (58 mg of an 86% purity, 25%) as a pale yellow solid. The compound was used as this without any further purification.
LRMS (m/z): 178 (M+1)+

Intermediate 46

2-oxo-1,2,3,4-tetrahydroquinoline-6-carbaldehyde

Obtained as a yellow solid (55 mg, 77%) from 6-(hydroxymethyl)-3,4-dihydroquinolin-2(1H)-one (Intermediate 45, 57 mg, 0.32 mmol) and manganese dioxide (280 mg, 3.22 mmol) in chloroform (1.5 mL) following the experimental procedure described for the synthesis of Intermediate 31.
LRMS (m/z): 176 (M+1)+

Intermediate 47

1-but-3-en-1-yl-2-oxo-1,2,3,4-tetrahydroquinoline-6-carbaldehyde

To a suspension of sodium hydride (16 mg of a 60 dispersion in oil, 0.67 mmol) in DMF (0.5 mL) was added a solution of 2-oxo-1,2,3,4-tetrahydroquinoline-6-carbaldehyde (Intermediate 46, 68 mg, 0.39 mmol) and stirring at rt was maintained for 20 min. Then, 4-bromobut-1-ene (79 μL, 0.78 mmol) was added and the reaction mixture was allowed to stir for 30 min at rt. Monitoring by UPLC showed remaining starting material and additional sodium hydride (16 mg of a 60 dispersion in oil, 0.67 mmol) and 4-bromobut-1-ene (79 μL, 0.78 mmol) were added two more times until no starting material was observed. The mixture was poured over ice-water and the aqueous phase was extracted with ethyl acetate (3×10 mL). The combined organic extracts were washed with water (2×20 mL) and brine (20 mL), filtered and concentrated to dryness to afford a yellow foam, which was purified by column chromatography over silica gel using a gradient of Hexane/Chloroform/Methanol to provide the title compound (57 mg of a 90% purity, 32%) as a pale yellow foam.
LRMS (m/z): 230 (M+1)+

Intermediate 48

(3R)-1-azabicyclo[2.2.2]oct-3-yl 1-{3-[(1E)-4-(6-formyl-2-oxo-3,4-dihydroquinolin-1(2H)-yl)but-1-en-1-yl]phenyl}cyclohexanecarboxylate Obtained as a brownish oil (120 mg, 85%) from (3R)-1-azabicyclo[2.2.2]oct-3-yl 1-(3-bromophenyl)cyclohexanecarboxylate (Intermediate 3, 93 mg, 0.24 mmol), 1-but-3-en-1-yl-2-oxo-1,2,3,4-tetrahydroquinoline-6-carbaldehyde (Intermediate 47, 57 mg, 0.25 mmol), tri-ortho-tolylphosphine (73 mg, 0.24 mmol), DIEA (75 μL, 0.43 mmol) and palladium acetate (32 mg, 0.14 mmol) in acetonitrile (1.5 mL) following the experimental procedure described for the synthesis of Intermediate 6. The crude residue obtained was purified by column chromatography over silica gel using a gradient of Chloroform/Methanol going from 50/1 to 15/1.
LRMS (m/z): 541 (M+1)+

Intermediate 49

(3R)-1-azabicyclo[2.2.2]oct-3-yl 1-{3-[4-(6-formyl-2-oxo-3,4-dihydroquinolin-1(2H)-yl)butyl]phenyl}cyclohexanecarboxylate Obtained as a colorless oil (48 mg, 36%) from (3R)-1-azabicyclo[2.2.2]oct-3-yl 1-{3-[(1E)-4-(6-formyl-2-oxo-3,4-dihydroquinolin-1(2H)-yl)but-1-en-1-yl]phenyl}cyclohexane carboxylate (Intermediate 48, 120 mg, 0.22 mmol) and palladium on carbon (24 mg of a 10% by weight, 0.023 mmol) in acetic acid (2.5 mL), following the experimental procedure described for the synthesis of Intermediate 7. The crude product was purified by column chromatography over silica gel using a gradient of Chloroform:Methanol as eluent going from 50/1 to 15/1.
LRMS (m/z): 543 (M+1)+

Intermediate 50

(3R)-1-azabicyclo[2.2.2]oct-3-yl 1-(3-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-3,4-dihydroquinolin-1(2H)-yl]butyl}phenyl)cyclohexanecarboxylate Obtained as a yellowish foam (80 mg of an 85% purity, 77%) from (3R)-1-azabicyclo[2.2.2]oct-3-yl 1-{3-[4-(6-formyl-2-oxo-3,4-dihydroquinolin-1(2H)-yl)butyl]phenyl}cyclohexanecarboxylate (Intermediate 49, 47 mg, 0.086 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 34 mg, 0.086 mmol) and sodium triacetoxyborohydride (69 mg, 0.32 mmol) following the experimental procedure described for the synthesis of Intermediate 15. No further purification was performed in this case.
LRMS (m/z): 862 (M+1)+

Example 6

(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxo-3,4-dihydroquinolin-1(2H)-yl]butyl}phenyl)cyclohexanecarboxylate Obtained as a white solid (34 mg as a dihydrofluoride salt, 45%) from (3R)-1-azabicyclo[2.2.2]oct-3-yl 1-(3-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-3,4-dihydroquinolin-1(2H)-yl]butyl}phenyl)cyclohexanecarboxylate (Intermediate 50, 80 mg, 0.093 mmol) and triethylamine trihydrofluoride (75 μL, 0.46 mmol) following the experimental procedure described for the synthesis of Example 1. No additional purification was required in this example.
LRMS (m/z): 748 (M+1)+
1H NMR (300 MHz, dmso) δ 8.12 (d, 1H), 7.28-7.13 (m, 6H), 7.08-6.90 (m, 3H), 6.48 (d, 1H), 5.09 (dd, 1H), 4.67-4.65 (m, 1H), 3.87 (t, 2H), 2.34 (s, 2H), 3.07-3.00 (m, 1H), 2.81-2.70 (m, 4H), 2.62-2.55 (m, 4H), 2.40-2.27 (m 4H), 1.77-1.20 (m 16H)

Intermediate 51 tert-butyl {5-[((2R)-2-[8-(benzyloxy)-2-oxo-1,2-dihydroquinolin-5-yl]-2-{[tert-butyl(dimethyl)silyl]oxy}ethyl)amino]pentyl}carbamate 8-(benzyloxy)-5-((1R)-2-bromo-1-{[tert-butyl(dimethyl)silyl]oxy}ethyl)quinolin-2(1H)-one (prepared according to US20040059116, 482 mg, 0.99 mmol) and tert-butyl-5-aminopentylcarbamate (0.51 mL, 2.47 mmol) were dissolved in DMSO (1 mL) and the mixture was heated to 105° C. over a period of 6 hours. Then, ethyl acetate was added and the organic phase was washed with 4% aqueous sodium bicarbonate solution. The organic phase was dried, filtered and concentrated to dryness. The residue was purified by column chromatography over silica gel eluting with a gradient of dichloromethane and dichloromethane/methanol (95:5) to afford the title compound (581 mg, 96%) as a colorless oil.

LRMS (m/z): 610 (M+1)+

Intermediate 52

5-((1R)-2-[(5-aminopentyl)amino]-1-{[tert-butyl (dimethyl)silyl]oxy}ethyl)-8-(benzyloxy)quinolin-2 (1H)-one To a solution of tert-butyl {5-[((2R)-2-[8-(benzyloxy)-2-oxo-1,2-dihydroquinolin-5-yl]-2-{[tert-butyl(dimethyl)silyl]oxy}ethyl)amino]pentyl}carbamate (Intermediate 51, 581 mg, 0.95 mmol) in dichloromethane (6.6 mL) was added, under argon atmosphere, trifluroacetic acid (2.2 mL, 28.55 mmol) and the mixture was stirred at rt for 1 hour. The reaction mixture was then evaporated under reduced pressure and the residue was dissolved in dichloromethane (15 mL). The resulting organic phase was washed with 1N aqueous sodium hydroxide (15 mL), dried over anhydrous sodium sulphate, filtered and concentrated to dryness to give the title compound (494 mg, 100%) as a colorless oil.

LRMS (m/z): 510 (M+1)+

Intermediate 53

(3R)-1-azabicyclo[2.2.2]oct-3-yl 1-(3-{(13R)-13-[8-(benzyloxy)-2-oxo-1,2-dihydroquinolin-5-yl]-15,15, 16,16-tetramethyl-4-oxo-14-oxa-5,11-diaza-15-silaheptadec-1-yl}phenyl)cyclohexanecarboxylate Obtained as a yellowish oil (338 mg, 84%) from 4-[3-(1-{[(3R)-1-azabicyclo[2.2.2]oct-3-yloxy] carbonyl}cyclohexyl)phenyl]butanoic acid (Intermediate 11, 204 mg of the TFA salt, 0.40 mmol), 5-((1R)-2-[(5-aminopentyl)amino]-1-{[tert-butyl(dimethyl)silyl] oxy}ethyl)-8-(benzyloxy)quinolin-2(1H)-one (Intermediate 52, 198 mg, 0.39 mmol), DIEA (2534, 1.45 mmol) and HATU (159 mg, 0.42 mmol) in chloroform (4.6 mL) following the experimental procedure described for the synthesis of Intermediate 12. The crude residue was purified by column chromatography over silica gel using a gradient of Chloroform and Chloroform/Methanol/Ammonia (40:8:1).

LRMS (m/z): 892 (M+1)+

Intermediate 54

(3R)-1-azabicyclo[2.2.2]oct-3-yl 1-{3-[(13R)-13-(8-hydroxy-2-oxo-1,2-dihydroquinolin-5-yl)-15,15,16, 16-tetramethyl-4-oxo-14-oxa-5,11-diaza-15-silaheptadec-1-yl]phenyl}cyclohexanecarboxylate Palladium on carbon (54 mg of a 10% by weight, 0.051 mmol) was added to a solution of (3R)-1-azabicyclo[2.2.2] oct-3-yl 1-(3-{(13R)-13-[8-(benzyloxy)-2-oxo-1,2-dihydro quinolin-5-yl]-15,15,16,16-tetramethyl-4-oxo-14-oxa-5,11-diaza-15-silaheptadec-1-yl}phenyl)cyclohexanecarboxylate (Intermediate 53, 272 mg, 0.31 mmol) in ethanol (11 mL) and the mixture was placed under hydrogen atmosphere over a period of 22 hours. Then the reaction mixture was filtered through a 4μ PTFE membrane filter and the filtrate was concentrated to dryness to yield the title compound (260 mg, 99%) as a yellowish oil.

LRMS (m/z): 802 (M+1)+

Example 7

(3R)-1-azabicyclo[2.2.2]oct-3-yl 1-(3-{4-[(5-{[(2R)-2-hydroxy-2-(8-hydroxy-2-oxo-1,2-dihydroquinolin-5-yl)ethyl]amino}pentyl)amino]-4-oxobutyl}phenyl) cyclo hexanecarboxylate Obtained as a white solid (145 mg as a dihydrofluoride salt, 57%) from (3R)-1-azabicyclo[2.2.2]oct-3-yl 1-{3-[(13R)-13-(8-hydroxy-2-oxo-1,2-dihydroquinolin-5-yl)-15, 15,16,16-tetramethyl-4-oxo-14-oxa-5,11-diaza-15-silaheptadec-1-yl]phenyl}cyclo hexanecarboxylate (Intermediate 54, 254 mg, 0.32 mmol) and triethylamine trihydrofluoride (105 μL, 0.64 mmol) following the experimental procedure described for the synthesis of Example 1. No additional purification was required in this example.

LRMS (m/z): 688 (M+1)+

1H NMR (300 MHz, dmso) δ 8.23 (d, 1H), 7.82 (t, 1H), 7.29-7.13 (m, 3H), 7.07 (d, 1H), 6.98 (d, 1H), 6.56 (d, 1H), 5.35 (dd, 1H), 4.73-4.70 (m, 1H), 3.16-2.95 (m, 6H), 2.90-2.85 (m, 3H), 2.73-2.64 (m, 3H), 2.56-2.28 (m, 3H), 2.08-2.03 (m 2H), 1.84-1.28 (m, 22H)

Intermediate 55

Methyl 2-oxo-1,2-dihydroquinoline-6-carboxylate

To a solution of methyl 2-oxo-1,2,3,4-tetrahydroquinoline-6-carboxylate (Intermediate 44, 1.31 g, 6.39 mmol) in chloroform (52 mL) in a high pressure vessel, were sequentially added N-bromosuccinimide (2.13 g, 11.98 mmol) and benzoyl peroxide (8 mg, 0.033 mmol) and the reaction vessel was heated at 80° C. for 3 hours. Then, the solvent was evaporated and the solid residue was treated with ethanol (50 mL) and filtered. The precipitate obtained was washed with additional cold ethanol and diethyl ether (twice) which upon drying afforded the title compound (1.1 g, 84%) as a white solid.

LRMS (m/z): 204 (M+1)+

Intermediate 56

6-(hydroxymethyl)quinolin-2(1H)-one

Lithium borohydride (2.5 mL of a 2M solution in THF, 2.5 mmol) was added to a suspension of methyl 2-oxo-1,2-dihydroquinoline-6-carboxylate (Intermediate 55, 500 mg, 2.46 mmol) in THF (19 mL) and the mixture was heated to 40° C. for 4 hours. Then, additional lithium borohydride (2.5 mL of a 2M solution in THF, 2.5 mmol) was added (reaction monitoring showed remaining starting material) and heated to 40° C. for an additional 24 hours. The reaction mixtures was then slowly poured over an ice cold hydrochloric acid aqueous solution (20 mL of a 2N HCl solution) and stirring was maintained over a period of 15 min allowing to warm up to rt. Ethyl acetate was added to the mixture (75 mL) and decanted from the reaction mixture and the process was repeated again with additional 75 mL. The remaining residue, containing a solid and the aqueous phase, was filtered and washed once with the obtained mother liquors from the first filtration and twice with diethyl ether. Upon drying, the title compound (262 mg, 59%) was obtained as a white solid.
LRMS (m/z): 176 (M+1)+

Intermediate 57

2-oxo-1,2-dihydroquinoline-6-carbaldehyde

Obtained as a white solid (166 mg of an 89% purity, 71%) from 6-(hydroxymethyl)quinolin-2(1H)-one (Intermediate 56, 210 mg, 1.20 mmol) and Dess-Martin periodinane reagent (609 mg, 1.43 mmol) following the experimental procedure described for the synthesis of Intermediate 14.
LRMS (m/z): 174 (M+1)+

Intermediate 58

1-but-3-en-1-yl-2-oxo-1,2-dihydroquinoline-6-carbaldehyde

Obtained as a white solid (56 mg, 22%) from 2-oxo-1,2-dihydroquinoline-6-carbaldehyde (142 mg, 0.82 mmol), 4-bromobut-1-ene (168 μL, 1.66 mmol) and sodium hydride (88 mg of a 60% dispersion in oil, 3.67 mmol) following the experimental procedure described for the synthesis of Intermediate 47. Purification was performed by normal phase column chromatography over silica gel eluting with a gradient of hexane/chloroform.
LRMS (m/z): 228 (M+1)+

Intermediate 59

(3R)-1-azabicyclo[2.2.2]oct-3-yl 1-{3-[(1E)-4-(6-formyl-2-oxoquinolin-1(2H)-yl)but-1-en-1-yl]phenyl}cyclohexanecarboxylate Obtained as a yellowish oil (119 mg of a 93% purity, 88%) from (3R)-1-azabicyclo[2.2.2]oct-3-yl 1-(3-bromophenyl)cyclohexanecarboxylate (Intermediate 3, 92 mg, 0.24 mmol), 1-but-3-en-1-yl-2-oxo-1,2-dihydroquinoline-6-carbaldehyde (Intermediate 58, 56 mg, 0.25 mmol), tri-ortho-tolylphosphine (71 mg, 0.23 mmol), DIEA (74 μL, 0.42 mmol) and palladium acetate (32 mg, 0.14 mmol) in acetonitrile (1.5 mL) following the experimental procedure described for the synthesis of Intermediate 6. The crude residue obtained was purified by column chromatography over silica gel using a gradient of Chloroform/Methanol going from 50/1 to 15/1.
LRMS (m/z): 539 (M+1)+

Intermediate 60

3R)-1-azabicyclo[2.2.2]oct-3-yl 1-{3-[4-(6-formyl-2-oxoquinolin-1(2H)-yl)butyl]phenyl}cyclohexanecarboxylate Obtained as a colorless oil (26 mg, 20%) from (3R)-1-azabicyclo[2.2.2]oct-3-yl 1-{3-[(1E)-4-(6-formyl-2-oxoquinolin-1(2H)-yl)but-1-en-1-yl]phenyl}cyclohexanecarboxylate (Intermediate 59, 59 mg, 0.11 mmol) and palladium on carbon (24 mg of a 10% by weight, 0.011 mmol) in acetic acid (0.5 mL) and THF (0.75 mL), following the experimental procedure described for the synthesis of Intermediate 7. The crude product was purified initially by column chromatography over silica gel using a gradient of Chloroform:Methanol as eluent going from 50/1 to 15/1, and additionally by reverse phase column chromatography over C18 modified silica gel eluting with a gradient of water/methanol.
LRMS (m/z): 541 (M+1)+

Intermediate 61

(3R)-1-azabicyclo[2.2.2]oct-3-yl 1-(3-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxoquinolin-1(2H)-yl]butyl}phenyl)cyclohexanecarboxylate Obtained as a yellowish foam (41 mg of an 83% purity, 82%) from (3R)-1-azabicyclo[2.2.2]oct-3-yl 1-{3-[4-(6-formyl-2-oxoquinolin-1(2H)-yl)butyl]phenyl}cyclo hexanecarboxylate (Intermediate 60, 26 mg, 0.048 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 19 mg, 0.048 mmol) and sodium triacetoxyborohydride (38 mg, 0.18 mmol) following the experimental procedure described for the synthesis of Intermediate 15. No further purification was performed in this case.
LRMS (m/z): 860 (M+1)+

Example 8

(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxoquinolin-1(2H)-yl]butyl}phenyl)cyclohexanecarboxylate Obtained as a white solid (20 mg as a dihydrofluoride salt, 61%) from (3R)-1-azabicyclo[2.2.2]oct-3-yl 1-(3-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-quinolin-1(2H)-yl]butyl}phenyl)cyclohexanecarboxylate (Intermediate 61, 41 mg, 0.048 mmol) and triethylamine trihydrofluoride (39 μL, 0.24 mmol) following the experimental procedure described for the synthesis of Example 1. No additional purification was required in this example.
LRMS (m/z): 746 (M+1)+
1H NMR (300 MHz, dmso) δ 8.10 (d, 1H), 7.81 (d, 1H), 7.62 (s, 1H), 7.54 (d, 1H), 7.42 (d, 1H), 7.23-7.13 (m, 3H), 7.07-7.03 (m, 2H), 6.89 (d, 1H), 6.55 (d, 1H), 6.43 (d, 1H), 5.09 (dd, 1H), 4.66-4.62 (m, 1H), 4.23-4.18 (m, 2H), 3.84 (s, 2H), 3.06-3.00 (m, 1H), 2.72-2.32 (m, 9H), 1.73-1.13 (m, 18H)

Intermediate 62 tert-butyl but-3-en-1-ylcarbamate

Triethylamine (1.80 mL, 12.98 mmol) was added to a solution of but-3-en-1-amine (700 mg, 9.84 mmol) in dichloromethane (11 mL). The mixture was cooled to 0° C. and di-tert-butyldicarbonate (2.7 g, 12.37 mmol) was added portionwise under nitrogen atmosphere. The reaction mixtures was allowed to warm up to r.t. and stirring was continued for 16 hours. The solvent was evaporated and the residue was redissolved in diethyl ether (20 mL). The organic phase was washed with saturated aqueous ammonium chloride solution (2×20 mL) and brine, dried over anhydrous sodium sulphate, filtered and concentrated to dryness to afford the title compound as a colorless oil (1.68 g, 100%).

LRMS (m/z): 172 (M+1)+

Intermediate 63

(3R)-1-azabicyclo[2.2.2]oct-3-yl 1-(3-{(1E)-4-[(tert-butoxycarbonyl)amino]but-1-en-1-yl}phenyl)cyclo-hexanecarboxylate Obtained as a pale yellow foam (1.31 g, 92%) from (3R)-1-azabicyclo[2.2.2]oct-3-yl 1-(3-bromophenyl)cyclo-hexanecarboxylate (Intermediate 3, 1.0 g, 2.55 mmol), tert-butyl but-3-en-1-ylcarbamate (Intermediate 62, 460 mg, 2.69 mmol), tri-ortho-tolylphosphine (776 mg, 2.55 mmol), DIEA (0.80 mL, 4.60 mmol) and palladium acetate (344 mg, 1.53 mmol), following the experimental procedure described for the synthesis of Intermediate 6. Purification of the crude residue was performed by column chromatography over silica gel using as a gradient a mixture of eluents Hexane:Chloroform:Methanol.

LRMS (m/z): 483 (M+1)+

Intermediate 64

(3R)-1-azabicyclo[2.2.2]oct-3-yl 1-(3-{4-[(tert-butoxycarbonyl)amino]butyl}phenyl)cyclohexanecarboxylate Obtained as a colorless oil (1.33 g of an 80% purity, acetate salt, 80%) from (3R)-1-azabicyclo[2.2.2]oct-3-yl 1-(3-{(1E)-4-[(tert-butoxycarbonyl)amino]but-1-en-1-yl}phenyl)cyclohexanecarboxylate (Intermediate 63, 1.3 g, 2.7 mmol) and palladium on carbon (304 mg of a 10% by weight, 0.28 mmol) in a mixture of acetic acid (8 mL) and THF (8 mL), following the experimental procedure described for the synthesis of Intermediate 7. The compound was used without any further purification.

LRMS (m/z): 485 (M+1)+

Intermediate 65

(3R)-1-azabicyclo[2.2.2]oct-3-yl 1-[3-(4-aminobutyl)phenyl]cyclohexane carboxylate Obtained as a yellowish solid (1.01 g, 89%) from (3R)-1-azabicyclo[2.2.2]oct-3-yl 1-(3-{4-[(tert-butoxycarbonyl)amino]butyl}phenyl)cyclohexanecarboxylate (Intermediate 64, 1.51 g, 1.23 mmol) and hydrochloric acid (4.70 mL of a 4M solution in Dioxane, 18.8 mmol) in chloroform (50 mL) following the experimental procedure described for the synthesis of Intermediate 24.

LRMS (m/z): 385 (M+1)+

Intermediate 66

5-chloro-4-cyano-2-methoxybenzoic acid

To a suspension of 4-amino-5-chloro-2-methoxybenzoic acid (4.0 g, 19.8 mmol) in water (66 mL) was added concentrated hydrogen chloride (6.6 mL of a 35% solution in water, 79.2 mmol) and the resulting mixture was cooled to 0° C. with vigorous stirring. Then, a solution of sodium nitrite (1.95 g, 28.3 mmol) in water (6 mL) was added dropwise while maintaining the internal temperature below 4° C. After 5 min, the mixture containing the diazonium salt was slowly added, through an addition funnel and maintaining the temperature below 5° C., over a mechanically stirred solution of copper cyanide (2.4 g, 26.8 mmol) and sodium cyanide (3.7 g, 75.5 mmol) in water (20 mL, this solution was freshly prepared from a suspension of the copper cyanide in water and slow addition of sodium cyanide while keeping the temperature below 40° C. and allowed to cool to rt). Once the addition was finished, the reaction mixture was allowed to warm to rt and vigorous stirring was maintained for 4 hours. Then, water and hydrogen chloride (5N) were added to the mixture and the aqueous phase was extracted with ethyl acetate. The whole mixture was filtered to remove the solids and the phases were separated. The aqueous phase was further extracted twice with ethyl acetate and the combined organic extracts were washed with brine, dried, decolorized with active carbon, filtered and concentrated to dryness to afford the title compound as light yellow solid (3.0 g, 70%).

LRMS (m/z): 210 (M−1)−

Intermediate 67

2-chloro-4-(hydroxymethyl)-5-methoxybenzonitrile

To a solution of 5-chloro-4-cyano-2-methoxybenzoic acid (Intermediate 66, 3.0 g, 14.2 mmol) in tetrahydrofuran (50 mL) was added slowly, at 0° C. and under argon atmosphere, borane dimethylsulfide complex (2.7 mL, 28.4 mmol). After the addition was finished, the reaction mixture was stirred at 0° C. for 5 min and then allowed to warm up to rt and stirred for 3 hours. Then, water was slowly added (6 mL) and the mixture was concentrated to dryness. The residue was suspended in ethyl acetate and filtered. The solid was washed with further ethyl acetate and the combined organic phases were decolorized with active carbon, filtered and concentrated under reduced pressure to afford the title compound as a yellowish solid (2.3 g, 80%).

LRMS (m/z): 215 (M+18[NH4+])+

Intermediate 68

2-chloro-4-(hydroxymethyl)-5-methoxybenzoic acid

To a suspension of 2-chloro-4-(hydroxymethyl)-5-methoxybenzonitrile (Intermediate 67, 1.8 g, 9.1 mmol) in ethanol (20 mL) in a sealed tube was added NaOH (8 mL of a 32% aqueous solution, 64 mmol) and the reaction mixture was heated at a 110° C. overnight. Then, water was added and the aqueous phase was washed with ethyl acetate twice, acidified with hydrochloric acid (5N) up to pH=2, and extracted with ethyl acetate twice. The combined organic extracts were dried and concentrated to dryness to provide the title compound as a white solid (1.3 g, 66%)

LRMS (m/z): 215 (M−1)−

Intermediate 69

(3R)-1-azabicyclo[2.2.2]oct-3-yl 1-[3-(4-{[2-chloro-4-(hydroxymethyl)-5-methoxybenzoyl]amino}butyl)phenyl]cyclohexanecarboxylate Obtained as a pale brown oil (133 mg of an 80% purity, 51%) from (3R)-1-azabicyclo[2.2.2]oct-3-yl 1-[3-(4-aminobutyl)phenyl]cyclohexane carboxylate (Intermediate 63, 137 mg, 0.36 mmol), 2-chloro-4-(hydroxymethyl)-5-methoxybenzoic acid (Intermediate 68, 103 mg, 0.47 mmol), DIEA (100 μL, 0.57 mmol) and HATU (210 mg, 0.55 mmol) in DMF (4 mL) following the experimental procedure described for the synthesis of Intermediate 33. Purification of the crude was performed by column chromatography over silica gel using a gradient of Hexane/Chloroform/Chloroform:Methanol:Ammonia (40:4:0.2).

LRMS (m/z): 584 (M+1)+

Intermediate 70

(3R)-1-azabicyclo[2.2.2]oct-3-yl 1-(3-{4-[(2-chloro-4-formyl-5-methoxybenzoyl)amino]butyl}phenyl)cyclohexanecarboxylate Obtained as an orange oil (135 mg of a 71% purity, 90%) from (3R)-1-azabicyclo[2.2.2]oct-3-yl 1-[3-(4-{[2-chloro-4-(hydroxymethyl)-5-methoxybenzoyl]amino}butyl)phenyl]cyclohexanecarboxylate (Intermediate 69, 133 mg, 0.23 mmol) and Dess-Martin periodinane reagent (609 mg, 1.43 mmol) in chloroform (3 mL), following the experimental procedure described for the synthesis of Intermediate 14.

LRMS (m/z): 582 (M+1)+

Intermediate 71

(3R)-1-azabicyclo[2.2.2]oct-3-yl 1-[3-(4-{[2-chloro-4-({[(2R)-2-{[tert-butyl(dimethyl)silyl]oxy}-2-(8-hydroxy-2-oxo-1,2-dihydroquinolin-5-yl)ethyl]amino}methyl)-5-methoxybenzoyl]amino}butyl)phenyl]cyclohexane carboxylate Obtained as a brownish oil (112 mg of a 75% purity, 57%) from (3R)-1-azabicyclo[2.2.2]oct-3-yl 1-(3-{4-[(2-chloro-4-formyl-5-methoxybenzoyl)amino]butyl}phenyl)cyclohexanecarboxylate (Intermediate 70, 134 mg of a 75% purity, 0.23 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 83 mg, 0.21 mmol) and sodium triacetoxyborohydride (106 mg, 0.50 mmol) following the experimental procedure described for the synthesis of Intermediate 15. Purification was performed by column chromatography over silica gel using a gradient of Chloroform/Chloroform:Methanol:Ammonia (40:4:0.2).

LRMS (m/z): 900 (M+1)+

Example 9

(3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)phenyl]cyclohexanecarboxylate Obtained as a bright yellow solid (20 mg as the free base, 49%) from (3R)-1-azabicyclo[2.2.2]oct-3-yl 1-[3-(4-{[2-chloro-4-({[(2R)-2-{[tert-butyl(dimethyl)silyl]oxy}-2-(8-hydroxy-2-oxo-1,2-dihydroquinolin-5-yl)ethyl]amino}methyl)-5-methoxybenzoyl]amino}butyl)phenyl]cyclohexane carboxylate (Intermediate 71, 112 mg of a 75% purity, 0.124 mmol) and triethylamine trihydrofluoride (102 μL, 0.62 mmol) following the experimental procedure described for the synthesis of Example 1. Purification was performed by reverse phase column chromatography over C18 modified silica gel using a gradient of Water/Methanol.

LRMS (m/z): 786 (M+1)+

1H NMR (300 MHz, dmso) δ 10.40-10.20 (bs, 1H), 8.34 (t, 1H), 8.12 (d, 1H), 7.34-7.15 (m, 4H), 7.08-7.02 (m, 2H), 6.92-6.84 (m, 1H), 6.46 (d, 1H), 5.03 (dd, 1H), 4.65-4.59 (m, 1H), 3.76 (s, 3H), 3.67 (s, 1H), 3.00-2.96 (m, 1H), 2.71-2.29 (m, 8H), 1.76-1.14 (m, 18H)

Intermediate 72

(3R)-1-azabicyclo[2.2.2]oct-3-yl 1-[3-(3-hydroxyprop-1-yn-1-yl)phenyl]cyclohexanecarboxylate To a suspension of (3R)-1-azabicyclo[2.2.2]oct-3-yl 1-(3-bromophenyl)cyclohexane carboxylate (Intermediate 3, 800 mg, 2.04 mmol) in diisopropylamine (6 mL) was added prop-2-yn-1-ol (229 mg, 4.08 mmol) and copper iodide (79 mg, 0.41 mmol) and the reaction mixture was placed under argon atmosphere. Then, tetrakis(triphenylphosphine)palladium (238 mg, 0.21 mmol) was added and the mixture was purged with argon and heated to 100° C. for 2 h. Then, chloroform was added (30 mL) and the mixture was filtered through a pad of Celite®, and the filtrate was concentrated to dryness. The crude residue was purified by column chromatography over silica gel using a gradient of Chloroform/Chloroform:Methanol:Ammonia (40:4:0.2) as eluent. The title compound was obtained as a brownish oil (810 mg of a 93% purity, 97%).

LRMS (m/z): 368 (M+1)+

Intermediate 73

(3R)-1-azabicyclo[2.2.2]oct-3-yl 1-[3-(3-hydroxypropyl)phenyl]cyclohexane carboxylate Obtained as a pale yellow oil (1.57 g of a 93% purity, 67%) from (3R)-1-azabicyclo[2.2.2]oct-3-yl 1-[3-(3-hydroxyprop-1-yn-1-yl)phenyl]cyclohexanecarboxylate (Intermediate 72, 2.25 g, 6.12 mmol) and palladium on carbon (620 mg of a 10% by weight, 0.58 mmol) in a mixture of acetic acid (58 mL) and THF (73 mL), under 23 psi of hydrogen atmosphere, following the experimental procedure described for the synthesis of Intermediate 7. The crude residue was purified by column chromatography over silica gel using a gradient of Chloroform/Chloroform:Methanol:Ammonia (40:4:0.2) as eluent.

LRMS (m/z): 372 (M+1)+

Intermediate 74

(3R)-1-azabicyclo[2.2.2]oct-3-yl 1-[3-(3-{[(2-chloro-4-formyl-5-methoxyphenoxy)acetyl]oxy}propyl)phenyl]cyclohexanecarboxylate To a suspension of (2-chloro-4-formyl-5-methoxyphenoxy)acetic acid (Intermediate 32, 99 mg, 0.40 mmol) in chloroform (5 mL) were added, under argon atmosphere, 2 drops of DMF and a solution of oxalyl chloride (40 μL, 0.46 mmol) in chloroform (0.5 mL). After 1 hour of stirring at r.t. additional solution of oxalyl chloride (40 μL, 0.46 mmol) in chloroform (0.5 mL) was added and the reaction mixture was stirred for an additional hour. Then, a solution of (3R)-1-azabicyclo[2.2.2]oct-3-yl 1-[3-(3-hydroxypropyl)phenyl]cyclohexanecarboxylate (150 mg, 0.4 mmol) in chloroform (1 mL) was added, and the reaction mixture was stirred a r.t. for 2 hours and at 50° C. for an additional 20 hours. The mixture was diluted with more chloroform (15 mL) and 4% aqueous sodium bicarbonate solution was added keeping vigorous stirring for 30 min. The phases were then separated and the aqueous phase was further extracted with chloroform (2×30 mL). The combined organic extracts were washed with water and brine (30 mL each), filtered and concentrated under reduced pressure to yield the title compound (158 mg, 65%) as a yellowish oil. This was used in the next synthetic step without any further purification.

LRMS (m/z): 598 (M+1)+

Intermediate 75

(3R)-1-azabicyclo[2.2.2]oct-3-yl 1-{3-[3-({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}oxy)propyl]phenyl}cyclohexanecarboxylate Obtained as a pale yellow foam (78 mg, 16%) from (3R)-1-azabicyclo[2.2.2]oct-3-yl 1-[3-(3-{[(2-chloro-4-formyl-5-methoxyphenoxy)acetyl]oxy}propyl)phenyl]cyclohexane carboxylate (Intermediate 74, 323 mg, 0.54 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 213 mg, 0.54 mmol) and sodium triacetoxyborohydride (345 mg, 1.63 mmol) following the experimental procedure described for the synthesis of Intermediate 15. Purification was performed by reverse phase column chromatography over C18 modified silica gel using a gradient of Water/Acetonitrile.

LRMS (m/z): 917 (M+1)+

Example 10

(3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}oxy)propyl]phenyl}cyclohexanecarboxylate Obtained as a pale beige solid (35 mg as a dihydrofluoride salt, 48%) from (3R)-1-azabicyclo[2.2.2]oct-3-yl 1-{3-[3-({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}oxy)propyl]phenyl} cyclohexanecarboxylate (Intermediate 75, 75 mg, 0.082 mmol) and triethylamine trihydrofluoride (53 μL, 0.33 mmol) following the experimental procedure described for the synthesis of Example 1.

LRMS (m/z): 803 (M+1)+

1H NMR (300 MHz, dmso) δ 8.09 (d, 1H), 7.28-7.16 (m, 4H), 7.03-7.01 (m, 2H), 6.88 (d, 1H), 6.69 (s, 1H), 6.45 (d, 1H), 5.02 (dd, 1H), 4.95 (s, 2H), 4.67-4.64 (m, 1H), 4.08 (t, 2H), 3.72 (s, 3H), 3.63 (s, 2H), 3.06-2.99 (m 1H), 2.70-2.31 (cs, 10H), 1.90-1.21 (m, 16H)

Intermediate 76

5-aminopyridine-2-carboxylic acid

A solution of 5-amino-2-cyanopyridine (10.0 g, 83.9 mmol) in sulfuric acid (50 mL) was placed in a high pressure vessel and heated to 90° C. for 2 h. Then, water was added to the mixture (100 mL) and the reaction was heated to 100° C. for 2 additional hours. The obtained orange solution was poured over a mixture of ice and water and stirring was maintained for 15 min (a pale beige solid precipitated from the solution) and the solid obtained was filtered, washed with cold water and dried under vacuum overnight to afford the title compound (11.7 g, 100%)

LRMS (m/z): 139 (M+1)+

Intermediate 77 ethyl 5-aminopyridine-2-carboxylate 5-aminopyridine-2-carboxylic acid (Intermediate 76, 11.6 g, 84.0 mmol) was added to a solution of hydrochloric acid (250 mL of a 1.25 M solution in ethanol) and the mixture was heated to 65° C. for four days. Upon complete consumption of the starting material, the solvent was evaporated and the residue was suspended in water (300 mL). Solid potassium carbonate was added to the mixture until pH=8 was reached and the aqueous phase was extracted with ethyl acetate (3×300 mL). The combined organic extracts were washed with brine (500 mL), dried and concentrated under reduced pressure to afford the title compound (10 g, 72%) as an orange solid.

LRMS (m/z): 167 (M+1)+

Intermediate 78

(5-aminopyridin-2-yl)methanol

Lithium aluminium hydride (325 mg, 8.57 mmol) was suspended in THF (4 mL) and cooled to 0° C. To this suspension, a solution of ethyl 5-aminopyridine-2-carboxylate (Intermediate 77, 470 mg, 2.83 mmol) in THF (17 mL) was added dropwise and the reaction mixtures was stirred for 4 hours a r.t. The reaction mixture was then treated with sequential addition of water (325 μL), 4N aqueous sodium hydroxide (325 μL) and water (975 μL), and the suspension was filtered through a pad of Celite® washing with dichloromethane. The solvent was remove in vacuo to give the title compound as colorless foam (329 mg, 94%).

LRMS (m/z): 125 (M+1)+

Intermediate 79

6-({[tert-butyl(dimethyl)silyl]oxy}methyl)pyridin-3-amine

To a solution of (5-aminopyridin-2-yl)methanol (Intermediate 78, 1.28 g, 10.3 mmol) in DMF (50 mL) was added portionwise imidazole (2.11 g, 31.0 mmol) and the solution was cooled to 0° C. To this solution, tert-butyldimethylsilylchloride (3.11 g, 20.6 mmol) was added portionwise and stirring was maintained at 0° C. for 10 min and 3 hours at r.t. The solvent was evaporated and diethyl ether (40 mL) was added to the crude residue. Water was added to the mixture and the phases were separated. The aqueous phase was extracted with diethyl ether (2×10 mL) and the combined organic extracts were washed with 4% aqueous solution of sodium bicarbonate and brine, dried, filtered and concentrated to dryness. The crude residue was purified by column chromatography over silica gel eluting with a gradient of Hexane/Ethyl acetate to yield the title compound (1.41 g, 57%) as a colorless oil.

LRMS (m/z): 239 (M+1)+

Intermediate 80

(3R)-1-azabicyclo[2.2.2]oct-3-yl 1-[3-(4-{[6-({[tert-butyl(dimethyl)silyl]oxy}methyl)pyridin-3-yl]amino}-4-oxobutyl)phenyl]cyclohexanecarboxylate Obtained as a pale brown oil (825 mg of a 68% purity, 90%) from 4-[3-(1-{[(3R)-1-azabicyclo[2.2.2]oct-3-yloxy]

carbonyl}cyclohexyl)phenyl]butanoic acid (Intermediate 11, 518 mg, 1.0 mmol), 6-({[tert-butyl(dimethyl)silyl]oxy}methyl)pyridin-3-amine (Intermediate 79, 103 mg, 0.47 mmol), DIEA (220 µL, 1.26 mmol) and HATU (460 mg, 1.21 mmol) in chloroform (8 mL) following the experimental procedure described for the synthesis of Intermediate 12. The crude obtained was used without any further purification.

LRMS (m/z): 621 (M+1)+

Intermediate 81

(3R)-1-azabicyclo[2.2.2]oct-3-yl 1-[3-(4-{[6-(hydroxymethyl)pyridin-3-yl]amino}-4-oxobutyl)phenyl]cyclohexanecarboxylate To a solution of (3R)-1-azabicyclo[2.2.2]oct-3-yl 1-[3-(4-{[6-({[tert-butyl(dimethyl)silyl]oxy}methyl)pyridin-3-yl]amino}-4-oxobutyl)phenyl]cyclohexane carboxylate (Intermediate 80, 825 mg of a 68% purity, 0.90 mmol) in THF (8 mL) was added dropwise a solution of tetrabutylammonium fluoride (1.1 mL of a 1M solution in THF, 1.1 mmol) and stirring was kept at r.t. for 1.5 hours. The, water (40 mL) and chloroform (40 mL) were added to the reaction mixture and the phases were separated. The aqueous phase was extracted further with chloroform (3×40 mL) and the resulting organic phase was washed with water and brine, dried, filtered and concentrated to dryness to afford the title compound (695 mg of an 86% purity, quantitative) as a brownish foam.

LRMS (m/z): 507 (M+1)+

Intermediate 82

(3R)-1-azabicyclo[2.2.2]oct-3-yl 1-(3-{4-[(6-formyl pyridin-3-yl)amino]-4-oxobutyl}phenyl)cyclohexanecarboxylate Obtained as a yellow oil (794 mg of a 57% purity, 100%) from (3R)-1-azabicyclo[2.2.2]oct-3-yl 1-[3-(4-{[6-(hydroxymethyl)pyridin-3-yl]amino}-4-oxobutyl)phenyl]cyclohexanecarboxylate (Intermediate 81, 695 mg of an 86% purity, 0.90 mmol) and Dess-Martin periodinane reagent (701 mg, 1.65 mmol) in chloroform (12 mL), following the experimental procedure described for the synthesis of Intermediate 14. The crude residue was used without purification.

LRMS (m/z): 505 (M+1)+

Intermediate 83

(3R)-1-azabicyclo[2.2.2]oct-3-yl 1-[3-(4-{[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]amino}-4-oxobutyl)phenyl]cyclohexane carboxylate Obtained as a pale yellow foam (633 mg, 81%) from (3R)-1-azabicyclo[2.2.2]oct-3-yl 1-(3-{4-[(6-formylpyridin-3-yl)amino]-4-oxobutyl}phenyl)cyclohexanecarboxylate (Intermediate 82, 794 mg of a 57% purity, 0.90 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 405 mg, 1.03 mmol) and sodium triacetoxyborohydride (500 mg, 2.36 mmol) following the experimental procedure described for the synthesis of Intermediate 15. Purification was performed by column chromatography over silica gel using a gradient of Chloroform/Methanol.

LRMS (m/z): 823 (M+1)+; 412 (M/2+1)+

Example 11

(3R)-1-azabicyclo[2.2.2]oct-3-yl 1-[3-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)phenyl]cyclohexanecarboxylate Obtained as a pale beige solid (400 mg as a dihydrofluoride salt, 69%) from (3R)-1-azabicyclo[2.2.2]oct-3-yl 1-[3-(4-{[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]amino}-4-oxobutyl)phenyl]cyclohexanecarboxylate (Intermediate 83, 633 mg, 0.77 mmol) and triethylamine trihydrofluoride (140 µL, 0.86 mmol) following the experimental procedure described for the synthesis of Example 1.

LRMS (m/z): 709 (M+1)+

1H NMR (300 MHz, dmso) δ 10.1 (s, 1H), 8.68 (d, 1H), 8.15 (d, 1H), 7.98 (dd, 1H), 7.34 (d, 1H), 7.28-7.18 (m, 3H), 7.08-7.04 (m, 2H), 6.90 (d, 1H), 6.48 (d, 1H), 5.17 (dd, 1H), 4.75-4.72 (m, 1H), 3.93 (s, 2H), 3.14 (dd, 1H), 2.79-2.28 (m, 12H), 1.87-1.82 (m, 2H), 1.79-1.19 (m, 14H)

Intermediate 84

(3R)-1-azabicyclo[2.2.2]oct-3-yl 1-(3-{3-[[2-chloro-4-(hydroxymethyl)-5-methoxybenzoyl](methyl)amino]propyl}phenyl)cyclohexanecarboxylate Obtained as a colorless oil (100 mg, 56%) from (3R)-1-azabicyclo[2.2.2]oct-3-yl 1-{3-[3-(methylamino)propyl]phenyl}cyclohexanecarboxylate (Intermediate 24, 118 mg, 0.31 mmol), 2-chloro-4-(hydroxymethyl)-5-methoxybenzoic acid (Intermediate 68, 67 mg, 0.31 mmol), DIEA (81 µL, 0.46 mmol) and HATU (175 mg, 0.46 mmol) in DMF (3 mL) following the experimental procedure described for the synthesis of Intermediate 12. Purification was performed by column chromatography over silica gel using a gradient of Chloroform/Methanol from 50/1 to 4/1.

LRMS (m/z): 584 (M+1)+

Intermediate 85

(3R)-1-azabicyclo[2.2.2]oct-3-yl 1-(3-{3-[(2-chloro-4-formyl-5-methoxybenzoyl)(methyl)amino]propyl}phenyl)cyclohexanecarboxylate Obtained as a pale white oil (794 mg of a 57% purity, 100%) from (3R)-1-azabicyclo[2.2.2]oct-3-yl 1-(3-{3-[[2-chloro-4-(hydroxymethyl)-5-methoxybenzoyl](methyl)amino]propyl}phenyl)cyclohexanecarboxylate (Intermediate 84, 130 mg, 0.22 mmol) and Dess-Martin periodinane reagent (109 mg, 0.26 mmol) in chloroform (3 mL), following the experimental procedure described for the synthesis of Intermediate 14. Purification was performed by column chromatography over silica gel using a gradient of Chloroform/Methanol from 50/1 to 4/1.

LRMS (m/z): 582 (M+1)+

Intermediate 86

(3R)-1-azabicyclo[2.2.2]oct-3-yl 1-(3-{3-[[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl](methyl)amino]propyl}phenyl)cyclohexanecarboxylate Obtained as a pale yellow oil (75 mg of an 89% purity, 58%) from (3R)-1-azabicyclo[2.2.2]oct-3-yl 1-(3-{4-[(6- formylpyridin-3-yl)amino]-4-oxobutyl}phenyl)cyclohexanecarboxylate (Intermediate 85, 75 mg, 0.13 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 51 mg, 0.13 mmol) and sodium triacetoxyborohydride (103 mg, 0.49 mmol) following the experimental procedure described for the synthesis of Intermediate 15. Purification was performed by column chromatography over silica gel using a gradient of Chloroform/Methanol from 50/1 to 4/1.

LRMS (m/z): 900 (M+1)+; 898 (M−1)−

Example 12

(3R)-1-azabicyclo[2.2.2]oct-3-yl 1-(3-{3-[[2-chloro-4-({[(2R)-2-hydroxy-2-(8-hydroxy-2-oxo-1,2-dihydroquinolin-5-yl)ethyl]amino}methyl)-5-methoxybenzoyl](methyl)amino]propyl}phenyl)cyclohexanecarboxylate Obtained as a pale beige foam (34 mg as the free base, 58%) from (3R)-1-azabicyclo[2.2.2]oct-3-yl 1-(3-{3-[[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl](methyl)amino]propyl}phenyl)cyclohexanecarboxylate (Intermediate 86, 74 mg, 0.082 mmol) and triethylamine trihydrofluoride (67 µL, 0.41 mmol) following the experimental procedure described for the synthesis of Example 1. Purification was performed by column chromatography over silica gel using a gradient of Chloroform/Methanol from 50/1 to 4/1 followed by Chloroform/Methanol/Ammonia 9:1:0.1 to 4:1:0.1.

LRMS (m/z): 786 (M+1)+

1H NMR (300 MHz, dmso) δ 8.29 (s, 1H), 8.11 (d, 1H), 7.31-7.02 (m, 5H), 6.89-6.85 (m, 2H), 6.45 (d, 1H), 5.40-5.30 (bs, 1H), 5.01 (dd, 1H), 4.70-4.53 (m, 1H), 3.80-3.55 (m, 7H), 3.03-2.98 (m, 1H), 2.95 (s, 3H), 2.75-2.24 (m, 12H), 1.88-1.21 (m, 14H)

Intermediate 87

Methyl 2-chloro-4-(hydroxymethyl)-5-methoxybenzoate 2-chloro-4-(hydroxymethyl)-5-methoxybenzoic acid (Intermediate 68, 490 mg, 2.26 mmol) was dissolved in a solution of hydrogen chloride in methanol (5.6 mL of a 1.25M solution of HCl, in MeOH) and the mixture was stirred at 65° C. in a sealed tube. The solvent was the removed under reduced pressure and the residue was treated with methanol and evaporated to dryness two times to yield the title compound (517 mg, 95%) as a colorless oil.

LRMS (m/z): 231 (M+1)+

Intermediate 88

Methyl 2-chloro-4-formyl-5-methoxybenzoate

Obtained as a pale yellow solid (393 mg, 64%) from methyl 2-chloro-4-(hydroxymethyl)-5-methoxybenzoate (Intermediate 87, 515 mg, 2.23 mmol) and Dess-Martin periodinane reagent (1.14 g, 2.69 mmol) in dichloromethane (28 mL), following the experimental procedure described for the synthesis of Intermediate 14. The compound was used without any further purification.

LRMS (m/z): 229 (M+1)+

Intermediate 89

2-chloro-4-formyl-5-methoxybenzoic acid

To a solution of methyl 2-chloro-4-formyl-5-methoxybenzoate (Intermediate 88, 180 mg, 0.79 mmol) in THF (6 mL) was added dropwise a solution of lithium hydroxide monohydrate (70 mg, 1.67 mmol) in water (6 mL). The reaction mixture was stirred at r.t. overnight and then, the organic solvent was evaporated, water (4 mL) was added, and the aqueous phase was washed with diethyl ether (20 mL). The aqueous phase was then acidified, at 0° C., with 5N aqueous hydrochloric acid until a pH=3 was reached, and it was extracted with diethyl ether (3×20 mL). The combined organic extracts were washed with water and brine (20 ml each), filtered and concentrated to dryness to afford the title compound (164 mg, 92%) as a yellow solid.

LRMS (m/z): 213 (M−1)−

Intermediate 90

3-[3-(1-{[(3R)-1-azabicyclo[2.2.2]oct-3-yloxy]carbonyl}cyclohexyl)phenyl]propyl 2-chloro-4-formyl-5-methoxybenzoate Obtained as a yellowish foam (90 mg, 40%) from (3R)-1-azabicyclo[2.2.2]oct-3-yl 1-[3-(3-hydroxypropyl)phenyl]cyclohexane carboxylate (Intermediate 73, 97 mg, 0.26 mmol), 2-chloro-4-formyl-5-methoxybenzoic acid (Intermediate 89, 56 mg, 0.26 mmol), oxalyl chloride (25 µL, 0.29 mmol) and 1 drop of DMF in chloroform (4.5 mL), following the experimental procedure described for the synthesis of Intermediate 74. The crude was used without any further purification.

LRMS (m/z): 569 (M+1)+; 615 (M of dimethylacetal+1)+

Intermediate 91

3-[3-(1-{[(3R)-1-azabicyclo[2.2.2]oct-3-yloxy]carbonyl}cyclohexyl)phenyl]propyl 4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoate Obtained as a pale yellow oil (99 mg, 63%) from 3-[3-(1-{[(3R)-1-azabicyclo[2.2.2]oct-3-yloxy]carbonyl}cyclohexyl)phenyl]propyl 2-chloro-4-formyl-5-methoxybenzoate (Intermediate 90, 90 mg, 0.16 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 62.5 mg, 0.16 mmol) and sodium triacetoxyborohydride (111 mg, 0.52 mmol) following the experimental procedure described for the synthesis of Intermediate 15. Purification was performed by reverse phase column chromatography over C18 modified silica gel using a gradient of Water/Acetonitrile.

LRMS (m/z): 889 (M+1)+; 445 (M/2+1)+; 887 (M−1)−

Example 13

3-[3-(1-{[(3R)-1-azabicyclo[2.2.2]oct-3-yloxy]carbonyl}cyclohexyl)phenyl]propyl 2-chloro-4-({[(2R)-2-hydroxy-2-(8-hydroxy-2-oxo-1,2-dihydroquinolin-5-yl)ethyl]amino}methyl)-5-methoxybenzoate Obtained as a pale beige foam (26 mg as a dihydrofluoride salt, 23%) from 3-[3-(1-{[(3R)-1-azabicyclo[2.2.2]oct-3- yloxy]carbonyl}cyclohexyl)phenyl]propyl 4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoate (Intermediate 91, 95 mg, 0.11 mmol) and triethylamine trihydrofluoride (70 µL, 0.43 mmol) following the experimental procedure described for the synthesis of Example 1. No purification was performed for this example.

LRMS (m/z): 773 (M+1)+

1H NMR (300 MHz, dmso) δ 10.37 (bs, 1H), 8.16 (s, 1H), 7.61 (s, 1H), 7.32-7.03 (cs, 6H), 6.93 (s, 1H), 6.47 (d, 1H), 5.24 (dd, 1H), 4.90-4.70 (m, 1H), 4.25-4.19 (m, 2H), 4.05-3.82 (m, 2H), 3.82 (s, 3H), 2.88-2.70 (cs, 9H), 2.35-2.25 (m, 2H), 2.05-1.87 (m, 2H), 2.25-1.20 (cs, 14H).

Intermediate 92

Tert-butyl(dimethyl)[(4-methylenecyclohexyl)oxy]silane

Butyl lithium (1.55 mL of a 1.6M solution in hexanes, 2.48 mmol) was added over a suspension of methyltriphenylphosphonium bromide (0.85 g, 2.38 mmol) in THF (5 mL), at 0° C. and under argon atmosphere. The reaction mixture was allowed to warm up to r.t. and, after 30 min, a solution of 4-(tert-butyldimethylsilyloxy)cyclohexanone (0.50 mL, 1.99 mmol) in THF (5 mL) and stirring was maintained at r.t. for 20 hours. The reaction mixture was then filtered through a 4µ PTFE membrane, washed with hexanes and the filtrate was concentrated to dryness to afford the title compound (412 mg, 94%) as a pale yellow oil.

1H NMR (300 MHz, cd3od) δ 4.59 (s, 2H), 3.88 (ddd, J=11.2, 7.5, 3.5 Hz, 1H), 2.45-2.24 (m, 2H), 2.05 (ddd, J=13.4, 9.2, 4.4 Hz, 2H), 1.75 (ddd, J=15.4, 7.4, 3.6 Hz, 2H), 1.58-1.38 (m, 2H), 0.90 (s, 9H), 0.07 (s, 6H).

Intermediate 93

(3R)-1-azabicyclo[2.2.2]oct-3-yl 1-{3-[(4-{[tert-butyl(dimethyl)silyl]oxy}cyclohexylidene)methyl]phenyl}cyclohexanecarboxylate Obtained as a pale beige solid (239 mg, 77%) from (3R)-1-azabicyclo[2.2.2]oct-3-yl 1-(3-bromophenyl)cyclohexanecarboxylate (Intermediate 3, 210 mg, 0.54 mmol), tert-butyl(dimethyl)[(4-methylenecyclohexyl)oxy]silane (Intermediate 92, 124 mg, 0.55 mmol), tri-ortho-tolylphosphine (66 mg, 0.22 mmol), DIEA (160 µL, 0.92 mmol) and palladium acetate (25 mg, 0.11 mmol) in acetonitrile (3 mL), following the experimental procedure described for the synthesis of Intermediate 6. Purification of the crude residue was performed by column chromatography over silica gel using as a gradient a mixture of eluents Hexane:Chloroform:Methanol.

LRMS (m/z): 539 (M+1)+

Intermediate 94

(3R)-1-azabicyclo[2.2.2]oct-3-yl 1-{3-[(trans-4-{[tert-butyl(dimethyl)silyl]oxy}cyclohexyl)methyl]phenyl}cyclohexanecarboxylate Obtained as a pale yellow solid (106 mg of a mixture cis/trans, 49%) from (3R)-1-azabicyclo[2.2.2]oct-3-yl 1-{3-[(4-{[tert-butyl(dimethyl)silyl]oxy}cyclohexylidene)methyl]phenyl}cyclohexanecarboxylate (Intermediate 93, 215 mg, 0.40 mmol) and palladium on carbon (20 mg of a 10% by weight, 0.011 mmol) in acetic acid (1.8 mL) and THF (1.8 mL), following the experimental procedure described for the synthesis of Intermediate 7. The crude product was purified initially by column chromatography over silica gel using a gradient of Chloroform:Ethanol.

LRMS (m/z): 541 (M+1)+

Intermediate 95

(3R)-1-azabicyclo[2.2.2]oct-3-yl 1-{3-[(trans-4-hydroxycyclohexyl)methyl]phenyl}cyclohexanecarboxylate Obtained as viscous brownish oil (97 mg, 99%) from (3R)-1-azabicyclo[2.2.2]oct-3-yl 1-{3-[(trans-4-{[tert-butyl(dimethyl)silyl]oxy}cyclohexyl)methyl]phenyl}cyclohexane carboxylate (Intermediate 94, 106 mg, 0.20 mmol) and tetrabutylammonium fluoride (2164 of a 1M solution in THF, 0.22 mmol) in THF (3 mL) following the experimental procedure described for the synthesis of Intermediate 81. The compound was used without any further purification.

LRMS (m/z): 427 (M+1)+

Intermediate 96

(3R)-1-azabicyclo[2.2.2]oct-3-yl 1-{3-[(trans-4-{[(2-chloro-4-formyl-5-methoxyphenoxy)acetyl]oxy}cyclohexyl)methyl]phenyl}cyclohexanecarboxylate To a solution of (3R)-1-azabicyclo[2.2.2]oct-3-yl 1-{3-[(trans-4-hydroxycyclohexyl)methyl]phenyl} cyclohexanecarboxylate (Intermediate 95, 95 mg, 0.22 mmol) in chloroform (3 mL) were sequentially added DIEA (120 µL, 0.69 mmol) and HATU (135 mg, 0.36 mmol) and the mixture was stirred at r.t. for 20 min. Then, (2-chloro-4-formyl-5-methoxyphenoxy)acetic acid (Intermediate 32, 55 mg, 0.22 mmol) was added and the reaction mixture was stirred for 16 hours. Chloroform and water were added to the mixture (15 mL each) and 4% aqueous sodium bicarbonate solution was added and stirring maintained for an additional hour. The phases were separated and the aqueous phase was extracted with chloroform (2×15 mL). The resulting organic phase was washed with water and brine, dried over anhydrous sodium sulphate, filtered and concentrated to dryness to afford the title compound (147 mg, 91%) as a yellowish foam. No additional purification was performed in this step.

LRMS (m/z): 653 (M+1)+

Intermediate 97

(3R)-1-azabicyclo[2.2.2]oct-3-yl 1-(3-{[trans-4-({[4-({[(2R)-2-{[tert-butyl(dimethyl) silyl]oxy}-2-(8-hydroxy-2-oxo-1,2-dihydroquinolin-5-yl)ethyl]amino}methyl)-2-chloro-5-methoxyphenoxy]acetyl}oxy)cyclohexyl]methyl}phenyl)cyclohexane carboxylate Obtained as a pale yellow oil (80 mg, 41%) from (3R)-1-azabicyclo[2.2.2]oct-3-yl 1-{3-[(trans-4-{[(2-chloro-4-formyl-5-methoxyphenoxy)acetyl]oxy}cyclohexyl)methyl]phenyl}cyclohexanecarboxylate (Intermediate 96, 145 mg, 0.22 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 67 mg, 0.20 mmol) and sodium triacetoxyborohydride (170 mg, 0.80 mmol), following the experimental procedure described for the synthesis of Intermediate 15. Purification was performed by column chromatography over silica gel using a gradient of Chloroform/Ethanol.
LRMS (m/z): 971 (M+1)+; 486 (M/2+1)+

Example 14

(3R)-1-azabicyclo[2.2.2]oct-3-yl 1-(3-{[4-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}oxy)cyclohexyl]methyl}phenyl)cyclohexanecarboxylate Obtained as a pale beige foam (43 mg as a dihydrofluoride salt, 50%) from (3R)-1-azabicyclo[2.2.2]oct-3-yl 1-(3-{[trans-4-({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}oxy)cyclohexyl]methyl}phenyl)cyclohexanecarboxylate (Intermediate 97, 80 mg, 0.082 mmol) and triethylamine trihydrofluoride (40 μL, 0.24 mmol), following the experimental procedure described for the synthesis of Example 1. No purification was performed for this example.
LRMS (m/z): 857 (M+1)+; 429 (M/2+1)+
1H NMR (300 MHz, dmso) δ 10.6-10.2 (bs, 1H), 8.11 (d, 1H), 7.41-6.87 (cs, 7H), 6.75 (s, 1H), 6.54 (d, 1H), 5.12 (dd, 1H), 5.01 (s, 2H), 4.75-4.66 (m, 1H), 3.78-3.72 (cs, 6H), 3.15-3.05 (m, 1H), 2.77-2.60 (cs, 5H), 2.40-2.24 (cs, 4H), 1.80-0.94 (cs, 23H)

Intermediate 98

Methyl 6-(hydroxymethyl)nicotinate

To a solution of methyl-6-(acetoxymethyl)nicotinate (Prepared according to the experimental procedure described in Dalton et. al. *J. Heterocyclic. Chem.* 1995, 32, 665; 4.0 g, 19.2 mmol) in methanol (20 mL) was added, under inert atmosphere, a solution of hydrochloric acid in methanol (20 mL of a 1.25M solution in methanol) and stirring was maintained for 2 days. The organic solvent was removed and 4% aqueous sodium bicarbonate solution was added until pH=8 was reached. The aqueous phase was extracted with ethyl acetate (3×100 mL) and the combined organic phases were washed with brine and concentrated to yield the title compound (2.83 g of a 90% purity, 80%) as a brown solid.
LRMS (m/z): 168 (M+1)+

Intermediate 99 methyl 6-({[tert-butyl(dimethyl)silyl]oxy}methyl)nicotinate

Obtained as a pale beige solid (1.66 g of an 85% purity, 93%) from methyl 6-(hydroxymethyl)nicotinate (Intermediate 98, 1.0 g, 5.98 mmol), tert-butyldimethylsilylchloride (1.12 g, 16.45 mmol) and imidazole (1.62 g, 10.75 mmol) in DMF (32 mL), following the experimental procedure described for the synthesis of Intermediate 79, using ethyl acetate for the extraction step.
LRMS (m/z): 282 (M+1)+

Intermediate 100

6-({[tert-butyl(dimethyl)silyl]oxy}methyl)nicotinic acid

Obtained as a white foam (118 mg, 66%) from methyl 6-({[tert-butyl(dimethyl)silyl]oxy}methyl)nicotinate (Intermediate 99, 208 mg, 0.74 mmol) and lithium hydroxide monohydrate (29 mg, 0.69 mmol) following the experimental procedure described for the synthesis of Intermediate 89. No further purification was performed in this case.
LRMS (m/z): 266 (M−1)−

Intermediate 101

3-[3-(1-{[(3R)-1-azabicyclo[2.2.2]oct-3-yl oxy]carbonyl}cyclohexyl)phenyl]propyl 6-({[tert-butyl(dimethyl)silyl]oxy}methyl)nicotinate Obtained as a colorless oil (71 mg, 47%) from 6-({[tert-butyl(dimethyl)silyl]oxy}methyl)nicotinic acid (Intermediate 100, 65 mg, 0.24 mmol), (3R)-1-azabicyclo[2.2.2]oct-3-yl 1-[3-(3-hydroxypropyl)phenyl]cyclohexanecarboxylate (Intermediate 73, 97 mg, 0.26 mmol), DIEA (171 μL, 0.98 mmol) and HATU (148 mg, 0.39 mmol) following the experimental procedure described for the synthesis of Intermediate 96. Purification was performed by column chromatography over silica gel using a gradient of Chloroform/Methanol from 50/1 to 25/1.
LRMS (m/z): 622 (M+1)+

Intermediate 102

3-[3-(1-{[(3R)-1-azabicyclo[2.2.2]oct-3-yl oxy]carbonyl}cyclohexyl)phenyl]propyl 6-(hydroxymethyl)nicotinate Obtained as a colorless oil (43 mg, 72%) from 3-[3-(1-{[(3R)-1-azabicyclo[2.2.2]oct-3-yloxy]carbonyl}cyclohexyl)phenyl]propyl 6-({[tert-butyl(dimethyl)silyl]oxy}methyl) nicotinate (Intermediate 101, 70 mg, 0.11 mmol) and triethylamine trihydrofluoride complex (69 μL, 0.42 mmol) in THF (2 mL), following the experimental procedure described for the synthesis of Intermediate 13. The compound was used without any further purification.
LRMS (m/z): 508 (M+1)+

Intermediate 103

3-[3-(1-{[(3R)-1-azabicyclo[2.2.2]oct-3-yl oxy]carbonyl}cyclohexyl)phenyl]propyl 6-formylnicotinate Obtained as a colorless oil (33 mg of an 80% purity, 62%) from (3-[3-(1-{[(3R)-1-azabicyclo[2.2.2]oct-3-yloxy]carbonyl}cyclohexyl)phenyl]propyl 6-(hydroxymethyl) nicotinate (Intermediate 102, 43 mg, 0.085 mmol) and Dess-Martin periodinane reagent (42 mg, 0.10 mmol) in chloroform (0.9 mL), following the experimental procedure described for the synthesis of Intermediate 14. Purification was performed by column chromatography over silica gel using a gradient of Chloroform/Methanol from 50/1 to 15/1.
LRMS (m/z): 506 (M+1)+; 538 (M of dimethylacetal+1)+

Intermediate 104

3-[3-(1-{[(3R)-1-azabicyclo[2.2.2]oct-3-yloxy]carbonyl}cyclohexyl)phenyl] propyl 6-({[(2R)-2-{[tert-butyl(dimethyl)silyl]oxy}-2-(8-hydroxy-2-oxo-1,2-dihydroquinolin-5-yl)ethyl]amino}methyl) nicotinate Obtained as a pale yellow oil (52 mg, 71%) from 3-[3-(1-{[(3R)-1-azabicyclo[2.2.2]oct-3-yloxy]

carbonyl}cyclohexyl)phenyl]propyl 6-formylnicotinate (Intermediate 103, 53 mg of an 80% purity, 0.84 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 67 mg, 0.20 mmol) and sodium triacetoxyborohydride (33 mg, 0.084 mmol), following the experimental procedure described for the synthesis of Intermediate 15. Purification was performed by column chromatography over silica gel using a gradient of Chloroform/Methanol from 50/1 to 4/1.

LRMS (m/z): 824 (M+1)+

Example 15

3-[3-(1-{[(3R)-1-azabicyclo[2.2.2]oct-3-yloxy]carbonyl}cyclohexyl)phenyl]propyl 6-({[(2R)-2-hydroxy-2-(8-hydroxy-2-oxo-1,2-dihydroquinolin-5-yl)ethyl]amino}methyl)nicotinate Obtained as a pale beige foam (43 mg as a dihydrofluoride salt, 50%) from 3-[3-(1-{[(3R)-1-azabicyclo[2.2.2]oct-3-yloxy]carbonyl}cyclohexyl)phenyl] propyl 6-({[(2R)-2-{[tert-butyl(dimethyl)silyl]oxy}-2-(8-hydroxy-2-oxo-1,2-dihydroquinolin-5-yl)ethyl]amino}methyl)nicotinate (Intermediate 104, 51 mg, 0.062 mmol) and triethylamine trihydrofluoride (50 µL, 0.31 mmol), following the experimental procedure described for the synthesis of Example 1. No purification was performed for this example.

LRMS (m/z): 710 (M+1)+
$^1$H NMR (300 MHz, DMSO-d$_6$) δ: 1.15-1.45 (m, 7H), 1.45-1.70 (m, 6H), 1.82 (m, 1H), 1.95-2.10 (m, 2H), 2.25-2.45 (m, 3H), 2.55-2.80 (m, 5H), 2.85-2.95 (m, 1H), 3.05-3.15 (m, 2H), 3.98 (s, 2H), 4.26 (t, 2H), 4.70 (m, 1H), 5.13 (m, 1H), 6.47-6.51 (d, J=10 Hz, 1H), 6.91 (d, J=8 Hz, 1H), 7.08 (d, J=8 Hz, 1H), 7.13-7.30 (m, 4H), 7.57 (d, 1H), 8.15-8.19 (d, J=10 Hz, 1H), 8.17-8.20 (m, 1H), 8.98 (d, J=1.8 Hz, 1H), 10.4 (broad s, 1H).

Intermediate 105

4-(2-{[tert-butyl(dimethyl)silyl]oxy}ethyl)piperidine

To a solution of 2-(piperidin-4-yl)ethanol (200 mg, 1.55 mmol) in dichloromethane (0.7 mL) was added imidazole (143 mg, 2.10 mmol) and a solution of tert-butyldimethylsilylchloride (267 mg, 1.77 mmol) in dichloromethane (1.2 mL), and the reaction was stirred at r.t. for 18 hours. The mixture was diluted with additional dichloromethane (20 mL) and the organic layer was washed with saturated aqueous potassium carbonate solution. The aqueous phase was extracted with dichloromethane (2×20 mL) and the combined organic extracts were dried over anhydrous magnesium sulphate, filtered and concentrated to dryness. The oil obtained was treated with hexane and sonicated appearing a white precipitate. The hexane was decanted and the solid was treated with additional hexane and the organic phase decanted again. The remaining white solid was dried under reduced pressure to afford 300 mg (97%) of the title compound.

LRMS (m/z): 244 (M+1)+

Intermediate 106

(3R)-1-azabicyclo[2.2.2]oct-3-yl 1-(3-{4-[4-(2-{[tert-butyl(dimethyl)silyl]oxy}ethyl) piperidin-1-yl]-4-oxobutyl}phenyl)cyclohexanecarboxylate Obtained as a colorless oil (209 mg of a 62% purity, 67%) from 4-[3-(1-{[(3R)-1-azabicyclo[2.2.2]oct-3-yloxy]carbonyl}cyclohexyl)phenyl]butanoic acid (Intermediate 11, 160 mg of the TFA salt, 0.31 mmol), 4-(2-{[tert-butyl(dimethyl)silyl]oxy}ethyl)piperidine (Intermediate 105, 87 mg, 0.36 mmol), DIEA (300 µL, 1.72 mmol) and HATU (160 mg, 0.42 mmol) following the experimental procedure described for the synthesis of Intermediate 96. The crude product was used without any further purification.

LRMS (m/z): 626 (M+1)+

Intermediate 107

(3R)-1-azabicyclo[2.2.2]oct-3-yl 1-(3-{4-[4-(2-hydroxyethyl)piperidin-1-yl]-4-oxobutyl}phenyl)cyclohexanecarboxylate Obtained as a colorless oil (87 mg, 47%) from (3R)-1-azabicyclo[2.2.2]oct-3-yl 1-(3-{4-[4-(2-{[tert-butyl(dimethyl)silyl]oxy}ethyl)piperidin-1-yl]-4-oxobutyl}phenyl) cyclohexane carboxylate (Intermediate 106, 209 mg, 0.33 mmol) and triethylamine trihydrofluoride complex (204 µL, 1.25 mmol) in THF (6 mL), following the experimental procedure described for the synthesis of Intermediate 13. Purification was performed by column chromatography over silica gel using a gradient of Chloroform/Methanol.

LRMS (m/z): 512 (M+1)+

Intermediate 108

(3R)-1-azabicyclo[2.2.2]oct-3-yl 1-(3-{4-oxo-4-[4-(2-oxoethyl)piperidin-1-yl]butyl}phenyl)cyclohexanecarboxylate Obtained as a yellow oil (91.5 mg of an 84% purity, 93%) from (3R)-1-azabicyclo[2.2.2]oct-3-yl 1-(3-{4-[4-(2-hydroxyethyl)piperidin-1-yl]-4-oxobutyl}phenyl) cyclohexanecarboxylate (Intermediate 107, 83 mg, 0.16 mmol) and Dess-Martin periodinane reagent (99 mg, 0.23 mmol) in chloroform (4 mL), following the experimental procedure described for the synthesis of Intermediate 14. No additional purification was performed on this compound.

LRMS (m/z): 510 (M+1)+

Intermediate 109

(3R)-1-azabicyclo[2.2.2]oct-3-yl 1-(3-{4-[4-(2-{[(2R)-2-{[tert-butyl(dimethyl)silyl]oxy}-2-(8-hydroxy-2-oxo-1,2-dihydroquinolin-5-yl)ethyl]amino}ethyl)piperidin-1-yl]-4-oxobutyl}phenyl)cyclohexanecarboxylate Obtained as a pale yellow oil (65 mg of an 80% purity, 53%) from (3R)-1-azabicyclo[2.2.2]oct-3-yl 1-(3-{4-oxo-4-[4-(2-oxoethyl)piperidin-1-yl]butyl}phenyl)cyclohexanecarboxylate (Intermediate 108, 87 mg of an 84% purity, 0.14 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 47 mg, 0.12 mmol) and sodium triacetoxyborohydride (107 mg, 0.50 mmol), following the experimental procedure described for the synthesis of Intermediate 15. Purification was performed by column chromatography over silica gel using a gradient of Chloroform/Methanol from 50/1 to 4/1.
LRMS (m/z): 828 (M+1)+

Example 16

(3R)-1-azabicyclo[2.2.2]oct-3-yl 1-(3-{4-[4-(2-{[(2R)-2-hydroxy-2-(8-hydroxy-2-oxo-1,2-dihydroquinolin-5-yl)ethyl]amino}ethyl)piperidin-1-yl]-4-oxobutyl}phenyl)cyclohexanecarboxylate Obtained as a pale beige foam (27 mg as a dihydrofluoride salt, 52%) from (3R)-1-azabicyclo[2.2.2]oct-3-yl 1-(3-{4-[4-(2-{[(2R)-2-{[tert-butyl(dimethyl)silyl]oxy}-2-(8-hydroxy-2-oxo-1,2-dihydroquinolin-5-yl)ethyl]amino}ethyl)piperidin-1-yl]-4-oxobutyl}phenyl)cyclohexanecarboxylate (Intermediate 109, 65 mg of an 80% purity, 0.062 mmol) and triethylamine trihydrofluoride (65 μL, 0.40 mmol), following the experimental procedure described for the synthesis of Example 1. No purification was performed for this example.
LRMS (m/z): 754 (M+1)+
$^1$H NMR (300 MHz, DMSO-d$_6$) δ: 0.80-1.05 (m, 2H), 1.15-1.30 (m, 2H), 1.30-1.50 (m, 6H), 1.50-1.77 (m, 8H), 1.77-1.82 (m, 1H), 2.22-2.30 (m, 2H), 2.30-2.46 (m, 4H), 2.55-2.70 (m, 4H), 2.70-2.95 (m, 5H), 2.97-3.10 (m, 2H), 3.70-3.80 (m, 2H), 4.33-4.38 (broad d, 1H), 4.67 (m, 1H), 5.18 (m, 1H), 6.53 (d, J=9.9 Hz, 1H), 6.91-6.94 (d, J=8.1 Hz, 1H), 7.06 (s, 1H), 7.08-7.11 (d, J=8.3 Hz, 1H), 7.15-7.30 (m, 3H), 8.19 (d, J=9.9 Hz, 1H).

Intermediate 110

5-(methylamino)pentanoic acid 1-methylpiperidin-2-one (3.88 g, 34.3 mmol) was dissolved in an aqueous hydrochloric acid solution (19 mL of a 5N solution in water) and the mixture was stirred at 130° C. overnight and 3 additional hours at 150° C. Water the was evaporated until a wet white solid was obtained. Dioxane (20 mL) was added to the mixture and evaporated to dryness (this operation was performed three more times) and the white precipitate was washed with diethyl ether (30 mL), filtered and dried at 30° C. under vacuum. The title compound was obtained (5.08 g as a hydrochloride salt, 88%) as a white solid.
LRMS (m/z): β2 (M+1)+

Intermediate 111

5-[(tert-butoxycarbonyl)(methyl)amino]pentanoic acid 5-(methylamino)pentanoic acid (Intermediate 110, 3.76 g of its hydrochloride salt, 22.4 mmol) was dissolved in a mixture of dioxane (40 mL) and water (20 mL). To this solution, an aqueous solution of sodium hydroxide (45 mL of a 1N solution, 45 mmol) was added and the mixture was cooled to 0° C. before adding di-tert-butyldicarbonate (5.4 g, 24.7 mmol) and the mixture stirred at r.t. overnight. The organic solvent was removed by rotary evaporation and the remaining aqueous phase was acidified with a 5% aqueous solution of citric acid until pH=5. The mixture was extracted with ethyl acetate (2×100 mL) and the organic extracts were washed with brine, filtered and concentrated to dryness to. The resulting colorless oil was treated with pentane and cooled to −50° C. to obtain a white precipitate. The mixture was filtered and the solid was washed with additional cold pentane to afford the title compound (4.4 g, 81%).
LRMS (m/z): 230 (M+HCOO−)−

Intermediate 112 tert-butyl (5-{[4-(hydroxymethyl)phenyl]amino}-5-oxopentyl)methylcarbamate

To a solution of 5-[(tert-butoxycarbonyl)(methyl)amino] pentanoic acid (Intermediate 111, 1.0 g, 4.32 mmol) in DMF (19.5 mL) were added DIEA (2.30 mL, 13.2 mmol) and HATU (2.10 g, 5.52 mmol) and the mixture was heated at r.t. for 1 under inert atmosphere. (4-Aminophenyl)methanol (0.59 g, 4.79 mmol) was the added and the mixture stirred for two additional hours. The reaction mixtures was poured over water (225 mL) and the aqueous phase was extracted with diethyl ether (3×150 mL) and ethyl acetate (3×150 mL). The combined organic extracts were washed with water (2×100 mL), brine (100 mL), dried and decolorized with active carbon. The mixture was filtered and the solvent was concentrated by rotary evaporation. The title compound was obtained as a yellowish solid (1.48 g of a 90% purity, 92%). This compound was used as this without any further purification.
LRMS (m/z): 337 (M+1)+

Intermediate 113 tert-butyl {5[(4-formylphenyl)amino]-5-oxopentyl}methylcarbamate

Obtained as a yellow oil (257 mg, 82%) from tert-butyl (5-{[4-(hydroxymethyl)phenyl]amino}-5-oxopentyl)methylcarbamate (Intermediate 112, 300 mg, 0.89 mmol) and Dess-Martin periodinane reagent (455 mg, 1.07 mmol) in dichloromethane (10 mL), following the experimental procedure described for the synthesis of Intermediate 14. No additional purification was performed on this compound.
LRMS (m/z): 335 (M+1)+

Intermediate 114

N-(4-formylphenyl)-5-(methylamino)pentanamide

To a solution of tert-butyl {5[(4-formylphenyl)amino]-5-oxopentyl}methylcarbamate (Intermediate 113, 256 mg, 0.77 mmol) in THF (4 mL) was added, at 0° C. and under argon atmosphere, a solution of hydrochloric acid (0.96 mL of a 4M solution in dioxane, 3.84 mmol). The mixture was allowed to arm up to r.t. and was stirred for 40 hours and finally heated for 5 additional hours to allow for reaction competition. To volatiles were evaporated and two co-evaporations with diethyl ether were performed. The title compound was obtained as a white solid (260 mg of the hydrochloride salt with an 80% purity, 99%). The compound was used without any further purification.
LRMS (m/z): 235 (M+1)+

Intermediate 115

(3R)-1-azabicyclo[2.2.2]oct-3-yl 1-(3-{4-[{5-[(4-formyl phenyl)amino]-5-oxopentyl}(methyl)amino]-4-oxobutyl}phenyl)cyclohexanecarboxylate Obtained as a colorless foam (104 mg, 29%) from 4-[3-(1-{[(3R)-1-azabicyclo[2.2.2]oct-3-yloxy]

carbonyl}cyclohexyl)phenyl]butanoic acid (Intermediate 11, 303 mg of its TFA salt, 0.59 mmol), N-(4-formylphenyl)-5-(methylamino)pentanamide (Intermediate 114, 264 mg as its hydrochloride salt, 0.97 mmol), DIEA (530 µL, 3.03 mmol) and HATU (375 mg, 0.99 mmol) in chloroform (19.5 mL), following the experimental procedure described for the synthesis of Intermediate 96. The crude product was used without any further purification.

LRMS (m/z): 617 (M+1)+

Intermediate 116

(3R)-1-azabicyclo[2.2.2]oct-3-yl 1-(3-{4-[(5-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-5-oxopentyl)(methyl)amino]-4-oxobutyl}phenyl)cyclohexanecarboxylate Obtained as a pale yellow oil (147 mg, 78%) from (3R)-1-azabicyclo[2.2.2]oct-3-yl 1-(3-{4-[{5-[(4-formylphenyl)amino]-5-oxopentyl}(methyl)amino]-4-oxobutyl}phenyl)cyclohexanecarboxylate (Intermediate 115, 100 mg, 0.16 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 65 mg, 0.16 mmol) and sodium triacetoxyborohydride (105 mg, 0.50 mmol), following the experimental procedure described for the synthesis of Intermediate 15. No purification was used in this step.

LRMS (m/z): 935 (M+1)+; 468 (M/2+1)+

Example 17

(3R)-1-azabicyclo[2.2.2]oct-3-yl 1-(3-{4-[(5-{[4-({[(2R)-2-hydroxy-2-(8-hydroxy-2-oxo-1,2-dihydroquinolin-5-yl)ethyl]amino}methyl)phenyl]amino}-5-oxopentyl)(methyl)amino]-4-oxobutyl}phenyl)cyclohexanecarboxylate Obtained as a pale beige foam (70 mg of an 88% purity as a dihydrofluoride salt, 46%) from (3R)-1-azabicyclo[2.2.2]oct-3-yl 1-(3-{4-[(5-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-5-oxopentyl)(methyl)amino]-4-oxobutyl}phenyl)cyclohexanecarboxylate (Intermediate 116, 146 mg, 0.16 mmol) and triethylamine trihydrofluoride (77 µL, 0.47 mmol), following the experimental procedure described for the synthesis of Example 1. No purification was performed for this example.

LRMS (m/z): 818 (M+1)+; 409 (M/2+1)+

$^1$H NMR (300 MHz, DMSO-$d_6$) δ: 1.12-1.30 (m, 4H), 1.30-1.68 (m, 12H), 1.68-1.75 (m, 2H), 1.75-1.82 (m, 2H), 2.20-2.40 (m, 6H), 2.40-2.45 (m, 1H), 2.55-2.70 (m, 5H), 2.78-2.87 (two singlets, 3H), 2.90-3.10 (m, 3H), 3.30 (m, 2H), 3.74 (s, 2H), 4.67 (m, 1H), 5.08 (m, 1H), 6.46 (d, J=9.9 Hz, 1H), 6.90 (d, J=8.1 Hz, 1H), 7.05 (d, J=8.1 Hz, 1H), 7.04-7.07 (m, 1H), 7.10-7.30 (m, 5H), 7.52 (m, 2H), 8.09 (d, J=9.9 Hz, 1H), 9.86 (broad d, 1H), 10.35 (broad s, 1H).

Intermediate 117

1-azabicyclo[2.2.2]oct-4-yl methyl 1-(3-bromophenyl)cyclohexanecarboxylate

Obtained as a white solid (169 mg, 57%) from 1-(3-bromophenyl)cyclohexanecarboxylic acid (Intermediate 2, 200 mg, 0.71 mmol), thionyl chloride (2.50 mL, 34.5 mmol), azabicyclo[2.2.2]oct-4-ylmethanol (100 mg, 0.71 mmol) and butyl lithium (0.57 mL of a 1.6M solution in hexanes, 0.91 mmol), following the experimental procedure described for the synthesis of intermediate 3. Purification was performed by column chromatography over silica gel using a gradient of Chloroform/Methanol from 50/1 to 4/1.

LRMS (m/z): 406/408 (M+1)+

Intermediate 118

1-azabicyclo[2.2.2]oct-4-yl methyl 1-{3-[(1E)-4-tert-butoxy-4-oxobut-1-en-1-yl]phenyl}cyclohexanecarboxylate Obtained as a reddish oil (161 mg, 84%) from 1-azabicyclo[2.2.2]oct-4-ylmethyl 1-(3-bromophenyl)cyclohexanecarboxylate (Intermediate 117, 160 mg, 0.39 mmol), tert-butyl but-3-enoate (67 µL, 0.41 mmol), tri-ortho-tolylphosphine (120 mg, 0.39 mmol), DIEA (124 µL, 0.71 mmol) and palladium acetate (53 mg, 0.24 mmol) in acetonitrile (1.4 mL), following the experimental procedure described for the synthesis of Intermediate 6. Purification of the crude residue was performed by column chromatography over silica gel using a gradient of eluents Hexane:Chloroform:Methanol.

LRMS (m/z): 468 (M+1)+

Intermediate 119

1-azabicyclo[2.2.2]oct-4-yl methyl 1-[3-(4-tert-butoxy-4-oxobutyl)phenyl]cyclohexanecarboxylate Obtained as a brownish foam (150 mg of a 92% purity, acetate salt, 76%) from 1-azabicyclo[2.2.2]oct-4-ylmethyl 1-{3-[(1E)-4-tert-butoxy-4-oxobut-1-en-1-yl]phenyl}cyclohexanecarboxylate (Intermediate 118, 160 mg, 0.34 mmol) and palladium on carbon (43 mg of a 10% by weight, 0.034 mmol) in acetic acid (3.5 mL), following the experimental procedure described for the synthesis of Intermediate 7. The crude product was used without any further purification.

LRMS (m/z): 470 (M+1)+

Intermediate 120

4-(3-{1-[(1-azabicyclo[2.2.2]oct-4-ylmethoxy)carbonyl]cyclohexyl}phenyl)butanoic acid Obtained as a dark brown oil (163 mg of the TFA salt, 100%) from 1-azabicyclo[2.2.2]oct-4-ylmethyl 1-[3-(4-tert-butoxy-4-oxobutyl)phenyl]cyclohexane carboxylate (Intermediate 119, 145 mg, 0.27 mmol) and trifluoroacetic acid (211 µL, 2.74 mmol) in chloroform (1.5 mL), following the experimental procedure described for the synthesis of Intermediate 11. The crude product was used without any further purification.

LRMS (m/z): 414 (M+1)+

Intermediate 121

1-azabicyclo[2.2.2]oct-4-yl methyl 1-[3-(4-{[4-({[tert-butyl(dimethyl)silyl]oxy}methyl)-2-chloro-5-methoxyphenyl]amino}-4-oxobutyl)phenyl]cyclohexane carboxylate Obtained as a yellowish oil (83 mg, 44%) from 4-(3-{1-[(1-azabicyclo[2.2.2]oct-4-ylmethoxy)carbonyl]

cyclohexyl}phenyl)butanoic acid (Intermediate 120, 140 mg of the TFA salt, 0.26 mmol), 4-((tert-butyldimethylsilyloxy) methyl)-2-chloro-5-methoxyaniline (prepared according to experimental procedure described in patent WO201114180 for the synthesis of Intermediate 39, 92 mg, 0.30 mmol), DIEA (208 µL, 1.19 mmol) and HATU (131 mg, 0.34 mmol) in chloroform (2 mL), following the experimental procedure described for the synthesis of Intermediate 12. Purification was performed by column chromatography over silica gel using a gradient of Chloroform/Methanol from 50/1 to 15/1.
LRMS (m/z): 698 (M+1)+

Intermediate 122

1-azabicyclo[2.2.2]oct-4-yl methyl 1-[3-(4-{[2-chloro-4-(hydroxymethyl)-5-methoxyphenyl] amino}-4-oxobutyl)phenyl]cyclohexanecarboxylate Obtained as a yellowish oil (68 mg, 96%) from 1-azabicyclo[2.2.2]oct-4-ylmethyl 1-[3-(4-{[4-({[tert-butyl(dimethyl)silyl]oxy}methyl)-2-chloro-5-methoxyphenyl] amino}-4-oxobutyl)phenyl]cyclohexanecarboxylate (Intermediate 121, 82 mg, 0.12 mmol) and complex triethylamine trihydrofluoride (77 µL, 0.47 mmol) in THF (2 mL), following the experimental procedure described for the synthesis of Intermediate 13. The crude product was used without any further purification.
LRMS (m/z): 584 (M+1)+

Intermediate 123

1-azabicyclo[2.2.2]oct-4-ylmethyl 1-[3-{4-[(2-chloro-4-formyl-5-methoxyphenyl)amino]-4-oxobutyl}phenyl)cyclohexanecarboxylate Obtained as a pale yellow oil (59 mg of an 80% purity, 73%) from 1-azabicyclo[2.2.2]oct-4-ylmethyl 1-[3-(4-{[2-chloro-4-(hydroxymethyl)-5-methoxyphenyl] amino}-4-oxobutyl)phenyl]cyclohexanecarboxylate (Intermediate 122, 65 mg, 0.11 mmol) and Dess-Martin periodinane reagent (59 mg, 1.25 mmol) in chloroform (1.5 mL), following the experimental procedure described for the synthesis of Intermediate 14. Purification was performed by column chromatography over silica gel using a gradient of Chloroform/Methanol from 50/1 to 4/1.
LRMS (m/z): 582 (M+1)+

Intermediate 124

1-azabicyclo[2.2.2]oct-4-ylmethyl 1-[3-(4-{[4-({[(2R)-2-{[tert-butyl(dimethyl)silyl]oxy}-2-(8-hydroxy-2-oxo-1,2-dihydroquinolin-5-yl)ethyl] amino}methyl)-2-chloro-5-methoxyphenyl]amino}-4-oxobutyl)phenyl]cyclohexanecarboxylate Obtained as a pale yellow oil (19 mg, 26%) from 1-azabicyclo[2.2.2]oct-4-ylmethyl 1-(3-{4-[(2-chloro-4-formyl-5-methoxyphenyl)amino]-4-oxobutyl}phenyl)cyclohexane carboxylate (Intermediate 123, 58 mg, 0.10 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 32 mg, 0.081 mmol) and sodium triacetoxyborohydride (64 mg, 0.30 mmol), following the experimental procedure described for the synthesis of Intermediate 15. Purification was performed by column chromatography over silica gel using a gradient of Chloroform/Methanol from 50/1 to 4/1.
LRMS (m/z): 900 (M+1)+

Example 18

1-azabicyclo[2.2.2]oct-4-yl methyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl] cyclohexanecarboxylate Obtained as a white solid (10 mg as a dihydrofluoride salt, 55%) from 1-azabicyclo[2.2.2]oct-4-ylmethyl 1-[3-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl] cyclohexanecarboxylate (Intermediate 124, 19 mg, 0.021 mmol) and triethylamine trihydrofluoride (17 µL, 0.10 mmol), following the experimental procedure described for the synthesis of Example 1. No purification was performed for this example.
LRMS (m/z): 786 (M+1)+

Intermediate 125

(3R)-1-azabicyclo[2.2.2]oct-3-yl 1-(3-{(1E)-3-[(tert-butoxycarbonyl)amino]prop-1-en-1-yl}phenyl)cyclohexanecarboxylate Obtained as a brownish oil (3.1 g, 78%) from 1-(3-bromophenyl)cyclohexanecarboxylic acid (Intermediate 2, 3.0 g, 7.65 mmol), tert-butylallylcarbamate (1.26 g, 8.01 mmol) tri-ortho-tolylphosphine (2.32 g, 7.62 mmol), DIEA (2.40 mL, 13.7 mmol) and palladium acetate (1.03 g, 4.60 mmol), following the experimental procedure described for the synthesis of Intermediate 6. Purification of the crude residue was performed by column chromatography over silica gel using as a gradient a mixture of eluents Chloroform:Methanol from 0 to 20% methanol.
LRMS (m/z): 469 (M+1)+

Intermediate 126

(3R)-1-azabicyclo[2.2.2]oct-3-yl 1-(3-{3-[(tert-butoxycarbonyl)amino]propyl}phenyl)cyclohexanecarboxylate Obtained as a colorless oil (2.0 g, acetate salt, 68%) from 3R)-1-azabicyclo[2.2.2]oct-3-yl 1-(3-{(1E)-3-[(tert-butoxycarbonyl)amino]prop-1-en-1-yl}phenyl)cyclohexane carboxylate (Intermediate 125, 3.1 g, 6.62 mmol) and palladium on carbon (740 mg of a 10% by weight, 0.66 mmol) in acetic acid (8 mL), following the experimental procedure described for the synthesis of Intermediate 7. Purification of the crude residue was performed by column chromatography over silica gel using as a gradient a mixture of eluents Chloroform:Methanol from 0 to 20% methanol.
LRMS (m/z): 471 (M+1)+

Intermediate 127

(3R)-1-azabicyclo[2.2.2]oct-3-yl 1-[3-(3-aminopropyl)phenyl]cyclohexane carboxylate Obtained as an orange oil (1.19 g, 99%) from (3R)-1-azabicyclo[2.2.2]oct-3-yl 1-(3-{3-[(tert-butoxycarbonyl) amino]propyl}phenyl)cyclohexanecarboxylate (Intermediate 126, 1.76 g, 3.74 mmol) and hydrochloric acid (8.8 mL of a 4M solution in dioxane, 35.2 mmol) in chloroform (15 mL), following the experimental procedure described for the synthesis of Intermediate 24.

LRMS (m/z): 371 (M+1)+

Intermediate 128

(3R)-1-azabicyclo[2.2.2]oct-3-yl 1-[3-(3-{[(2-chloro-4-formyl-5-methoxyphenoxy)acetyl]amino}propyl)phenyl]cyclohexanecarboxylate Obtained as a yellowish oil (180 mg, 53%) from (3R)-1-azabicyclo[2.2.2]oct-3-yl 1-[3-(3-aminopropyl)phenyl]cyclohexanecarboxylate (Intermediate 127, 250 mg, 0.67 mmol), (2-chloro-4-formyl-5-methoxyphenoxy)acetic acid (Intermediate 32, 137 mg, 0.56 mmol), DIEA (400 μL, 2.3 mmol) and HATU (256 mg, 0.67 mmol) following the experimental procedure described for the synthesis of Intermediate 12. The crude residue was purified by column chromatography over silica gel using a gradient of Chloroform/Methanol.

LRMS (m/z): 596 (M+1)+

Intermediate 129

(3R)-1-azabicyclo[2.2.2]oct-3-yl 1-{3-[3-({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}amino)propyl]phenyl}cyclohexanecarboxylate Obtained as a pale yellow oil (157 mg, 57%) from (3R)-1-azabicyclo[2.2.2]oct-3-yl 1-[3-(3-{[(2-chloro-4-formyl-5-methoxyphenoxy)acetyl]amino}propyl)phenyl]cyclohexane carboxylate (Intermediate 128, 177 mg, 0.29 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 117 mg, 0.29 mmol) and sodium triacetoxyborohydride (237 mg, 1.12 mmol) in a mixture of methanol:THF (2 mL:1 mL), following the experimental procedure described for the synthesis of Intermediate 15. Purification was performed by column chromatography over silica gel using a gradient of Hexane/Ethyl Acetate/Methanol.

LRMS (m/z): 915 (M+1)+

Example 19

(3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}amino)propyl]phenyl}cyclohexanecarboxylate Obtained as a pale beige solid (99 mg as a dihydrofluoride salt, 70%) from (3R)-1-azabicyclo[2.2.2]oct-3-yl 1-{3-[3-({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}amino)propyl]phenyl}cyclohexanecarboxylate (Intermediate 129, 154 mg, 0.17 mmol) and triethylamine trihydrofluoride (148 μL, 0.91 mmol), following the experimental procedure described for the synthesis of Example 1. No purification was performed for this example.

LRMS (m/z): 801 (M+1)+

$^1$H NMR (300 MHz, DMSO-d$_6$): δ 1.10-1.30 (m, 3H), 1.30-1.50 (m, 4H), 1.50-1.75 (m, 8H), 1.75-1.82 (m, 1H), 2.20-2.45 (m, 4H), 2.55-2.75 (m, 6H), 2.95-3.10 (m, 1H), 3.10-3.20 (m, 2H), 3.63 (s, 2H), 3.72 (s, 3H), 4.61 (s, 2H), 4.62-4.70 (m, 1H), 5.0-5.05 (m, 1H), 6.46 (d, J=9.9 Hz, 1H), 6.68 (s, 1H), 6.88-6.90 (d, 1H), 7.02-7.05 (d, 1H), 7.05-7.06 (d, 1H), 7.16-7.27 (m, 3H), 7.28 (s, 1H), 7.97 (t, 1H), 8.11 (d, J=9.9 Hz, 1H), 10.37 (broad s, 1H).

Intermediate 130

(3R)-1-azabicyclo[2.2.2]oct-3-yl 1-(3-{3-[(2-chloro-4-formyl-5-methoxybenzoyl)amino]propyl}phenyl)cyclohexanecarboxylate Obtained as a viscous oil (264 mg, 83%) from (3R)-1-azabicyclo[2.2.2]oct-3-yl 1-[3-(3-aminopropyl)phenyl]cyclohexanecarboxylate (Intermediate 127, 203 mg, 0.55 mmol), 2-chloro-4-formyl-5-methoxybenzoic acid (Intermediate 89, 125 mg, 0.58 mmol), DIEA (164 μL, 0.94 mmol) and HATU (344 mg, 0.90 mmol) in DMF (6.5 mL) following the experimental procedure described for the synthesis of Intermediate 33. Purification of the crude was performed by column chromatography over silica gel using a gradient of Chloroform/Methanol.

LRMS (m/z): 567 (M+1)+

Intermediate 131

(3R)-1-azabicyclo[2.2.2]oct-3-yl 1-[3-(3-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl]amino}propyl)phenyl] cyclohexanecarboxylate Obtained as a pale yellow oil (246 mg, 58%) from (3R)-1-azabicyclo[2.2.2]oct-3-yl 1-(3-{3-[(2-chloro-4-formyl-5-methoxybenzoyl)amino]propyl}phenyl)cyclohexanecarboxylate (Intermediate 130, 261 mg, 0.46 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 181 mg, 0.46 mmol) and sodium triacetoxyborohydride (368 mg, 1.74 mmol) in a mixture of methanol:THF (3 mL:1.5 mL), following the experimental procedure described for the synthesis of Intermediate 15. Purification was performed by column chromatography over silica gel using a gradient of Hexane/Ethyl Acetate/Methanol.

LRMS (m/z): 885 (M+1)+

Example 20

(3R)-1-azabicyclo[2.2.2]oct-3-yl 1-[3-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl)phenyl]cyclohexanecarboxylate Obtained as a white solid (175 mg as a dihydrofluoride salt, 79%) from (3R)-1-azabicyclo[2.2.2]oct-3-yl 1-[3-(3-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl]amino}propyl)phenyl]cyclohexanecarboxylate (Intermediate 131, 243 mg, 0.27 mmol) and triethylamine trihydrofluoride (236 μL, 1.45 mmol), following the experimental procedure described for the synthesis of Example 1. No purification was performed for this example.

LRMS (m/z): 771 (M+1)+

$^1$H NMR (300 MHz, DMSO-d$_6$) δ: 1.15-1.32 (m, 2H), 1.32-1.52 (m, 4H), 1.52-1.70 (m, 4H), 1.70-1.83 (m, 2H), 2.25-2.40 (m, 2H), 2.40-2.46 (m, 1H), 2.55-2.75 (m, 6H), 3.0-3.10 (m, 2H), 3.22 (m, 2H), 3.70 (s, 2H), 3.78 (s, 3H), 4.67 (m, 1H), 5.05 (m, 1H), 6.49 (d, J=9.9 Hz, 1H), 6.91 (d, J=8.1 Hz, 1H), 6.96 (s, 1H), 7.06 (d, J=8.1 Hz, 1H), 7.10-7.13 (m, 1H), 7.19-7.30 (m, 3H), 7.34 (s, 1H), 8.15 (d, J=10.0 Hz, 1H), 8.42 (t, 1H), 10.4 (broad s, 1H).

Intermediate 62

Methyl 6-[(tetrahydro-2H-pyran-2-yloxy)methyl]nicotinate

To a solution of methyl 6-(hydroxymethyl)nicotinate (Intermediate 98, 505 mg, 3.02 mmol) in a mixture of dichloromethane (20 mL) and THF (10 mL) were added, under argon atmosphere, 3,4-dihydro-2H-pyran (640 μL, 7.0 mmol) and pyridinium p-toluene sulphonate (170 mg, 0.68 mmol), and the reaction mixture was heated to 50° C. for 2 h. The mixture was concentrated to dryness and the residue was purified by column chromatography over silica gel using a gradient of Hexane/Ethyl Acetate. The title compound was obtained (600 mg, 79%) as a yellow solid.

LRMS (m/z): 251 (M+1)+

Intermediate 133

6-[(tetrahydro-2H-pyran-2-yloxy)methyl]nicotinic acid

Obtained as a white solid (355 mg as the lithium carboxylate, 99%) from methyl 6-[(tetrahydro-2H-pyran-2-yloxy)methyl]nicotinate (Intermediate β2, 350 mg, 1.39 mmol) and lithium hydroxide monohydrate (60 mg, 1.43 mmol) following the experimental procedure described for the synthesis of Intermediate 89. No further purification was performed in this case.

LRMS (m/z): 236 (M−1)−

Intermediate 134

(3R)-1-azabicyclo[2.2.2]oct-3-yl 1-(3-{4-[({6-[(tetrahydro-2H-pyran-2-yloxy)methyl]pyridin-3-yl}carbonyl)amino]butyl}phenyl)cyclohexanecarboxylate Obtained as a viscous oil (626 mg, 72%) from (3R)-1-azabicyclo[2.2.2]oct-3-yl 1-[3-(4-aminobutyl)phenyl]cyclohexane carboxylate (Intermediate 65, 702 mg, 1.82 mmol), 6-[(tetrahydro-2H-pyran-2-yloxy)methyl]nicotinic acid (Intermediate 133, 270 mg of the lithium carboxylate, 1.11 mmol), DIEA (775 μL, 4.44 mmol) and HATU (675 mg, 1.77 mmol) in chloroform (14 mL), following the experimental procedure described for the synthesis of Intermediate 33. Purification of the crude was performed by column chromatography over silica gel using a gradient of Chloroform/Chloroform:Methanol:Ammonia (32%) (40:8:1).

LRMS (m/z): 605 (M+1)+

Intermediate 135

(3R)-1-azabicyclo[2.2.2]oct-3-yl 1-{3-[4-({[6-(hydroxymethyl)pyridin-3-yl]carbonyl}amino)butyl]phenyl}cyclohexanecarboxylate To a solution of (3R)-1-azabicyclo[2.2.2]oct-3-yl 1-(3-{4-[({6-[(tetrahydro-2H-pyran-2-yloxy)methyl]pyridin-3-yl}carbonyl)amino]butyl}phenyl)cyclohexanecarboxylate (Intermediate 134, 626 mg, 1.04 mmol) in THF (1.4 mL) was added hydrochloric acid (3.1 mL of a 1M solution in water, 3.1 mmol) and the mixture was stirred at room temperature overnight. Then, saturated sodium bicarbonate aqueous solution was added dropwise until neutral pH and ethyls acetate was then added. The phases were separated and the organic layer was washed with further sodium bicarbonate solution and brine. The yellow oil was further purified by column chromatography over silica gel using a gradient of Chloroform/Chloroform:Methanol:Ammonia (32%) (40:8:1) to afford the title compound as a colorless oil (412 mg, 77%)

LRMS (m/z): 521 (M+1)+

Intermediate 136

(3R)-1-azabicyclo[2.2.2]oct-3-yl 1-[3-(4-{[(6-formyl pyridin-3-yl)carbonyl]amino}butyl)phenyl]cyclohexanecarboxylate Obtained as a pale yellow oil (269 mg, 63%) from (3R)-1-azabicyclo[2.2.2]oct-3-yl 1-{3-[4-({[6-(hydroxymethyl)pyridin-3-yl]carbonyl}amino)butyl]phenyl}cyclohexane carboxylate (Intermediate 135, 406 mg, 0.78 mmol) and Dess-Martin periodinane reagent (381 mg, 0.90 mmol) in chloroform (9 mL), following the experimental procedure described for the synthesis of Intermediate 14. Purification was performed by column chromatography over silica gel using a gradient of Chloroform/Methanol.

LRMS (m/z): 519 (M+1)+

Intermediate 137

(3R)-1-azabicyclo[2.2.2]oct-3-yl 1-{3-[4-({[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]carbonyl}amino)butyl]phenyl}cyclohexanecarboxylate Obtained as a pale yellow oil (322 mg, 74%) from (3R)-1-azabicyclo[2.2.2]oct-3-yl 1-[3-(4-{[(6-formylpyridin-3-yl)carbonyl]amino}butyl)phenyl]cyclohexanecarboxylate (Intermediate 136, 263 mg, 0.51 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 200 mg, 0.50 mmol) and sodium triacetoxyborohydride (323 mg, 1.52 mmol) in a mixture of methanol:THF (4 mL:2 mL), following the experimental procedure described for the synthesis of Intermediate 15. Purification was performed by column chromatography over silica gel using a gradient of Chloroform/Chloroform:Methanol:Ammonia (32%) (40:8:1).

LRMS (m/z): 837 (M+1)+

Example 21

(3R)-1-azabicyclo[2.2.2]oct-3-yl 1-{3-[4-({[6-({[(2R)-2-hydroxy-2-(8-hydroxy-2-oxo-1,2-dihydro-quinolin-5-yl)ethyl]amino}methyl)pyridin-3-yl]carbonyl}amino)butyl]phenyl}cyclohexanecarboxylate Obtained as a white solid (218 mg as a dihydrofluoride salt, 73%) from (3R)-1-azabicyclo[2.2.2]oct-3-yl 1-{3-[4-({[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]carbonyl}amino)butyl]phenyl}cyclohexanecarboxylate (Intermediate 137, 316 mg, 0.38 mmol) and triethylamine trihydrofluoride (308 μL, 1.89 mmol), following the experimental procedure described for the synthesis of Example 1. No purification was performed for this example.

LRMS (m/z): 723 (M+1)+

$^1$H NMR (300 MHz, DMSO-$d_6$) δ: 1.15-1.30 (m,2H), 1.30-1.75 (m, 15H), 1.75-1.85 (m, 1H), 2.30-2.45 (m, 5H), 2.55-2.79 (m, 6H), 3.03-3.10 (m, 2H), 3.94 (s, 2H), 4.68 (m, 1H), 5.10-5.15 (m, 1H), 6.49 (d, J=9.9 Hz, 1H), 6.91 (d, 1H), 7.08 (d, 1H), 7.07-7.10 (m, 1H), 7.12-7.29 (m, 3H), 7.49 (d, 1H), 8.11-8.13 (m, 1H), 8.16 (d, J=9.9 Hz, 1H), 8.63 (t, 1H), 8.91 (d, J=1.7 Hz, 1H), 10.4 (broad s, 1H)

Intermediate 138

(3R)-1-azabicyclo[2.2.2]oct-3-yl 1-[3-(4-hydroxy-but-1-yn-1-yl)phenyl]cyclohexane carboxylate Obtained as a brownish oil (291 mg, 99%) from (3R)-1-azabicyclo[2.2.2]oct-3-yl 1-(3-bromophenyl)cyclohexanecarboxylate (Intermediate 3, 300 mg, 0.76 mmol), but-3-yn-1-ol (107 mg, 1.52 mmol), copper iodide (30 mg, 0.16 mmol) and tetrakis(triphenylphosphine)palladium (89 mg, 0.077 mmol) in diisopropylamine (6 mL), following the experimental procedure described for the synthesis of Intermediate 72. Purification was performed by column chromatography over silica gel using a gradient of Chloroform/Chloroform:Methanol:Ammonia (32%) (40:4:0.2).

LRMS (m/z): 382 (M+1)+

Intermediate 139

(3R)-1-azabicyclo[2.2.2]oct-3-yl 1-[3-(4-hydroxybutyl)phenyl]cyclohexane carboxylate To a solution of (3R)-1-azabicyclo[2.2.2]oct-3-yl 1-[3-(4-hydroxybut-1-yn-1-yl)phenyl]cyclohexane carboxylate (Intermediate 138, 327 mg, 0.86 mmol) in ethanol (4.5 mL) were sequentially added ammonium formate (460 mg, 7.29 mmol) and palladium hydroxide (15 mg, 0.11 mmol), and the reaction mixtures was heated overnight at 50° C. Reaction monitoring showed remaining starting material and ammonium formate (300 mg, 4.75 mmol) and palladium hydroxide (15 mg, 0.11 mmol) were added again to the reaction mixture and stirring was maintained for further 24 hours. The mixture was filtered through a pad of Celite® and the solvent was evaporated to dryness. The residue obtained was dissolved in chloroform (30 mL) and the organic phase was washed with saturated solution of potassium carbonate (30 mL). The aqueous phase was extracted with chloroform (3×30 mL) and the combined organic extracts were washed with water and brine, dried, filtered and concentrated to dryness. The crude obtained was purified by column chromatography over silica gel using a gradient of Hexane/Chloroform/Methanol to afford the title compound as a yellow oil (62 mg, 18%).

LRMS (m/z): 386 (M+1)+

Intermediate 140

4-[3-(1-{[(3R)-1-azabicyclo[2.2.2]oct-3-yloxy]carbonyl}cyclohexyl)phenyl]butyl 2-chloro-4-formyl-5-methoxybenzoate Obtained as an orange oil (114 mg of a 73% purity, 89%) from (3R)-1-azabicyclo[2.2.2]oct-3-yl 1-[3-(4-hydroxybutyl)phenyl]cyclohexane carboxylate (Intermediate 139, 62 mg, 0.16 mmol), 2-chloro-4-formyl-5-methoxybenzoic acid (Intermediate 89, 40 mg, 0.19 mmol), DIEA (45 μL, 0.26 mmol) and HATU (90 mg, 0.24 mmol) in chloroform (2 mL), following the experimental procedure described for the synthesis of Intermediate 96. The crude obtained was used without any further purification.

LRMS (m/z): 583 (M+1)+

Intermediate 141

4-[3-(1-{[(3R)-1-azabicyclo[2.2.2]oct-3-yloxy]carbonyl}cyclohexyl)phenyl]butyl 4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoate Obtained as a pale yellow foam (97 mg of an 80% purity, 60%) from (4-[3-(1-{[(3R)-1-azabicyclo[2.2.2]oct-3-yloxy]carbonyl}cyclohexyl)phenyl]butyl 2-chloro-4-formyl-5-methoxybenzoate (Intermediate 140, 114 mg of a 73% purity, 0.14 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 61 mg, 0.15 mmol) and sodium triacetoxyborohydride (135 mg, 0.64 mmol) in a mixture of methanol:THF (0.5 mL:1 mL), following the experimental procedure described for the synthesis of Intermediate 15. Purification was performed by column chromatography over silica gel using a gradient of Ethyl Acetate/Methanol.

LRMS (m/z): 901 (M+1)+; 451 (M/2+1)+

Example 22

4-[3-(1-{[(3R)-1-azabicyclo[2.2.2]oct-3-yloxy]carbonyl}cyclohexyl)phenyl]butyl 2-chloro-4-({[(2R)-2-hydroxy-2-(8-hydroxy-2-oxo-1,2-dihydro-quinolin-5-yl)ethyl]amino}methyl)-5-methoxybenzoate Obtained as a beige precipitate (44 mg as a dihydrofluoride salt, 65%) from 4-[3-(1-{[(3R)-1-azabicyclo[2.2.2]oct-3-yloxy]carbonyl}cyclohexyl)phenyl]butyl 4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoate (Intermediate 141, 84 mg, 0.093 mmol) and triethylamine trihydrofluoride (37 μL, 0.23 mmol), following the experimental procedure described for the synthesis of Example 1. No purification was performed for this example.

LRMS (m/z): 787 (M+1)+; 394 (M/2+1)+

¹H NMR (300 MHz, DMSO-d₆) δ: 1.17-1.32 (m, 2H), 1.32-1.48 (m, 5H), 1.48-1.78 (m, 10H), 1.81 (m, 1H), 2.27-2.47 (m, 4H), 2.55-2.78 (m, 5H), 2.85-3.0 (m, 2H), 3.75 (s, 2H), 3.79 (s, 3H), 4.29 (s, 2H), 4.70 (m, 1H), 5.07 (m, 1H), 6.48 (d, J=9.8 Hz, 1H), 6.91 (d, J=8.0 Hz, 1H), 7.06 (d, J=8.7 Hz, 1H), 7.08-7.15 (m, 1H), 7.17-7.25 (m, 2H), 7.25-7.30 (m, 2H), 7.45 (s, 1H), 8.14 (d, J=10.0 Hz, 1H), 10.4 (broad s, 1H).

Intermediate 142

Methyl 2-but-3-en-1-yl-1-oxoisoindoline-5-carboxylate

Obtained as a yellow foam (366 mg of a 68% purity, 83%) from methyl 1-oxoisoindoline-5-carboxylate (200 mg, 1.05 mmol), 4-bromobut-1-ene (1.5 mL, 14.8 mmol) and sodium hydride (194 mg of a 60% dispersion in oil, 8.08 mmol) following the experimental procedure described for the synthesis of Intermediate 47. No purification was performed on the crude obtained.
LRMS (m/z): 246 (M+1)+

Intermediate 143

2-but-3-en-1-yl-5-(hydroxymethyl)isoindolin-1-one

Obtained as a yellow foam (62 mg, 34%) from methyl 2-but-3-en-1-yl-1-oxoisoindoline-5-carboxylate (Intermediate 142, 366 mg, 1.49 mmol) and lithium borohydride (2.0 mL of a 2 M solution in THF) in THF (10 mL), following the experimental procedure described for the synthesis of Intermediate 56. The crude obtained was purified by column chromatography over silica gel using a gradient of Chloroform/Methanol.
LRMS (m/z): 218 (M+1)+

Intermediate 144

2-but-3-en-1-yl-1-oxoisoindoline-5-carbaldehyde

Obtained as a yellow solid (52 mg, 61%) from 2-but-3-en-1-yl-5-(hydroxymethyl)isoindolin-1-one (Intermediate 143, 86 mg, 0.40 mmol) and manganese dioxide (348 mg, 4.0 mmol) in chloroform (9 mL), following the experimental procedure described for the synthesis of Intermediate 31. The crude obtained was purified by column chromatography over silica gel using a gradient of Hexane/Diethyl ether.

Intermediate 145

(3R)-1-azabicyclo[2.2.2]oct-3-yl 1-{3-[(1E)-4-(5-formyl-1-oxo-1,3-dihydro-2H-isoindol-2-yl)but-1-en-1-yl]phenyl}cyclohexanecarboxylate Obtained as a colorless oil (39 mg, 50%) from (3R)-1-azabicyclo[2.2.2]oct-3-yl 1-(3-bromophenyl)cyclohexanecarboxylate (Intermediate 3, 60 mg, 0.15 mmol), 2-but-3-en-1-yl-1-oxoisoindoline-5-carbaldehyde (Intermediate 144, 32 mg, 0.15 mmol), tri-ortho-tolylphosphine (14 mg, 0.046 mmol), DIEA (35 μL, 0.20 mmol) and palladium acetate (6 mg, 0.027 mmol) in a mixture of acetonitrile (1 mL) and THF (1 mL), following the experimental procedure described for the synthesis of Intermediate 6. The crude residue obtained was purified by column chromatography over silica gel using a gradient of Hexane/Chloroform/Methanol.
LRMS (m/z): 528 (M+1)+

Intermediate 146

(3R)-1-azabicyclo[2.2.2]oct-3-yl 1-(3-{(1E)-4-[5-({[(2R)-2-{[tert-butyl(dimethyl)silyl]oxy}-2-(8-hydroxy-2-oxo-1,2-dihydroquinolin-5-yl)ethyl]amino}methyl)-1-oxo-1,3-dihydro-2H-isoindol-2-yl]but-1-en-1-yl}phenyl)cyclohexanecarboxylate Obtained as a pale yellow foam (51 mg of a 71% purity, 58%) from (3R)-1-azabicyclo[2.2.2]oct-3-yl 1-{3-[(1E)-4-(5-formyl-1-oxo-1,3-dihydro-2H-isoindol-2-yl)but-1-en-1-yl]phenyl}cyclohexanecarboxylate (Intermediate 145, 39 mg, 0.074 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 32 mg, 0.081 mmol) and sodium triacetoxyborohydride (109 mg, 0.51 mmol) in a mixture of methanol:THF (0.5 mL:1 mL), following the experimental procedure described for the synthesis of Intermediate 15. No further purification was performed in this step.
LRMS (m/z): 846 (M+1)+; 424 (M/2+1)+

Intermediate 147

(3R)-1-azabicyclo[2.2.2]oct-3-yl 1-(3-{4-[5-({[(2R)-2-{[tert-butyl(dimethyl)silyl]oxy}-2-(8-hydroxy-2-oxo-1,2-dihydroquinolin-5-yl)ethyl]amino}methyl)-1-oxo-1,3-dihydro-2H-isoindol-2-yl]butyl}phenyl)cyclohexanecarboxylate Obtained as a yellow foam (23 mg, 60%) from (3R)-1-azabicyclo[2.2.2]oct-3-yl 1-(3-{(1E)-4-[5-({[(2R)-2-{[tert-butyl(dimethyl)silyl]oxy}-2-(8-hydroxy-2-oxo-1,2-dihydroquinolin-5-yl)ethyl]amino}methyl)-1-oxo-1,3-dihydro-2H-isoindol-2-yl]but-1-en-1-yl}phenyl)cyclohexanecarboxylate (Intermediate 146, 51 mg, 0.04 mmol) and palladium on carbon (10 mg of a 10% by weight, 0.011 mmol) in acetic acid (0.5 mL) and THF (0.75 mL), following the experimental procedure described for the synthesis of Intermediate 7. The crude product was purified initially by column chromatography over silica gel using a gradient of Chloroform:Methanol as eluent, and additionally by reverse phase column chromatography over C18 modified silica gel eluting with a gradient of water/methanol.
LRMS (m/z): 848 (M+1)+; 425 (M/2+1)+

Example 23

(3R)-1-azabicyclo[2.2.2]oct-3-yl 1-(3-{4-[5-({[(2R)-2-hydroxy-2-(8-hydroxy-2-oxo-1,2-dihydroquinolin-5-yl)ethyl]amino}methyl)-1-oxo-1,3-dihydro-2H-isoindol-2-yl]butyl}phenyl)cyclohexanecarboxylate Obtained as a beige precipitate (15 mg as a dihydrofluoride salt, 67%) from (3R)-1-azabicyclo[2.2.2]oct-3-yl 1-(3-{4-[5-({[(2R)-2-{[tert-butyl(dimethyl)silyl]oxy}-2-(8-hydroxy-2-oxo-1,2-dihydroquinolin-5-yl)ethyl]amino}methyl)-1-oxo-1,3-dihydro-2H-isoindol-2-yl]butyl}phenyl)cyclohexanecarboxylate (Intermediate 147, 23 mg, 0.03 mmol) and triethylamine trihydrofluoride (15 μL, 0.09 mmol), following the experimental procedure described for the synthesis of Example 1. No purification was performed for this example.
LRMS (m/z): 734 (M+1)+; 367 (M/2+1)+

¹H NMR (300 MHz, DMSO-d$_6$) δ: 1.0-1.80 (m, 17H), 1.86 (m, 1H), 2.20-2.90 (m, 11H), 3.99 (s, 2H), 4.38 (s, 2H), 4.77 (m,1H), 5.19 (m, 1H), 6.48 (d, J=9.9 Hz, 1H), 6.93 (d, J=8.1 Hz, 1H), 7.03-7.15 (m, 1H), 7.08 (d, J=8.2 Hz, 1H), 7.15-7.31 (m, 3H), 7.45-7.55 (m, 1H), 7.55-7.68 (m, 2H), 8.16 (d, J=9.9 Hz, 1H), 10.35 (broad s, 1H).

Intermediate 148

(3R)-1-azabicyclo[2.2.2]oct-3-yl 1-[3-(4-{[(2-chloro-4-formyl-5-methoxyphenoxy)acetyl]amino}butyl)phenyl]cyclohexanecarboxylate Obtained as a yellowish oil (159 mg, 43%) from (3R)-1-azabicyclo[2.2.2]oct-3-yl 1-[3-(4-aminobutyl)phenyl]cyclohexanecarboxylate (Intermediate 65, 308 mg, 0.80 mmol), (2-chloro-4-formyl-5-methoxyphenoxy)acetic acid (Intermediate 32, 130 mg, 0.53 mmol), DIEA (380 μL, 2.18 mmol) and HATU (243 mg, 0.64 mmol) following the experimental procedure described for the synthesis of Intermediate 12. The crude residue was purified by column chromatography over silica gel using a gradient of Chloroform/Methanol.
LRMS (m/z): 611 (M+1)+

Intermediate 149

(3R)-1-azabicyclo[2.2.2]oct-3-yl 1-{3-[4-({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}amino)butyl]phenyl}cyclohexanecarboxylate Obtained as a viscous oil (112 mg, 53%) from (3R)-1-azabicyclo[2.2.2]oct-3-yl 1-[3-(4-{[(2-chloro-4-formyl-5-methoxyphenoxy)acetyl]amino}butyl)phenyl]cyclohexane carboxylate (Intermediate 148, 155 mg, 0.25 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 85 mg, 0.25 mmol) and sodium triacetoxyborohydride (203 mg, 0.96 mmol) in a mixture of methanol:THF (2 mL:1 mL), following the experimental procedure described for the synthesis of Intermediate 15. Purification was performed by column chromatography over silica gel using a gradient of Hexane/Ethyl Acetate/Methanol.
LRMS (m/z): 929 (M+1)+

Example 24

(3R)-1-azabicyclo[2.2.2]oct-3-yl 1-{3-[4-({[2-chloro-4-({[2-hydroxy-2-(8-hydroxy-2-oxo-1,2-dihydroquinolin-5-yl)ethyl]amino}methyl)-5-methoxyphenoxy]acetyl}amino)butyl]phenyl}cyclohexanecarboxylate Obtained as a beige precipitate (68 mg as a dihydrofluoride salt, 67%) from (3R)-1-azabicyclo[2.2.2]oct-3-yl 1-{3-[4-({[4-({[(2R)-2-{[tert-butyl(dimethyl)silyl]oxy}-2-(8-hydroxy-2-oxo-1,2-dihydroquinolin-5-yl(ethyl]amino}methyl)-2-chloro-5-methoxyphenoxy]acetyl}amino)butyl]phenyl}cyclohexanecarboxylate (Intermediate 149, 110 mg, 0.12 mmol) and triethylamine trihydrofluoride (105 μL, 0.64 mmol), following the experimental procedure described for the synthesis of Example 1. No purification was performed for this example.
LRMS (m/z): 815 (M+1)+

¹H NMR (300 MHz, DMSO-d$_6$) δ: 1.15-1.30 (m, 5H), 1.30-1.75 (m, 12H), 1.75-1.85 (m, 1H), 2.25-2.80 (m, 9H), 3.05-3.10 (m, 2H), 3.15-3.20 (m, 2H), 3.65 (s, 2H), 3.73 (s, 3H), 4.59 (s, 2H), 4.67 (m, 1H), 5.06 (m, 1H), 6.48 (d, J=9.9 Hz, 1H), 6.68 (s, 1H), 6.91 (d, J=8.1 Hz, 1H), 7.05 (d, J=8.1 Hz, 1H), 7.12-7.26 (m, 4H), 7.30 (s, 1H), 7.90 (t, 1H), 8.12 (d, J=10.0 Hz, 1H), 10.30 (broad s, 1H).

Intermediate 150

(3R)-1-azabicyclo[2.2.2]oct-3-yl 1-(3-{3-[({6-[(tetrahydro-2H-pyran-2-yloxy)methyl]pyridin-3-yl}carbonyl)amino]propyl}phenyl)cyclohexanecarboxylate Obtained as a viscous oil (789 mg, 96%) from (3R)-1-azabicyclo[2.2.2]oct-3-yl 1-[3-(3-aminopropyl)phenyl]cyclohexanecarboxylate (Intermediate 127, 720 mg, 1.94 mmol), 6-[(tetrahydro-2H-pyran-2-yloxy)methyl]nicotinic acid (Intermediate 133, 355 mg of the lithium carboxylate, 1.46 mmol), DIEA (960 μL, 5.50 mmol) and HATU (835 mg, 2.20 mmol) in chloroform (17 mL), following the experimental procedure described for the synthesis of Intermediate 33. Purification of the crude was performed by column chromatography over silica gel using a gradient of Hexane/Chloroform/Methanol.
LRMS (m/z): 591 (M+1)+

Intermediate 151

(3R)-1-azabicyclo[2.2.2]oct-3-yl 1-{3-[3-({[6-(hydroxymethyl)pyridin-3-yl]carbonyl}amino)propyl]phenyl}cyclohexanecarboxylate Obtained as a viscous oil (471 mg, 70%) from (3R)-1-azabicyclo[2.2.2]oct-3-yl 1-(3-{3-[({6-[(tetrahydro-2H-pyran-2-yloxy)methyl]pyridin-3-yl}carbonyl)amino]propyl}phenyl)cyclohexanecarboxylate (Intermediate 150, 782 mg, 1.33 mmol) and hydrochloric acid (4.0 mL of a 1M solution in water, 4.0 mmol) in THF (1.8 mL), following the experimental procedure described for the synthesis of Intermediate 135. Purification of the crude was performed by column chromatography over silica gel using a gradient of Chloroform/Methanol.
LRMS (m/z): 507 (M+1)+

Intermediate 152

(3R)-1-azabicyclo[2.2.2]oct-3-yl 1-[3-(3-{[(6-formyl pyridin-3-yl)carbonyl]amino}propyl)phenyl]cyclohexanecarboxylate Obtained as a pale yellow oil (216 mg, 45%) from (3R)-1-azabicyclo[2.2.2]oct-3-yl 1-{3-[3-({[6-(hydroxymethyl)pyridin-3-yl]carbonyl}amino)propyl]phenyl}cyclohexane carboxylate (Intermediate 151, 467 mg, 0.92 mmol) and Dess-Martin periodinane reagent (450 mg, 1.06 mmol) in chloroform (10 mL), following the experimental procedure described for the synthesis of Intermediate 14. Purification was performed by column chromatography over silica gel using a gradient of Chloroform/Methanol.
LRMS (m/z): 505 (M+1)+

Intermediate 153

(3R)-1-azabicyclo[2.2.2]oct-3-yl 1-{3-[3-({[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]carbonyl}amino)propyl]phenyl}cyclohexanecarboxylate

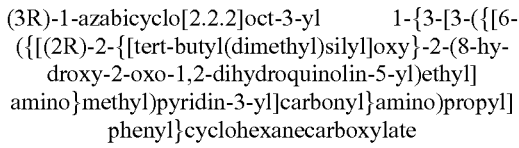

Obtained as a viscous oil (322 mg, 90%) from (3R)-1-azabicyclo[2.2.2]oct-3-yl 1-[3-(3-{[(6-formylpyridin-3-yl)carbonyl]amino}propyl)phenyl]cyclohexanecarboxylate (Intermediate 152, 212 mg, 0.42 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 140 mg, 0.42 mmol) and sodium triacetoxyborohydride (268 mg, 1.26 mmol) in a mixture of methanol:THF (3.2 mL:1.6 mL), following the experimental procedure described for the synthesis of Intermediate 15. Purification was performed by column chromatography over silica gel using a gradient of Chloroform/Methanol.

LRMS (m/z): 823 (M+1)+

Example 25

(3R)-1-azabicyclo[2.2.2]oct-3-yl 1-{3-[3-({[6-({[(2R)-2-hydroxy-2-(8-hydroxy-2-oxo-1,2-dihydroquinolin-5-yl)ethyl]amino}methyl)pyridin-3-yl]carbonyl}amino)propyl]phenyl}cyclohexanecarboxylate Obtained as a beige solid (187 mg as a dihydrofluoride salt, 62%) from (3R)-1-azabicyclo[2.2.2]oct-3-yl 1-{3-[3-({[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]carbonyl}amino)propyl]phenyl}cyclohexanecarboxylate (Intermediate 153, 318 mg, 0.39 mmol) and triethylamine trihydrofluoride (315 μL, 1.93 mmol), following the experimental procedure described for the synthesis of Example 1. No purification was performed for this example.

LRMS (m/z): 709 (M+1)+

$^1$H NMR (300 MHz, DMSO-$d_6$) δ: 1.16-1.32 (m, 4H), 1.32-1.50 (m, 4H), 1.50-1.74 (m, 5H), 1.74-1.90 (m, 3H), 2.25-2.45 (m, 4H), 2.60-2.82 (m, 7H), 3.0-3.15 (m, 2H), 3.93 (s, 2H), 4.68 (m, 1H), 5.11 (m, 1H), 6.49 (d, J=9.9 Hz, 1H), 6.91 (d, J=8.1 Hz, 1H), 7.07 (d, J=8.2 Hz, 1H), 7.11-7.13 (m, 1H), 7.18-7.29 (m, 3H), 7.49 (d, 1H), 8.11 (m, 1H), 8.16 (d, J=10.1 Hz, 1H), 8.61 (t, 1H), 8.90 (d, 1H), 10.30 (broad s, 1H).

Intermediate 154 tert-butyl but-3-en-1-yl(methyl)carbamate

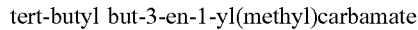

To a 0° C. solution of tert-butyl but-3-en-1-ylcarbamate (Intermediate 62, 840 mg, 4.9 mmol) in THF (20 mL) was added, under inert atmosphere, sodium hydride (216 mg of a 60% dispersion in oil, 8.99 mmol) and the reaction mixture was stirred at r.t. for 1 h before methyl iodide (3.05 mL, 49.0 mmol) was added. The reaction mixture was heated to reflux and maintained at this temperature overnight. Ice was then added and the aqueous phase was extracted with ethyl acetate (3×50 mL). The combined organic extracts were washed with brine, filtered and concentrated to dryness to afford the title compound as a colorless oil (893 mg, 98%).

1H NMR (300 MHz, cdcl3) δ 5.75 (dddd, J=17.1, 13.7, 6.8, 3.4 Hz, 1H), 5.17-4.92 (m, 2H), 3.39-3.08 (m, 2H), 2.84 (s, 3H), 2.37-2.13 (m, 2H), 1.45 (s, 9H).

Intermediate 155

(3R)-1-azabicyclo[2.2.2]oct-3-yl 1-(3-{(1E)-4-[(tert-butoxycarbonyl)(methyl)amino]but-1-en-1-yl}phenyl)cyclohexanecarboxylate

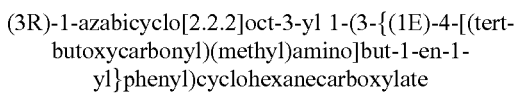

Obtained as a yellow foam (220 mg, 21%) from (3R)-1-azabicyclo[2.2.2]oct-3-yl 1-(3-bromophenyl)cyclohexanecarboxylate (Intermediate 3, 890 g, 2.27 mmol), tert-butyl but-3-en-1-yl(methyl)carbamate (Intermediate 154, 400 mg, 2.16 mmol), tri-ortho-tolylphosphine (657 mg, 2.16 mmol), DIEA (0.68 mL, 3.89 mmol) and palladium acetate (291 mg, 1.29 mmol), following the experimental procedure described for the synthesis of Intermediate 6. Purification of the crude residue was performed by column chromatography over silica gel using as a gradient a mixture of eluents Chloroform:Methanol.

LRMS (m/z): 497 (M+1)+

Intermediate 156

3R)-1-azabicyclo[2.2.2]oct-3-yl 1-(3-{4-[(tert-butoxycarbonyl)(methyl)amino]butyl}phenyl)cyclohexanecarboxylate

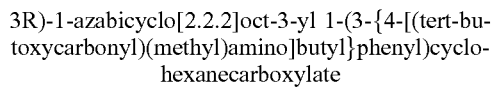

Obtained as a colorless oil (382 mg of a 92% purity, 100%) from (3R)-1-azabicyclo[2.2.2]oct-3-yl 1-(3-{(1E)-4-[(tert-butoxycarbonyl)(methyl)amino]but-1-en-1-yl}phenyl)cyclohexanecarboxylate (Intermediate 155, 348 mg, 0.70 mmol) and palladium on carbon (75 mg of a 10% by weight, 0.07 mmol) in a mixture of THF (2.2 mL) and acetic acid (2.2 mL), following the experimental procedure described for the synthesis of Intermediate 7. The crude product was used without any further purification.

LRMS (m/z): 499 (M+1)+

Intermediate 157

(3R)-1-azabicyclo[2.2.2]oct-3-yl 1-{3-[4-(methylamino)butyl]phenyl}cyclohexanecarboxylate

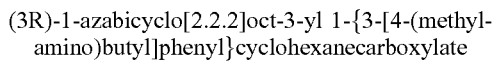

Obtained as a yellow oil (306 mg of a 93% purity, 100%) from 3R)-1-azabicyclo[2.2.2]oct-3-yl 1-(3-{4-[(tert-butoxycarbonyl)(methyl)amino]butyl}phenyl) cyclohexanecarboxylate (Intermediate 156, 379 mg, 0.76 mmol) and hydrochloric acid (1.29 mL of a 4M solution in Dioxane, 7.4 mmol) in chloroform (6.5 mL), following the experimental procedure described for the synthesis of Intermediate 24. The crude product was used without any further purification.

LRMS (m/z): 400 (M+1)+

Intermediate 158

(3R)-1-azabicyclo[2.2.2]oct-3-yl 1-(3-{4-[[(2-chloro-4-formyl-5-methoxyphenoxy)acetyl](methyl)amino]butyl}phenyl)cyclohexanecarboxylate

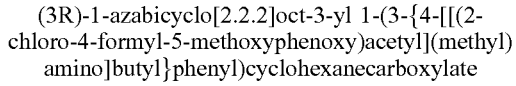

Obtained as a viscous oil (337 mg, 100%) from ((3R)-1-azabicyclo[2.2.2]oct-3-yl 1-{3-[4-(methylamino)butyl]phenyl}cyclohexanecarboxylate (Intermediate 157, 306 mg, 0.77 mmol), (2-chloro-4-formyl-5-methoxyphenoxy)acetic acid (Intermediate 32, 116 mg, 0.47 mmol), DIEA (500 μL, 2.85 mmol) and HATU (317 mg, 0.83 mmol) following the

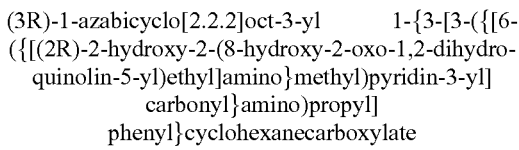

experimental procedure described for the synthesis of Intermediate 12. The crude residue was purified by column chromatography over silica gel using a gradient of Chloroform/Methanol.

LRMS (m/z): 626 (M+1)+

Intermediate 159

(3R)-1-azabicyclo[2.2.2]oct-3-yl 1-(3-{4-[{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}(methyl)amino]butyl}phenyl)cyclohexanecarboxylate Obtained as a viscous colorless foam (368 mg, 72%) from (3R)-1-azabicyclo[2.2.2]oct-3-yl 1-(3-{4-[[(2-chloro-4-formyl-5-methoxyphenoxy)acetyl](methyl)amino]butyl}phenyl)cyclohexanecarboxylate (Intermediate 158, 334 mg, 0.53 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 240 mg, 0.61 mmol) and sodium triacetoxyborohydride (486 mg, 2.29 mmol) following the experimental procedure described for the synthesis of Intermediate 15. The crude residue was purified by column chromatography over silica gel using a gradient of Hexane/Acetone/Methanol.

LRMS (m/z): 944 (M+1)+

Example 26

(3R)-1-azabicyclo[2.2.2]oct-3-yl 1-(3-{4-[{[2-chloro-4-({[2-hydroxy-2-(8-hydroxy-2-oxo-1,2-dihydroquinolin-5-yl)ethyl]amino}methyl)-5-methoxyphenoxy]acetyl}(methyl)amino]butyl}phenyl)cyclohexanecarboxylate Obtained as a beige solid (200 mg as a dihydrofluoride salt, 55%) from (3R)-1-azabicyclo[2.2.2]oct-3-yl 1-(3-{4-[{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}(methyl)amino]butyl}phenyl)cyclohexanecarboxylate (Intermediate 159, 363 mg, 0.38 mmol) and triethylamine trihydrofluoride (338 μL, 2.08 mmol), following the experimental procedure described for the synthesis of Example 1. No additional purification was necessary for this example.

LRMS (m/z): 830 (M+1)+

$^1$H NMR (300 MHz, DMSO-d$_6$) δ: 1.10-1.30 (m, 5H), 1.30-1.47 (m, 6H), 1.47-1.73 (m, 6H), 1.78 (m, 1H), 2.25-2.45 (m, 5H), 2.55-2.80 (m, 6H), 2.92-3.10 (m, 2H), 2.97 (s, 3H), 3.62 (s, 2H), 3.64 (s, 3H), 4.64 (m, 1H), 4.92 (m, 2H), 5.04 (m, 1H), 6.47 (d, J=9.9 Hz, 1H), 6.59 (m, 1H), 6.90 (d, J=8.1 Hz, 1H), 7.04 (d, J=8.2 Hz, 1H), 7.0-7.10 (m, 1H), 7.12-7.30 (m, 4H), 8.11 (d, J=10.0 Hz, 1H), 10.4 (broad s, 1H).

Intermediate 160

(3R)-1-azabicyclo[2.2.2]oct-3-yl 1-(3-{4-[(5-formyl-1,3-thiazol-2-yl)amino]-4-oxobutyl}phenyl)cyclohexanecarboxylate To a stirred solution of 4-[3-(1-{[(3R)-1-azabicyclo[2.2.2]oct-3-yloxy]carbonyl}cyclohexyl)phenyl]butanoic acid (Intermediate 11, 250 mg, 0.62 mmol) in DMF (4 mL) were sequentially added 2-aminothiazole-5-carbaldehyde (120 mg, 0.94 mmol) 1-ethyl-3-(3-dimethylaminopropyl)carbodiimide hydrochloride (179 mg, 0.94 mmol), 4-dimethylaminopyridine (38 mg, 0.31 mmol) and triethylamine (218 μL, 1.56 mmol), and stirring was maintained at r.t. overnight The solvent was removed by rotary evaporation and the residue was dissolved in chloroform (20 mL). The organic phase was washed with 4% aqueous solution of sodium bicarbonate and brine, dried over anhydrous sodium sulphate, filtered and concentrated to dryness. The crude obtained was purified by column chromatography over silica gel to afford the title compound as a yellowish foam (140 mg, 44%).

LRMS (m/z): 510 (M+1)+

Intermediate 161

(3R)-1-azabicyclo[2.2.2]oct-3-yl 1-[3-(4-{[5-({[(2R)-2-{[tert-butyl(dimethyl)silyl]oxy}-2-(8-hydroxy-2-oxo-1,2-dihydroquinolin-5-yl)ethyl]amino}methyl)-1,3-thiazol-2-yl]amino}-4-oxobutyl)phenyl]cyclohexanecarboxylate Obtained as a viscous colorless foam (15 mg, 7%) from (3R)-1-azabicyclo[2.2.2]oct-3-yl 1-(3-{4-[(5-formyl-1,3-thiazol-2-yl)amino]-4-oxobutyl}phenyl)cyclohexanecarboxylate (Intermediate 160, 140 mg, 0.27 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 108 mg, 0.27 mmol) and sodium triacetoxyborohydride (174 mg, 0.82 mmol) following the experimental procedure described for the synthesis of Intermediate 15. The crude residue was purified by column chromatography over silica gel using a gradient of Hexane/Ethyl Acetate/Methanol and purified again by reverse phase column chromatography over C18 modified silica gel using a gradient of Water/Methanol.

LRMS (m/z): 828 (M+1)+

Example 27

(3R)-1-azabicyclo[2.2.2]oct-3-yl 1-[3-(4-{[5-({[(2R)-2-hydroxy-2-(8-hydroxy-2-oxo-1,2-dihydroquinolin-5-yl)ethyl]amino}methyl)-1,3-thiazol-2-yl]amino}-4-oxobutyl)phenyl]cyclohexanecarboxylate Obtained as a beige solid (12.5 mg as a dihydrofluoride salt, 92%) from (3R)-1-azabicyclo[2.2.2]oct-3-yl 1-[3-(4-{[5-({[(2R)-2-{[tert-butyl(dimethyl)silyl]oxy}-2-(8-hydroxy-2-oxo-1,2-dihydroquinolin-5-yl(ethyl]amino}methyl)-1,3-thiazol-2-yl]amino}-4-oxobutyl)phenyl]cyclohexanecarboxylate (Intermediate 161, 15 mg, 0.018 mmol) and triethylamine trihydrofluoride (17 μL, 0.10 mmol), following the experimental procedure described for the synthesis of Example 1. No additional purification was necessary for this example.

LRMS (m/z): 714 (M+1)+

$^1$H NMR (300 MHz, DMSO-d$_6$) δ: 1.25-1.35 (m, 3H), 1.35-1.55 (m, 5H), 1.55-1.75 (m, 5H), 1.80-1.95 (m, 3H), 2.27-2.45 (m, 4H), 2.50-2.75 (m, 4H), 2.80-2.95 (m, 3H), 3.0-3.15 (m, 2H), 3.90 (s, 2H), 4.71 (m, 1H), 5.05 (m, 1H), 6.46 (d, J=9.8 Hz, 1H), 6.90 (d, J=8.1 Hz, 1H), 7.06 (d, J=8.2 Hz, 1H), 7.08-7.11 (m, 1H), 7.17-7.23 (m, 2H), 7.24 (s, 1H), 7.27-7.30 (m, 1H), 8.12 (d, J=10.0 Hz, 1H), 10.3 (broad s, 1H), 12.0 (broad s, 1H).

Intermediate 162 tert-butyl 4-[({[1-(3-bromophenyl)cyclohexyl]carbonyl}oxy)methyl]piperidine-1-carboxylate Obtained as a yellow oil (546 mg, 74%) from 1-(3-bromophenyl)cyclohexanecarboxylic acid (Intermediate 2, 400 mg, 1.41 mmol), thionyl chloride (5.0 mL, 68.9 mmol), tert-butyl 4-(hydroxymethyl)piperidine-1-carboxylate (304 mg, 1.41 mmol) and butyl lithium (1.14 mL of a 1.6M solution in hexanes, 1.85 mmol) in toluene (6 mL) and THF (6 mL), following the experimental procedure described for the synthesis of Intermediate 3. Purification of the crude obtained was performed by column chromatography over silica gel using a gradient of Hexane/Chloroform/Methanol.

LRMS (m/z): 480 (M)+; 482 (M+2)+

Intermediate 163 benzyl but-3-enoate

To a solution of but-3-enoic acid (500 mg, 5.81 mmol) in dichloromethane (3 mL) was added pyridine (1.13 mL, 13.8 mmol). Then, a solution of benzyl chloroformate (912 µL, 6.39 mmol) in dichloromethane (5 mL) was added dropwise and stirring was maintained a r.t. for 16 hours. The reaction mixture was filtered through a pad of Celite® and the filtrate was washed with saturated aqueous copper sulphate solution (3×20 mL). The resulting organic layer was dried, filtered and concentrated to dryness, and the residue was purified by column chromatography over silica gel using a gradient of Hexane/Diethyl Ether to yield the title compound (656 mg, 64%) as a colorless oil.

1H NMR (300 MHz, cdcl3) δ 7.46-7.28 (m, 5H), 6.09-5.81 (m, 1H), 5.22-5.19 (m, 1H), 5.18-5.14 (m, 1H), 5.14 (s, 2H), 3.15 (dt, J=7.0, 1.4 Hz, 2H).

Intermediate 164 tert-butyl 4-({[(1-{3-[(1E)-4-(benzyloxy)-4-oxobut-1-en-1-yl]phenyl}cyclohexyl)carbonyl]oxy}methyl)piperidine-1-carboxylate Obtained as a yellow oil (300 mg, 50%) from tert-butyl 4-[({[1-(3-bromophenyl)cyclohexyl]carbonyl}oxy)methyl] piperidine-1-carboxylate (Intermediate 162, 400 mg, 0.88 mmol), benzyl but-3-enoate (Intermediate 163, 163 mg, 0.92 mmol), tri-ortho-tolylphosphine (268 mg, 0.88 mmol), DIEA (277 µL, 1.59 mmol) and palladium acetate (118 mg, 0.53 mmol), following the experimental procedure described for the synthesis of Intermediate 6. Purification of the crude residue was performed by column chromatography over silica gel using as a gradient a mixture of eluents Hexane/Diethyl Ether.

LRMS (m/z): 576 (M+1)+

Intermediate 165

4-{3-[1-({[1-(tert-butoxycarbonyl)piperidin-4-yl]methoxy}carbonyl)cyclohexyl]phenyl}butanoic acid Obtained as a colorless oil (245 mg of an 85% purity, 82%) from tert-butyl 4-({[(1-{3-[(1E)-4-(benzyloxy)-4-oxobut-1-en-1-yl]phenyl}cyclohexyl)carbonyl]oxy}methyl)piperidine-1-carboxylate (Intermediate 164, 300 mg, 0.52 mmol) and palladium on carbon (131 mg of a 10% by weight, 0.12 mmol) in ethanol (14 mL), following the experimental procedure described for the synthesis of Intermediate 7. The crude product was used without any further purification.

LRMS (m/z): 489 (M+1)+

Intermediate 166 tert-butyl 4-{[({1-[3-(4-{[4-({[tert-butyl(dimethyl)silyl]oxy}methyl)-2-chloro-5-methoxyphenyl]amino}-4-oxobutyl)phenyl]cyclohexyl}carbonyl)oxy]methyl}piperidine-1-carboxylate Obtained as a yellowish oil (129 mg, 40%) from 4-{3-[1-({[1-(tert-butoxycarbonyl)piperidin-4-yl]methoxy}carbonyl)cyclohexyl]phenyl}butanoic acid (Intermediate 165, 240 mg of the TFA salt, 0.49 mmol), 4-((tert-butyldimethylsilyloxy)methyl)-2-chloro-5-methoxyaniline (prepared according to experimental procedure described in patent WO201114180 for the synthesis of Intermediate 39, 171 mg, 0.57 mmol), DIEA (0.39 mL, 2.21 mmol) and HATU (243 mg, 0.64 mmol) following the experimental procedure described for the synthesis of Intermediate 12. Purification of the crude residue was performed by column chromatography over silica gel using a gradient of Hexane/Diethyl Ether.

LRMS (m/z): 772 (M+1)+

Intermediate 167 tert-butyl 4-{[({1-[3-(4-{[2-chloro-4-(hydroxymethyl)-5-methoxyphenyl]amino}-4-oxobutyl)phenyl]cyclohexyl}carbonyl)oxy]methyl}piperidine-1-carboxylate Obtained as a colorless oil (89 mg, 77%) from tert-butyl 4-{[({1-[3-(4-{[4-({[tert-butyl(dimethyl)silyl]oxy}methyl)-2-chloro-5-methoxyphenyl]amino}-4-oxobutyl)phenyl]cyclohexyl}carbonyl)oxy]methyl}piperidine-1-carboxylate (Intermediate 166, 123 mg, 0.16 mmol) and tetrabutylammonium fluoride (175 µL of a 1M solution in THF, 0.18 mmol) in THF (2 mL), following the experimental procedure described for the synthesis of Intermediate 81. The crude product was purified by column chromatography using a gradient of Hexane/Chloroform/Methanol.

LRMS (m/z): 658 (M+1)+

Intermediate 168 tert-butyl 4-[({[1-(3-{4-[(2-chloro-4-formyl-5-methoxyphenyl)amino]-4-oxobutyl}phenyl)cyclohexyl]carbonyl}oxy)methyl]piperidine-1-carboxylate Obtained as a pale yellow oil (88 mg, 95%) from tert-butyl 4-{[({1-[3-(4-{[2-chloro-4-(hydroxymethyl)-5-methoxyphenyl]amino}-4-oxobutyl)phenyl]cyclohexyl}carbonyl)oxy]methyl}piperidine-1-carboxylate (Intermediate 167, 89 mg, 0.14 mmol) and manganese dioxide (118 mg, 1.36 mmol) in chloroform (1.8 mL), following the experimental procedure described for the synthesis of Intermediate 31. No further purification was conducted in this case.
LRMS (m/z): 656 (M+1)+

Intermediate 169 tert-butyl 4-{[({1-[3-(4-{[4-({[(2R)-2-{[tert-butyl (dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl] cyclohexyl}carbonyl)oxy]methyl}piperidine-1-carboxylate Obtained as a viscous colorless foam (38 mg, 30%) from tert-butyl 4-[({[1-(3-{4-[(2-chloro-4-formyl-5-methoxyphenyl)amino]-4-oxobutyl}phenyl)cyclohexyl]carbonyl}oxy) methyl]piperidine-1-carboxylate (Intermediate 168, 85 mg, 0.13 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 51 mg, 0.13 mmol), sodium triacetoxyborohydride (71 mg, 0.33 mmol) and DIEA (23 µL, 0.13 mmol) in THF (2 mL), following the experimental procedure described for the synthesis of Intermediate 15. The crude residue was purified by column chromatography over silica gel using a gradient of Chloroform/Methanol from 50/1 to 15/1.
LRMS (m/z): 974 (M+1)+

Example 28 piperidin-4-ylmethyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl] amino}-4-oxobutyl)phenyl]cyclohexanecarboxylate Tert-butyl 4-{[({1-[3-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl] amino}-4-oxobutyl)phenyl]cyclohexyl}carbonyl)oxy] methyl}piperidine-1-carboxylate (Intermediate 169, 37 mg, 0.038 mmol) was dissolved in dioxane (1 mL) and hydrochloric acid was added (95 µL of a 4 M solution in dioxane, 0.38 mmol) under inert atmosphere. The reaction mixture was stirred at r.t. for 24 h. The solvent was the decanted and the oily residue was washed with dioxane twice. After decanting the solvent, acetonitrile (3 mL) was added and stirring was applied (30 min) to afford a pale beige precipitate. The precipitate is filtered and washed with acetonitrile and diethyl ether to yield the title compound (24 mg as a dihydrochloride salt, 70%) as a beige solid. No further purification was required.
LRMS (m/z): 760 (M+1)+
$^1$H NMR (300 MHz, DMSO-$d_6$) δ: 1.17-1.45 (m, 6H), 1.50-1.75 (m, 6H), 1.76-1.93 (m, 4H), 2.30-2.46 (m, 4H), 2.62 (t, 2H), 2.67-2.86 (m, 3H), 2.92-3.08 (m, 2H), 3.12-3.25 (m, 2H), 3.79 (s, 3H), 3.87 (d, 2H), 4.16 (m, 2H), 5.42 (m, 1H), 6.20 (broad s, 1H), 6.54 (d, J=10 Hz, 1H), 6.95-7.03 (d, 1H), 7.06-7.30 (m, 4H), 7.50 (s, 1H), 7.64 (s, 1H), 8.17 (d, J=10 Hz, 1H), 8.57 (broad s, 1H), 8.86 (broad t, 1H), 9.34 (broad s, 1H), 9.57 (s, 1H), 10.51 (broad s, 1H).

Intermediate 170

(1-methylpiperidin-4-yl)methyl 1-(3-bromophenyl)cyclohexanecarboxylate

Obtained as a colorless oil (362 mg, 65%) from 1-(3-bromophenyl)cyclohexanecarboxylic acid (Intermediate 2, 400 mg, 1.41 mmol), thionyl chloride (5.0 mL, 68.9 mmol), tert-butyl (1-methylpiperidine-4-yl)methanol (188 µL, 1.43 mmol) and butyl lithium (1.14 mL of a 1.6M solution in hexanes, 1.85 mmol) in toluene (6 mL) and THF (6 mL), following the experimental procedure described for the synthesis of Intermediate 3. Purification of the crude obtained was performed by column chromatography over silica gel using a gradient of Hexane/Chloroform/Methanol.
LRMS (m/z): 394 (M)+; 396 (M+2)+

Intermediate 171

(1-methylpiperidin-4-yl)methyl 1-{3-[(1E)-4-tert-butoxy-4-oxobut-1-en-1-yl] phenyl}cyclohexanecarboxylate Obtained as a yellow oil (326 mg, 78%) from (1-methylpiperidin-4-yl)methyl 1-(3-bromophenyl)cyclohexanecarboxylate (Intermediate 170, 360 mg, 0.92 mmol), tert-butyl but-3-enoate (156 mg, 0.96 mmol), tri-ortho-tolylphosphine (279 mg, 0.92 mmol), DIEA (289 µL, 1.65 mmol) and palladium acetate (124 mg, 0.55 mmol), following the experimental procedure described for the synthesis of Intermediate 6. Purification of the crude residue was performed by column chromatography over silica gel using as a gradient a mixture of eluents Chloroform/Methanol.
LRMS (m/z): 456 (M+1)+

Intermediate 172

(1-methylpiperidin-4-yl)methyl 1-[3-(4-tert-butoxy-4-oxobutyl)phenyl]cyclohexanecarboxylate Obtained as a yellowish oil (277 mg, 76%) from (1-methylpiperidin-4-yl)methyl 1-{3-[(1E)-4-tert-butoxy-4-oxobut-1-en-1-yl]phenyl}cyclohexanecarboxylate (Intermediate 171, 320 mg, 0.70 mmol) and palladium on carbon (89 mg of a 10% by weight, 0.08 mmol) in acetic acid (7 mL), following the experimental procedure described for the synthesis of Intermediate 7. No further purification was required in this step.
LRMS (m/z): 458 (M+1)+

Intermediate 173

4-[3-(1-{[(1-methylpiperidin-4-yl)methoxy] carbonyl}cyclohexyl)phenyl]butanoic acid Obtained as a brownish oil (271 mg as a trifluoroacetate salt, 100%) from (1-methylpiperidin-4-yl)methyl 1-[3-(4-tert-butoxy-4-oxobutyl)phenyl]cyclohexane carboxylate (Intermediate 172, 272 mg of the acetate salt, 0.53 mmol) and trifluoroacetic acid (0.4 mL, 5.26 mmol) in chloroform (3 mL), following the experimental procedure described for the synthesis of Intermediate 11. The crude product was used without any further purification.
LRMS (m/z): 400 (M−1)−

Intermediate 174

(1-methylpiperidin-4-yl)methyl 1-[3-(4-{[4-({[tert-butyl(dimethyl)silyl]oxy}methyl)-2-chloro-5-methoxyphenyl]amino}-4-oxobutyl)phenyl]cyclohexanecarboxylate Obtained as a colorless oil (197 mg, 52%) from 4-[3-(1-{[(1-methylpiperidin-4-yl)methoxy]carbonyl}cyclohexyl)

phenyl]butanoic acid (Intermediate 173, 265 mg of the TFA salt, 0.51 mmol), 4-((tert-butyldimethylsilyloxy)methyl)-2-chloro-5-methoxyaniline (prepared according to experimental procedure described in patent WO201114180 for the synthesis of Intermediate 39, 178 mg, 0.59 mmol), DIEA (0.40 mL, 2.30 mmol) and HATU (254 mg, 0.67 mmol) in chloroform (4 mL), following the experimental procedure described for the synthesis of Intermediate 12. Purification of the crude residue was performed by column chromatography over silica gel using a gradient of Chloroform/Methanol.

LRMS (m/z): 686 (M+1)+

Intermediate 175

(1-methylpiperidin-4-yl)methyl 1-[3-(4-{[2-chloro-4-(hydroxymethyl)-5-methoxyphenyl]amino}-4-oxobutyl)phenyl]cyclohexanecarboxylate Obtained as a viscous oil (112 mg, 67%) from (1-methylpiperidin-4-yl)methyl 1-[3-(4-{[4-({[tert-butyl(dimethyl)silyl]oxy}methyl)-2-chloro-5-methoxyphenyl]amino}-4-oxobutyl)phenyl]cyclohexanecarboxylate (Intermediate 17 μL, 195 mg, 0.28 mmol) and tetrabutylammonium fluoride (315 μL of a 1M solution in THF, 0.31 mmol) in THF (3.5 mL), following the experimental procedure described for the synthesis of Intermediate 81. The crude product was purified by column chromatography using a gradient of Chloroform/Methanol.

LRMS (m/z): 572 (M+1)+

Intermediate 176

(1-methylpiperidin-4-yl)methyl 1-(3-{4-[(2-chloro-4-formyl-5-methoxyphenyl)amino]-4-oxobutyl}phenyl)cyclohexanecarboxylate Obtained as a pale yellow oil (98 mg of an 80% purity, 71%) from (1-methylpiperidin-4-yl)methyl 1-[3-(4-{[2-chloro-4-(hydroxymethyl)-5-methoxyphenyl]amino}-4-oxobutyl)phenyl]cyclohexane carboxylate (Intermediate 175, 111 mg, 0.19 mmol) and Dess-Martin periodinane reagent (103 mg, 0.24 mmol) in chloroform (2.5 mL), following the experimental procedure described for the synthesis of Intermediate 14. Purification was performed by column chromatography over silica gel using a gradient of Chloroform/Methanol.

LRMS (m/z): 570 (M+1)+

Intermediate 177

(1-methylpiperidin-4-yl)methyl 1-[3-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl]cyclohexanecarboxylate Obtained as a yellow oil (87 mg, 70%) from (1-methylpiperidin-4-yl)methyl 1-(3-{4-[(2-chloro-4-formyl-5-methoxyphenyl)amino]-4-oxobutyl}phenyl)cyclohexanecarboxylate (Intermediate 176, 94 mg, 0.17 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 52 mg, 0.13 mmol), sodium triacetoxyborohydride (105 mg, 0.50 mmol) in THF (2 mL), following the experimental procedure described for the synthesis of Intermediate 15. The crude residue was purified by column chromatography over silica gel using a gradient of Chloroform/Methanol from 50/1 to 15/1.

LRMS (m/z): 888 (M+1)+

Example 29

(1-methylpiperidin-4-yl)methyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate Obtained as a beige solid (47 mg as a dihydrofluoride salt, 57%) from (1-methylpiperidin-4-yl)methyl 1-[3-(4-{[4-({[(2R)-2-{[tert-butyl(dimethyl)silyl]oxy}-2-(8-hydroxy-2-oxo-1,2-dihydroquinolin-5-yl(ethyl]amino}methyl)-2-chloro-5-methoxyphenyl]amino}-4-oxobutyl)phenyl]cyclohexanecarboxylate (Intermediate 177, 86 mg, 0.097 mmol) and triethylamine trihydrofluoride (80 μL, 0.49 mmol), following the experimental procedure described for the synthesis of Example 1. No additional purification was necessary for this example.

LRMS (m/z): 774 (M+1)+

$^1$H NMR (300 MHz, DMSO-$d_6$) δ: 1.13-1.50 (m, 7H), 1.50-1.75 (m, 5H), 1.80-1.95 (m, 4H), 2.15 (s, 3H), 2.26-2.44 (m, 4H), 2.55-2.66 (m, 3H), 2.66-2.79 (m, 4H), 3.70 (s, 2H), 3.72 (s, 3H), 3.85 (d, J=5.8 Hz, 2H), 5.06 (m, 1H), 6.48 (d, J=9.8 Hz, 1H), 6.91 (d, J=7.8 Hz, 1H), 7.05 (d, J=8.2 Hz, 1H), 7.09 (m, 1H), 7.16 (m, 2H), 7.24 (m, 1H), 7.34 (m, 2H), 8.12 (d, J=10.1 Hz, 1H), 9.40 (s, 1H), 10.35 (broad s, 1H).

Intermediate 178 tert-butyl N-[4-({[tert-butyl(dimethyl)silyl]oxy}methyl)-2-chloro-5-methoxyphenyl]glycinate To a solution of 4-((tert-butyldimethylsilyloxy)methyl)-2-chloro-5-methoxyaniline (prepared according to experimental procedure described in patent WO201114180 for the synthesis of Intermediate 39, 409 mg, 1.35 mmol) in DMF (4 mL) were added DIPEA (275 μL, 1.57 mmol) and tert-butyl 2-bromoacetate (220 μL, 1.49 mmol) and the reaction mixture was heated to 60° C. and temperature was maintained for 40 hours. Then, the solvent was removed under reduced pressure, and water and diethyl ether were added to the reaction mixture. The phases were separated, and the aqueous layer was further extracted with ether (3×30 mL). The combined organic extracts were washed with brine, dried over anhydrous sodium sulphate, filtered and concentrated to dryness to afford the title compound as a pale yellow oil (485 mg, 86%). The crude product was used in the next step without any further purification.

LRMS (m/z): 416 (M+1)+; 284 (M−131 (OTBS), tropylic cation)+

Intermediate 179 tert-butyl N-[2-chloro-4-(hydroxymethyl)-5-methoxyphenyl]glycinate

Obtained as a yellow foam (127 mg, 99%) from tert-butyl N-[4-({[tert-butyl(dimethyl)silyl]oxy}methyl)-2-chloro-5-methoxyphenyl]glycinate (Intermediate 178, 485 mg, 1.17 mmol) and tetrabutylammonium fluoride (1.6 mL of a 1M solution in THF, 1.6 mmol) in THF (5 mL), following the experimental procedure described for the synthesis of Intermediate 81. The compound was used without any further purification.

LRMS (m/z): 284 (M−17(OH), tropylic cation)+

Intermediate 180 tert-butyl N-(2-chloro-4-formyl-5-methoxyphenyl)glycinate

Obtained as a pale brownish foam (143 mg of a 60% purity, 68%) from tert-butyl N-[2-chloro-4-(hydroxymethyl)-5-methoxyphenyl]glycinate (Intermediate 179, 127 mg, 0.429 mmol) and Dess-Martin periodinane reagent (180 mg, 0.42 mmol) in dichloromethane (3 mL), following the experimental procedure described for the synthesis of Intermediate 14. No additional purification was performed in this case.

LRMS (m/z): 300 (M+1)+

Intermediate 181

N-(2-chloro-4-formyl-5-methoxyphenyl)glycine

Obtained as a brownish solid (78 mg of a 74% purity, 83%) from tert-butyl N-(2-chloro-4-formyl-5-methoxyphenyl)glycinate (Intermediate 180, 143 mg of a 60% purity, 0.29 mmol) and trifluoroacetic acid (200 μL, 2.60 mmol) in chloroform (2 mL), following the experimental procedure described for the synthesis of Intermediate 32, but carrying out the reaction at r.t. No additional purification was performed.

LRMS (m/z): 244 (M+1)+; 242 (M−1)−

Intermediate 182

(3R)-1-azabicyclo[2.2.2]oct-3-yl 1-[3-(3-{[N-(2-chloro-4-formyl-5-methoxyphenyl)glycyl]amino}propyl)phenyl]cyclohexanecarboxylate Obtained as a brownish foam (178 mg of a 42% purity, 53%) from (3R)-1-azabicyclo[2.2.2]oct-3-yl 1-[3-(3-aminopropyl)phenyl]cyclohexanecarboxylate (Intermediate 127, 102 mg, 0.28 mmol), N-(2-chloro-4-formyl-5-methoxyphenyl)glycine (Intermediate 181, 78 mg of a 74% purity, 0.24 mmol), DIEA (170 μL, 0.98 mmol) and HATU (110 mg, 0.29 mmol) in a mixture of chloroform (3 mL) and DMF (1 mL), following the experimental procedure described for the synthesis of Intermediate 12. The crude residue was used without any further purification.

LRMS (m/z): 596 (M+1)+

Intermediate 183

(3R)-1-azabicyclo[2.2.2]oct-3-yl 1-{3-[3-({N-[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]glycyl}amino)propyl]phenyl}cyclohexanecarboxylate Obtained as a brownish foam (65 mg of a 74% purity, 40%) from (3R)-1-azabicyclo[2.2.2]oct-3-yl 1-[3-(3-{[N-(2-chloro-4-formyl-5-methoxyphenyl)glycyl]amino}propyl)phenyl]cyclohexanecarboxylate (Intermediate 182, 178 mg of a 42% purity, 0.13 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 52 mg, 0.13 mmol), sodium triacetoxyborohydride (80 mg, 0.38 mmol) in a mixture of methanol (2 mL) and THF (2 mL), following the experimental procedure described for the synthesis of Intermediate 15. The crude residue was purified by column chromatography over silica gel using a gradient of Chloroform and Chloroform/Methanol/Ammonia 40/8/1.

LRMS (m/z): 915 (M+1)+

Example 30

(3R)-1-azabicyclo[2.2.2]oct-3-yl 1-{3-[3-({N-[2-chloro-4-({[(2R)-2-hydroxy-2-(8-hydroxy-2-oxo-1,2-dihydroquinolin-5-yl)ethyl]amino}methyl)-5-methoxyphenyl]glycyl}amino)propyl]phenyl}cyclohexanecarboxylate Obtained as a yellow solid (10 mg as a free base, 24%) from (3R)-1-azabicyclo[2.2.2]oct-3-yl 1-{3-[3-({N-[4-({[(2R)-2-{[tert-butyl(dimethyl)silyl]oxy}-2-(8-hydroxy-2-oxo-1,2-dihydroquinolin-5-yl(ethyl]amino}methyl)-2-chloro-5-methoxyphenyl]glycyl}amino)propyl]phenyl}cyclohexanecarboxylate (Intermediate 183, 65 mg, 0.05 mmol) and triethylamine trihydrofluoride (25 μL, 0.15 mmol), following the experimental procedure described for the synthesis of Example 1. The crude product was purified by reverse phase column chromatography over C18 modified silica gel using a gradient of Water (containing a 0.1% of aqueous ammonia) and Methanol.

LRMS (m/z): 800 (M+1)+

$^1$H NMR (300 MHz, DMSO-$d_6$) δ: 1.0-1.30 (m, 6H), 1.30-1.50 (m, 4H), 1.50-1.73 (m, 5H), 1.77 (m, 1H), 2.18-2.42 (m, 3H), 2.42-2.64 (m, 5H), 2.80-3.05 (m, 3H), 3.11 (m, 2H), 3.58 (s, 2H), 3.67 (s, 3H), 3.78 (s, 2H), 4.64 (m, 1H), 5.03 (m, 1H), 5.57 (s, 1H), 6.12 (s, 1H), 6.47 (d, J=9.8 Hz, 1H), 6.92 (d, 1H), 7.02 (m, 2H), 7.13-7.18 (m, 4H), 8.11 (d, J=9.9 Hz, 1H), 10.31 (broad s, 1H).

Intermediate 184

(3R)-1-azabicyclo[2.2.2]oct-3-yl 1-(4-bromophenyl)cyclohexanecarboxylate

Obtained as a brownish solid (970 mg, 69%) from 1-(4-bromophenyl)cyclohexanecarboxylic acid (Intermediate 2, 1.0 g, 3.53 mmol), thionyl chloride (13 mL, 179 mmol), (3R)-1-azabicyclo[2.2.2]octan-3-ol (450 mg, 3.54 mmol) and butyl lithium (2.90 mL of a 1.6M solution in hexanes, 4.64 mmol), following the experimental procedure described for the synthesis of intermediate 3. The compound was used as is without any further purification.

LRMS (m/z): 392/394 (M/M+2)+

Intermediate 185

(3R)-1-azabicyclo[2.2.2]oct-3-yl 1-{4-[(1E)-4-tert-butoxy-4-oxobut-1-en-1-yl]phenyl}cyclohexanecarboxylate Obtained as a pale yellow foam (1.15 g, 93%) from (3R)-1-azabicyclo[2.2.2]oct-3-yl 1-(4-bromophenyl)cyclohexanecarboxylate (Intermediate 184, 965 mg, 2.46 mmol), tert-butyl but-3-enoate (400 μL, 2.48 mmol), tri-ortho-tolylphosphine (300 mg, 0.98 mmol), DIEA (775 μL, 4.43 mmol) and palladium acetate (110 mg, 0.49 mmol) in acetonitrile (9 mL), following the experimental procedure described for the synthesis of Intermediate 6. Purification of the crude residue was performed by column chromatography over silica gel using a gradient of eluents Hexane:Chloroform:Methanol.
LRMS (m/z): 454 (M+1)+

Intermediate 186

(3R)-1-azabicyclo[2.2.2]oct-3-yl 1-[4-(4-tert-butoxy-4-oxobutyl)phenyl]cyclohexanecarboxylate Obtained as a beige foam (1.04 g, acetate salt, 72%) from (3R)-1-azabicyclo[2.2.2]oct-3-yl 1-{4-[(1E)-4-tert-butoxy-4-oxobut-1-en-1-yl]phenyl}cyclohexanecarboxylate (Intermediate 185, 1.15 g, 2.54 mmol) and palladium on carbon (0.54 g of a 10% by weight, 0.51 mmol) in a mixture of acetic acid (8.5 mL) and THF (8.5 mL), following the experimental procedure described for the synthesis of Intermediate 7. The crude product was used without any further purification.
LRMS (m/z): 456 (M+1)+

Intermediate 187

4-[4-(1-{[(3R)-1-azabicyclo[2.2.2]oct-3-yloxy]carbonyl}cyclohexyl)phenyl]butanoic acid Obtained as a brownish oil (1.2 g of the TFA salt, 87%) from (3R)-1-azabicyclo[2.2.2]oct-3-yl 1-[4-(4-tert-butoxy-4-oxobutyl)phenyl]cyclohexanecarboxylate (Intermediate 186, 1.04 g, 2.29 mmol) and trifluoroacetic acid (1.76 mL, 22.8 mmol) in chloroform (12 mL), following the experimental procedure described for the synthesis of Intermediate 11. The crude product was used as such without any further purification.
LRMS (m/z): 400 (M+1)+

Intermediate 188

(3R)-1-azabicyclo[2.2.2]oct-3-yl 1-[4-(4-{[4-({[tert-butyl(dimethyl)silyl]oxy}methyl)-2-chloro-5-methoxyphenyl]amino}-4-oxobutyl)phenyl]cyclohexanecarboxylate Obtained as a yellowish oil (640 mg, 48%) from 4-[4-(1-{[(3R)-1-azabicyclo[2.2.2]oct-3-yloxy]carbonyl}cyclohexyl)phenyl]butanoic acid (Intermediate 187, 1.2 g of the TFA salt, 3.0 mmol), 4-((tert-butyldimethylsilyloxy)methyl)-2-chloro-5-methoxyaniline (prepared according to experimental procedure described in patent WO201114180 for the synthesis of Intermediate 39, 860 mg, 2.84 mmol), DIEA (2.1 mL, 12.1 mmol) and HATU (1.34 g, 3.52 mmol) in chloroform (13 mL), following the experimental procedure described for the synthesis of Intermediate 12. Purification was performed by column chromatography over silica gel using a gradient of Chloroform and Chloroform/Methanol/Ammonia 40/8/1.
LRMS (m/z): 684 (M+1)+

Intermediate 189

(3R)-1-azabicyclo[2.2.2]oct-3-yl 1-[4-(4-{[2-chloro-4-(hydroxymethyl)-5-methoxyphenyl]amino}-4-oxobutyl)phenyl]cyclohexanecarboxylate Obtained as a yellowish foam (199 mg, 96%) from (3R)-1-azabicyclo[2.2.2]oct-3-yl 1-[4-(4-{[4-({[tert-butyl(dimethyl)silyl]oxy}methyl)-2-chloro-5-methoxyphenyl]amino}-4-oxobutyl)phenyl]cyclohexanecarboxylate (Intermediate 188, 250 mg, 0.37 mmol) and tetrabutylammonium fluoride (440 µL of a 1M solution in THF, 0.44 mmol) in THF (3.5 mL), following the experimental procedure described for the synthesis of Intermediate 81. The crude product was used as is without any further purification.
LRMS (m/z): 569 (M+1)+

Intermediate 190

(3R)-1-azabicyclo[2.2.2]oct-3-yl 1-(4-{4-[(2-chloro-4-formyl-5-methoxyphenyl)amino]-4-oxobutyl}phenyl)cyclohexanecarboxylate Obtained as a pale yellowish foam (192 mg, 98%) from (3R)-1-azabicyclo[2.2.2]oct-3-yl 1-[4-(4-{[2-chloro-4-(hydroxymethyl)-5-methoxyphenyl]amino}-4-oxobutyl)phenyl]cyclohexanecarboxylate (Intermediate 189, 195 mg, 0.34 mmol) and Dess-Martin periodinane reagent (182 mg, 0.42 mmol) in chloroform (4.5 mL), following the experimental procedure described for the synthesis of Intermediate 14. No additional purification was performed in this case.
LRMS (m/z): 567 (M+1)+

Intermediate 191

(3R)-1-azabicyclo[2.2.2]oct-3-yl 1-[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl]cyclohexanecarboxylate Obtained as a brownish foam (294 mg of an 84% purity, 82%) from (3R)-1-azabicyclo[2.2.2]oct-3-yl 1-(4-{4-[(2-chloro-4-formyl-5-methoxyphenyl)amino]-4-oxobutyl}phenyl)cyclohexanecarboxylate (Intermediate 190, 192 mg, 0.34 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 113 mg, 0.34 mmol), sodium triacetoxyborohydride (290 mg, 1.37 mmol) in a mixture of methanol (2.8 mL) and THF (0.5 mL), following the experimental procedure described for the synthesis of Intermediate 15. The crude residue was used as such without any further purification.
LRMS (m/z): 886 (M+1)+; 884 (M−1)−

Example 31

(3R)-1-azabicyclo[2.2.2]oct-3-yl 1-[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate Obtained as a white solid (277 mg as a dihydrofluoride salt, 70%) from (3R)-1-azabicyclo[2.2.2]oct-3-yl 1-[4-(4-{[4-({[(2R)-2-{[tert-butyl(dimethyl)silyl]oxy}-2-(8-hydroxy-2-oxo-1,2-dihydroquinolin-5-yl(ethyl]amino}methyl)-2-chloro-5-methoxyphenyl]amino}-4-oxobutyl)phenyl]cyclohexanecarboxylate (Intermediate 191, 294 mg of an 84% purity, 0.33 mmol) and triethylamine trihydrofluoride (140 µL, 0.86 mmol), following the experimental procedure described for the synthesis of Example 1. In this instance purification by column chromatography was not required.
LRMS (m/z): 772 (M+1)+

¹H NMR (300 MHz, DMSO-d$_6$) δ: 1.15-1.35 (m, 3H), 1.35-1.50 (m, 4H), 1.50-1.77 (m, 6H), 1.80-1.95 (m, 3H), 2.25-2.45 (m, 5H), 2.55-2.75 (m, 5H), 2.80-3.05 (m, 2H), 3.05-3.10 (m, 1H), 3.70 (s, 2H), 3.72 (s, 3H), 4.68 (m, 1H), 5.07 (m, 1H), 6.48 (d, J=10 Hz, 1H), 6.91 (d, J=8 Hz, 1H), 7.06 (d, J=8 Hz, 1H), 7.18-7.21 (d, 2H), 7.30-7.33 (d, 2H), 7.34 (m, 2H), 8.12 (d, J=10 Hz, 1H), 9.44 (s, 1H), 10.3 (broad s, 1H).

Intermediate 192

1-(3-bromophenyl)cyclopentanecarbonitrile

Obtained as a pale beige oil (6.0 g, 92%) from 2-(3-bromophenyl)acetonitrile (5.0 g, 25.5 mmol), 1,4-dibromobutane (3.1 mL, 25.2 mmol) and sodium hydride (2.55 g of a 60% dispersion in oil, 106.3 mmol) in THF (70 mL), following the experimental procedure described for the synthesis of Intermediate 1.
1H NMR (300 MHz, Chloroform-d) δ 7.59 (br s, 1H), 7.4 (t, J=8.5 Hz, 2H), 7.26 (t, J=8.5 Hz, 1H), 2.64-2.34 (m, 2H), 2.21-1.83 (m, 6H).

Intermediate 193

1-(3-bromophenyl)cyclopentanecarboxylic acid

Obtained as a pale brownish solid (5.9 g, 91%) from 1-(3-bromophenyl)cyclopentanecarbonitrile (Intermediate 192, 6.0 g, 24.0 mmol), and KOH (40 mL of a 10M aqueous solution, 0.4 mol) in ethyleneglycol (70 mL), following the experimental procedure described for the synthesis of Intermediate 2.
LRMS (m/z): 267/269 (M−1)−; 313/315 (M+45[HC-COO⁻])−

Intermediate 194

(3R)-1-azabicyclo[2.2.2]oct-3-yl 1-(3-bromophenyl)cyclopentanecarboxylate

Obtained as a pale brownish solid (947 mg, 64%) from 1-(3-bromophenyl)cyclopentanecarboxylic acid (Intermediate 193, 1.0 g, 3.53 mmol), thionyl chloride (13 mL, 179 mmol), (3R)-1-azabicyclo[2.2.2]octan-3-ol (470 mg, 3.70 mmol) and butyl lithium (3.0 mL of a 1.6M solution in hexanes, 4.8 mmol), following the experimental procedure described for the synthesis of intermediate 3. The compound was used as is without any further purification.
LRMS (m/z): 378/380 (M/M+2)+

Intermediate 195

(3R)-1-azabicyclo[2.2.2]oct-3-yl 1-{3-[(1E)-4-tert-butoxy-4-oxobut-1-en-1-yl]phenyl}cyclopentanecarboxylate Obtained as a pale brownish solid (412 mg of a 90% purity, 80%) from (3R)-1-azabicyclo[2.2.2]oct-3-yl 1-(3-bromophenyl)cyclopentanecarboxylate (Intermediate 194, 400 mg, 1.06 mmol), tert-butyl but-3-enoate (179 μL, 1.11 mmol), tri-ortho-tolylphosphine (322 mg, 1.06 mmol), DIEA (332 μL, 1.90 mmol) and palladium acetate (142 mg, 0.63 mmol) in acetonitrile (3.8 mL), following the experimental procedure described for the synthesis of Intermediate 6. Purification of the crude residue was performed by column chromatography over silica gel using a gradient of eluents Hexane:Chloroform:Methanol.
LRMS (m/z): 440 (M+1)+

Intermediate 196

(3R)-1-azabicyclo[2.2.2]oct-3-yl 1-[3-(4-tert-butoxy-4-oxobutyl)phenyl]cyclopentanecarboxylate Obtained as a beige solid (420 mg, acetate salt, 78%) from (3R)-1-azabicyclo[2.2.2]oct-3-yl 1-{3-[(1E)-4-tert-butoxy-4-oxobut-1-en-1-yl]phenyl}cyclopentanecarboxylate (Intermediate 195, 412 mg, 2.54 mmol) and palladium on carbon (119 mg of a 10% by weight, 0.11 mmol) in acetic acid (9.5 mL), following the experimental procedure described for the synthesis of Intermediate 7. The crude product was used without any further purification.
LRMS (m/z): 442 (M+1)+

Intermediate 197

4-[3-(1-{[(3R)-1-azabicyclo[2.2.2]oct-3-yloxy]carbonyl}cyclopentyl)phenyl]butanoic acid Obtained as a beige oil (528 mg of the TFA salt, 100%) from (3R)-1-azabicyclo[2.2.2]oct-3-yl 1-[3-(4-tert-butoxy-4-oxobutyl)phenyl]cyclopentanecarboxylate (Intermediate 196, 420 mg, 0.95 mmol) and trifluoroacetic acid (0.73 mL, 9.5 mmol) in chloroform (5.5 mL), following the experimental procedure described for the synthesis of Intermediate 11. The crude product was used as such without any further purification.
LRMS (m/z): 386 (M+1)+

Intermediate 198

(3R)-1-azabicyclo[2.2.2]oct-3-yl 1-[3-(4-{[4-({[tert-butyl(dimethyl)silyl]oxy}methyl)-2-chloro-5-methoxyphenyl]amino}-4-oxobutyl)phenyl]cyclopentanecarboxylate Obtained as a colorless oil (398 mg, 52%) from 4-[3-(1-{[(3R)-1-azabicyclo[2.2.2]oct-3-yloxy]carbonyl}cyclopentyl)phenyl] butanoic acid (Intermediate 197, 520 mg of the TFA salt, 1.04 mmol), 4-((tert-butyldimethylsilyloxy)methyl)-2-chloro-5-methoxyaniline (prepared according to experimental procedure described in patent WO201114180 for the synthesis of Intermediate 39, 361 mg, 1.19 mmol), DIEA (0.82 mL, 4.7 mmol) and HATU (515 mg, 1.35 mmol) in chloroform (8 mL), following the experimental procedure described for the synthesis of Intermediate 12. Purification was performed by column chromatography over silica gel using a gradient of Chloroform and Chloroform/Methanol/Ammonia 40/8/1.
LRMS (m/z): 670 (M+1)+

Intermediate 199

(3R)-1-azabicyclo[2.2.2]oct-3-yl 1-[3-(4-{[2-chloro-4-(hydroxymethyl)-5-methoxyphenyl]amino}-4-oxobutyl)phenyl]cyclopentanecarboxylate Obtained as a yellowish oil (318 mg of an 93% purity, 90%) from (3R)-1-azabicyclo[2.2.2]oct-3-yl 1-[3-(4-{[4-({[tert-butyl(dimethyl)silyl]oxy}methyl)-2-chloro-5-methoxyphenyl]amino}-4-oxobutyl)phenyl]cyclopentanecarboxylate (Intermediate 198, 398 mg, 0.59 mmol) and triethylamine trihydrofluoride (363 μL, 2.23 mmol) in THF (11 mL), following the experimental procedure described for the synthesis of Intermediate 13. Purification of the work-up residue was performed by column chromatography over silica gel using a gradient of Chloroform/Methanol starting with Chloroform and continuing with Chloroform/Methanol 25/1 to Chloroform/Methanol 15/1 to provide the title compound.

LRMS (m/z): 555 (M+1)+; 553 (M−1)−

Intermediate 200

(3R)-1-azabicyclo[2.2.2]oct-3-yl 1-(3-{4-[(2-chloro-4-formyl-5-methoxyphenyl)amino]-4-oxobutyl}phenyl)cyclopentanecarboxylate Obtained as a yellowish oil (276 mg of an 83% purity, 73%) from (3R)-1-azabicyclo[2.2.2]oct-3-yl 1-[3-(4-{[2-chloro-4-(hydroxymethyl)-5-methoxyphenyl]amino}-4-oxobutyl)phenyl]cyclopentanecarboxylate (Intermediate 199, 315 mg, 0.57 mmol) and Dess-Martin periodinane reagent (301 mg, 0.71 mmol) in Chloroform (7.5 mL), following the experimental procedure described for the synthesis of Intermediate 14. Purification of the work-up residue was performed by column chromatography over silica gel using a gradient of Chloroform/Methanol starting with Chloroform and continuing with Chloroform/Methanol 50/1 to Chloroform/Methanol 25/1 to Chloroform/Methanol 15/1 to provide the title compound.

LRMS (m/z): 553 (M+1)+; 551 (M−1)−

Intermediate 201

(3R)-1-azabicyclo[2.2.2]oct-3-yl 1-[3-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl]cyclopentanecarboxylate Obtained as a yellow dry foam (282 mg of an 82% purity, 54%) from (3R)-1-azabicyclo[2.2.2]oct-3-yl 1-(3-{4-[(2-chloro-4-formyl-5-methoxyphenyl)amino]-4-oxobutyl}phenyl)cyclopentanecarboxylate (Intermediate 200, 270 mg, 0.49 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 193 mg, 0.49 mmol), sodium triacetoxyborohydride (390 mg, 1.84 mmol) in a mixture of methanol (2.6 mL) and THF (1.3 mL), following the experimental procedure described for the synthesis of Intermediate 15. Purification of the obtained residue was performed by column chromatography over silica gel using a gradient of Chloroform/Methanol starting with Chloroform and continuing with Chloroform/Methanol 50/1 to Chloroform/Methanol 4/1 to provide the title compound.

LRMS (m/z): 871 (M+1)+; 869 (M−1)−

Example 32

(3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclopentanecarboxylate Obtained as a white solid (170 mg as a dihydrofluoride salt, 78%) from (3R)-1-azabicyclo[2.2.2]oct-3-yl 1-[3-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)phenyl]cyclopentanecarboxylate (Intermediate 201, 282 mg of an 82% purity, 0.27 mmol) and triethylamine trihydrofluoride (264 μL, 1.62 mmol) in THF (10 mL), following the experimental procedure described for the synthesis of Example 1. In this instance purification by column chromatography was not required.

LRMS (m/z): 757 (M+1)+, 755 (M−1)−

$^1$H NMR (300 MHz, DMSO-$d_6$) δ: 1.22 (m, 2H), 1.30-1.45 (m, 3H), 1.45-1.55 (m, 1H), 1.55-1.75 (m, 4H), 1.75-1.90 (m, 4H), 2.25-2.30 (m, 1H), 2.30-2.40 (t, 2H), 2.43 (m, 1H), 2.55-2.70 (m, 6H), 2.80-3.10 (m, 3H), 3.69 (s, 2H), 3.72 (s, 3H), 4.56-4.66 (m, 1H), 5.0-5.10 (m, 1H), 6.48 (d, J=10 Hz, 1H), 6.90 (d, J=8 Hz, 1H), 7.05 (d, J=8 Hz, 1H), 7.09-7.16 (m, 3H), 7.19 (s, 1H), 7.23-7.28 (m, 1H), 7.31 (s, 1H), 7.33 (s, 1H), 8.12 (d, J=10 Hz, 1H), 9.43 (s, 1H).

Biological Tests

Test 1: Human Adrenergic $β_1$ and $β_2$ Receptor Binding Assays

The study of binding to human adrenergic beta1 and beta2 receptors was performed using commercial membranes prepared from Sf9 cells where they are overexpressed (Perkin Elmer). The membrane suspensions (16 μg/well for beta1 and 5 μg/well for beta2) in assay buffer (75 mM Tris/HCl with 12.5 mM MgCl2 and 2 mM EDTA pH=7.4) were incubated with 0.14 or 0.6 nM of 3H-CGP$_{12177}$ (Amersham) for beta 1 and beta 2 receptors respectively in a final volume of 250 μl, in GFC Multiscreen 96 well plates (Millipore) previously treated with assay buffer containing 0.3% PEI (Sigma). Non specific binding was measured in the presence of 1 μM propanolol. Incubation was maintained for 60 minutes at room temperature and with gentle shaking. The binding reactions were terminated by filtration and washing with 2.5 volumes of Tris/HCl 50 mM pH=7.4. The affinity of each test compound to the receptor was determined by using ten different concentrations ran in duplicate. IC50s were calculated using Activity Base software from IDBS and the four parameters-log equation.

Compounds of the present invention were found to have $IC_{50}$ values less than 10 nM for $β_2$ receptor and more than 60 nM for β1 receptor, with 81/82 ratios from 3 to 25.

Test 2: Human Muscarinic M3 Receptors Binding Assays

The study of binding to human muscarinic M3 receptors was performed using commercial membranes (Perkin Elmer) prepared from CHO-K1 cells.

Radioligand binding experiments were conducted in 96 polypropylene well plates in a total volume of 200 μl. All reagents were dissolved in assay binding buffer (PBS with calcium and magnesium, SIGMA), except compounds that were dissolved in DMSO 100%. Non-specific binding (NSB) was measured in the presence of 1 μM atropine. [3H]-NM, used as the radioligand was incubated with membranes that express human muscarinic M3 at concentration of 4.9 μg/well.

After an incubation period of two hours with gentle shaking, 150 μl of the reaction mix were transferred to 96 GF/C filter plates (Millipore), previously treated with wash buffer (Tris 50 mM; NaCl 100 mM; pH: 7.4), containing 0.05% PEI (Sigma) during one hour. Bound and free [3H]-NMS were separated by rapid vacuum filtration in a manifold from Millipore and washed four times with ice cold wash buffer. After drying 30 min, 30 μl of OPTIPHASE Supermix were added to each well and radioactivity quantified using a Microbeta microplate scintillation counter.

The affinity of each test compound to the receptor was determined by using ten different concentrations ran in duplicate. IC50s were calculated using Activity Base software from IDBS and the four parameters-log equation.

In the table 1 are shown some 1050 values for $\beta_2$ and $M_3$ bindings.

TABLE 1

| Example | Binding, IC$_{50}$, nM | |
|---|---|---|
| | $\beta_2$ | $M_3$ |
| 1 | 4.3 | 1.6 |
| 2 | 3 | 0.22 |
| 3 | 4.2 | 1.7 |
| 4 | 6.6 | 0.74 |
| 5 | 28 | 1.1 |
| 7 | 6.7 | 1.5 |
| 9 | 3.5 | 0.95 |
| 10 | 7.3 | 0.88 |
| 11 | 23 | 0.49 |
| 12 | 10 | 2.1 |
| 13 | 4.4 | 0.62 |
| 14 | 9 | 7.1 |
| 18 | 2.3 | 0.14 |
| 20 | 3.8 | 0.14 |
| 21 | 34 | 0.6 |
| 22 | 7.8 | 0.29 |
| 23 | 26 | 0.61 |
| 24 | 1.9 | 0.33 |
| 26 | 3 | 0.53 |
| 28 | 2.2 | 0.36 |
| 29 | 2.2 | 0.57 |
| 30 | 13 | 1.5 |
| 31 | 4 | 0.41 |

Pharmaceutical Compositions

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Packaging of the formulation may be suitable for single unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly small reservoir, cartridges or hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported.

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e. g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described in the following patent applications Nos.: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e. g. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with.

Such atomisers are described, for example, in PCT Patent Application No. WO 91/14468 and International Patent Application No. WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e. g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants, for example, oleic acid or lecithin and cosolvens, for example, ethanol. Pressurised formulations will generally be retained in a canister (for example, an aluminium canister) closed with a valve (for example, a metering valve) and fitted into an actuator provided with a mouthpiece.

Medicaments for administration by inhalation desirably have a controlled particle size. The optimum particle size for inhalation into the bronchial system is usually 1-10µ, preferably 2-5µ. Particles having a size above 20µ are generally too large when inhaled to reach the small airways. To achieve these particle sizes the particles of the active ingredient as produced may be size reduced by conventional means, for example, by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e. g. a fluorocarbon polymer as described in WO96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day.

The invention also provides a combination product comprising (i) at least a compound of the invention as described herein, and (ii) one ore more active ingredients. Examples of active ingredients that can be combined with compounds of the present invention are: corticosteroids, glucocorticoids, antihistamines, chemokine receptor antagonists, CRTH2 antagonists, leukotriene receptor antagonists, JAK inhibitors, Syk inhibitors, PDE4 inhibitors, $P_{13}K$ inhibitors, p38 inhibitors, PKC inhibitors, 5-lipoxygenase activating protein inhibitors, 5-lipoxygenase inhibitors, CYSLTR1 antagonists, CYSLTR2 antagonists, BLT1 antagonists, BLT2 antagonists, thromboxane A2 antagonists, DP1 receptor antagonists, DP1 receptor agonists, IP receptor agonists, Anti-IgE, IL5 antibody, leukotriene formation inhibitors, decongestants, mucolytics, antitussives, analgesics and expectorants.

The combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active compounds in the combination may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive lung diseases or for the treatment of asthma.

Additional suitable carriers for formulations of the active compounds of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

FORMULATION EXAMPLES

Formulation Example 1 (Oral Suspension)

| Ingredient | Amount |
| --- | --- |
| Active Compound | 3 mg |
| Citric acid | 0.5 g |
| Sodium chloride | 2.0 g |

-continued

| Ingredient | Amount |
| --- | --- |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2 (Hard Gelatine Capsule for Oral Administration)

| Ingredient | Amount |
| --- | --- |
| Active Compound | 1 mg |
| Lactose | 150 mg |
| Magnesium stearate | 3 mg |

Formulation Example 3 (Gelatin Cartridge for Inhalation)

| Ingredient | Amount |
| --- | --- |
| Active Compound (micronized) | 0.2 mg |
| Lactose | 25 mg |

Formulation Example 4 (Formulation for Inhalation with a DPI)

| Ingredient | Amount |
| --- | --- |
| Active Compound (micronized) | 15 mg |
| Lactose | 3000 mg |

Formulation Example 5 (Formulation for a MDI)

| Ingredient | Amount |
| --- | --- |
| Active Compound (micronized) | 10 g |
| 1,1,1,2,3,3,3-heptafluoro-n-propane | q.s. to 200 ml |

The invention claimed is:

1. A compound of Formula (A), or a pharmaceutically acceptable salt, or N-oxide, or isotopically-labeled derivate thereof:

Formula (A)

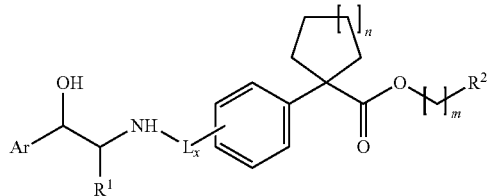

wherein:
Ar is chosen from a $C_{3-10}$ saturated or unsaturated, mono- or bicyclic cycloalkyl group, a $C_5$-$C_{14}$ mono- or bicyclic aryl group, a 3- to 14-membered saturated or unsaturated mono- or bicyclic heterocyclyl group having one or more heteroatoms selected from N, S, and O, a 5- to 14-membered mono- or bicyclic heteroaryl group having one or more heteroatoms chosen from N, S, and O; and wherein the cyclic groups independently are optionally substituted with one or more substituents chosen from a halogen atom, a cyano group, a nitro group, an oxo group, a carboxy group, a $C_{1-4}$ alkyl group, a $C_{1-4}$ alkoxy group, —$CF_3$, —$OCF_3$, —$NR^eR^f$, —$(CH_2)_p$—OH, —$NR^e(CO)R^f$, —$NR^e$—$SO_2$—$R^g$, —$SO_2NR^eR^f$, —$OC(O)R^h$ and —$NR^e(CH_2)_{(0-2)}$—$R^i$, wherein p is 0, 1 or 2 and wherein:

$R^e$ and $R^f$ are independently chosen from a hydrogen atom and a linear or branched $C_{1-4}$ alkyl group, $R^g$ is chosen from the group consisting of a linear or branched $C_{1-4}$ alkyl group, a $C_{6-5}$ aryl group, a saturated or unsaturated $C_{3-8}$ cycloalkyl; wherein the cyclic groups independently are optionally substituted with one or more substituents chosen from a halogen atom, a $C_{1-4}$ alkyl group, and a $C_{1-4}$ alkoxy group, $R^h$ is chosen from a hydrogen atom, —$NR^eR^f$ and a $C_{5-6}$ aryl group which is optionally substituted with one or more substituents chosen from a $C_{1-4}$ alkyl group and a $C_{1-4}$ alkoxy group, $R^i$ is chosen from the group consisting of a $C_{5-6}$ aryl group, a $C_{3-8}$ cycloalkyl group and a 3 to 8 membered saturated or unsaturated heterocyclyl group, which groups independently are optionally substituted with one or more substituents chosen from a halogen atom, a $C_{1-4}$ alkyl group, and a $C_{1-4}$ alkoxy group, $R^1$ is chosen from the group consisting of a hydrogen atom, a linear or branched $C_{1-4}$ alkyl group, and a linear or branched $C_{1-4}$ alkoxy group, $R^2$ is:

a)

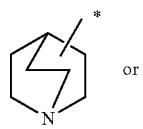

or b)

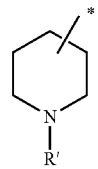

wherein:
R' is chosen from a hydrogen atom or a linear or branched $C_{1-4}$ alkyl group,
* is a point of attachment of $R^2$ to the remainder of the molecule of Formula (A),
n is 0, 1, 2 or 3,
m is 0, 1 or 2,
$L_x$ is a suitable covalent linker.

2. The compound according to claim 1, wherein $L_x$ is Formula (La) or Formula (Lb):

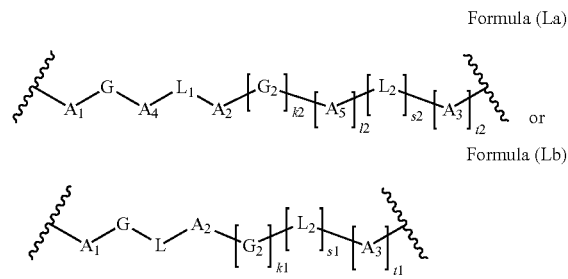

wherein k1, k2, s1, s2, l2, t1, and t2 are independently 0 or 1;
$A_1$, $A_2$, $A_3$, $A_4$ and $A_5$ are independently chosen from a direct bond, a $C_{1-10}$ alkylene group, a $C_{2-10}$ alkenylene group and a $C_{2-10}$ alkynylene group, wherein said groups are optionally substituted with one or more substituents chosen from a halogen atom, a hydroxy group, a linear or branched $C_{1-4}$ alkyl group, a linear or branched $C_{1-4}$ alkoxy group, a $C_{5-6}$ aryl group, and a $C_{3-7}$ cycloalkyl group,
L, $L_1$ and $L_2$ are independently chosen from a direct bond, —O—, —$NR^c$—, —S—, —S(O)—, —$SO_2$—, —$NR^c(CO)$—, —$(CO)NR^c$—, —$NR^c(CO)(CH_2)_qO$—, —$O(CH_2)_q(CO)NR^c$—, —$O(CH_2)_q(CO)O$—, —$O(CO)(CH_2)_qO$—, —$NR^c(CH_2)_q(CO)NR^c$—, —$NR^c(CO)(CH_2)_qNR^c(CO)$—, —$O(CH_2)_qNR^c$—, —$NR^c(CH_2)_qO$—, —$NR^c(CO)NR^d$—, —C(O)—, —C(O)O—, —OC(O)—, —$S(O)_2NR^c$—, —$NR^cS(O)_2$—, —$NR^cS(O)_2NR^d$—, —$C(O)NR^cS(O)_2$—, and —$S(O)_2NR^cC(O)$—, wherein $R^c$ and $R^d$ are independently chosen from a hydrogen atom and a linear or branched $C_{1-4}$ alkyl group and q is 0, 1, 2, 3 or 4,
G and $G_2$ are independently chosen from a direct bond; a $C_{3-10}$ mono- or bicyclic cycloalkyl group; a $C_5$-$C_{14}$ mono- or bicyclic aryl group; a 3 to 14-membered saturated or unsaturated mono- or bicyclic heterocyclyl group having one or more heteroatoms chosen from N, S, and O; a 5- to 14-membered mono- or bicyclic heteroaryl group having one or more heteroatoms chosen from N, S, and O; and a bicyclic ring system comprising two monocyclic ring systems which are linked between each other by a covalent bond; wherein said monocyclic ring systems are independently chosen from a $C_{3-8}$ cycloalkyl group; a $C_{5-6}$ aryl group; a 3 to 8-membered saturated or unsaturated heterocyclyl group having one or more heteroatoms chosen from N, S, and O; and a 5- to 6-membered heteroaryl group having one or more heteroatoms chosen from N, S, and O; wherein the cyclic groups independently are optionally substituted with one or more substituents chosen from a halogen atom, a $C_{1-4}$ alkyl group, a $C_{1-4}$ alkoxy group, a carboxy group, a cyano group, a nitro group, a hydroxy group, an oxo group, a trifluoromethyl group, and a trifluoromethoxy group.

3. The compound according to claim 2, wherein k1, k2, s1, s2, l2, t1 and t2 are 0.

4. The compound according to claim 3, wherein $L_x$ is Formula (Lb1):

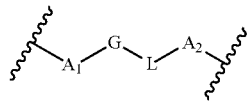

Formula (Lb1)

5. The compound according to claim 1, wherein Formula (B) is:

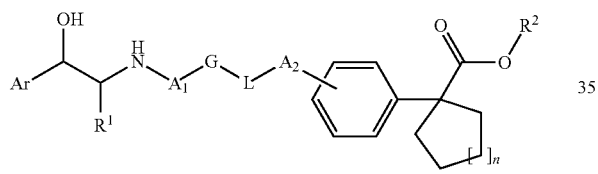

Formula (B)

and wherein:
Ar is chosen from a $C_{3-10}$ saturated or unsaturated, mono- or bicyclic cycloalkyl group, a $C_5$-$C_{14}$ mono- or bicyclic aryl group, a 3- to 14-membered saturated or unsaturated mono- or bicyclic heterocyclyl group having one or more heteroatoms selected from N, S, and O, a 5- to 14-membered mono- or bicyclic heteroaryl group having one or more heteroatoms chosen from N, S, and O; and wherein the cyclic groups independently are optionally substituted with one or more substituents chosen from a halogen atom, a cyano group, a nitro group, an oxo group, a carboxy group, a $C_{1-4}$ alkyl group, a $C_{1-4}$ alkoxy group, —$CF_3$, —$OCF_3$, —$NR^eR^f$, —$(CH_2)_p$—OH, —$NR^e(CO)R^f$, —$NR^e$—$SO_2$—$R^g$, —$SO_2NR^eR^f$, —$OC(O)R^h$ and —$NR^e(CH_2)_{(0-2)}$—$R^i$, wherein p is 0, 1 or 2, and wherein:
$R^e$ and $R^f$ are independently chosen from a hydrogen atom or a linear or branched $C_{1-4}$ alkyl group,
$R^g$ is chosen from a linear or branched $C_{1-4}$ alkyl group, a $C_{6-5}$ aryl group, a saturated or unsaturated $C_{3-8}$ cycloalkyl; wherein the cyclic groups independently are optionally substituted with one or more substituents chosen from a halogen atom, a $C_{1-4}$ alkyl group and a $C_{1-4}$ alkoxy group,
$R^h$ is chosen from a hydrogen atom, —$NR^eR^f$ and a $C_{5-6}$ aryl group, which is optionally substituted with one or more substituents chosen from a $C_{1-4}$ alkyl group and a $C_{1-4}$ alkoxy group,
$R^i$ is chosen from the group consisting of a $C_{5-6}$ aryl group, a $C_{3-8}$ cycloalkyl group and a 3 to 8 membered saturated or unsaturated heterocyclyl group, which groups independently are optionally substituted with one or more substituents chosen from a halogen atom, a $C_{1-4}$ alkyl group, and a $C_{1-4}$ alkoxy group,
$A_1$ and $A_2$ are independently chosen from a direct bond, a $C_{1-10}$ alkylene group, a $C_{2-10}$ alkenylene group and a $C_{2-10}$ alkynylene group, wherein said groups are optionally substituted with one or more substituents chosen from a halogen atom, a hydroxy group, a linear or branched $C_{1-4}$ alkyl group, a linear or branched $C_{1-4}$ alkoxy group, a $C_{5-6}$ aryl group, and a $C_{3-7}$ cycloalkyl group,
$R^1$ is chosen from a hydrogen atom, a linear or branched $C_{1-4}$ alkyl group, and a linear or branched $C_{1-4}$ alkoxy group,
$R^2$ is:

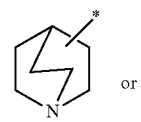

a)

or

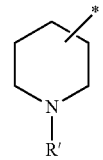

b)

wherein:
R' is chosen from a hydrogen atom or a linear or branched $C_{1-4}$ alkyl group,
\* is a point of attachment of $R^2$ to the remainder of the molecule of Formula (B),
L is chosen from a direct bond, —O—, —$NR^c$—, —S—, —S(O)—, —$SO_2$—, —$NR^c$(CO)—, —(CO) $NR^c$—, —$NR^c$(CO)($CH_2$)$_q$O—, —O($CH_2$)$_q$(CO) $NR^c$—, —O($CH_2$)$_q$(CO)O—, —O(CO)($CH_2$)$_q$O—, —$NR^c$($CH_2$)$_q$(CO)$NR^c$—, —$NR^c$(CO)($CH_2$)$_q$$NR^c$ (CO)—, —O($CH_2$)$_q$$NR^c$—, —$NR^c$($CH_2$)$_q$O—, —$NR^c$(CO)$NR^d$—, —C(O)—, —C(O)O—, —OC (O)—, —S(O)$_2$$NR^c$—, —$NR^c$S(O)$_2$—, —$NR^c$S(O)$_2$ $NR^d$—, —C(O)$NR^c$S(O)$_2$—, and —S(O)$_2$$NR^c$C (O)—, wherein $R^c$ and $R^d$ are independently chosen from a hydrogen atom and a linear or branched $C_{1-4}$ alkyl group and q is 0, 1, 2, 3 or 4,
G is chosen from a direct bond; a $C_{3-10}$ mono- or bicyclic cycloalkyl group; a $C_5$-$C_{14}$ mono- or bicyclic aryl group; a 3 to 14-membered saturated or unsaturated mono- or bicyclic heterocyclyl group having one or more heteroatoms chosen from N, S, and O; a 5- to 14-membered mono- or bicyclic heteroaryl group having one or more heteroatoms chosen from N, S, and O; and a bicyclic ring system comprising two monocyclic ring systems which are linked between each other by a covalent bond; wherein said monocyclic ring systems are independently chosen from a $C_{3-8}$ cycloalkyl group, a $C_{5-6}$ aryl group; a 3 to 8-membered saturated or unsaturated heterocyclyl group having one or more heteroatoms chosen from N, S, and O; and a 5- to 6-membered heteroaryl group having one or more heteroatoms chosen from N, S, and O; wherein the cyclic groups independently are optionally substituted with one or more substituents chosen from a halogen atom, a $C_{1-4}$ alkyl group, a $C_{1-4}$ alkoxy group, a carboxy group, a cyano group, a nitro group, a hydroxy group, an oxo group, a trifluoromethyl group, and a trifluoromethoxy group, and n is 0, 1, 2 or 3.

6. The compound according to claim 1, wherein Ar is formula (a), (b), (c), or (d):

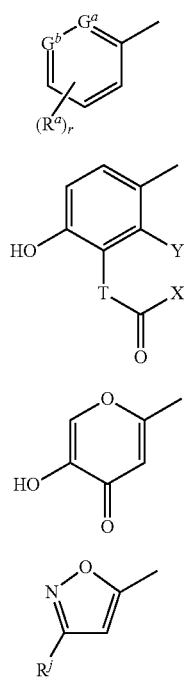

wherein
$G^a$ and $G^b$ are independently chosen from a nitrogen atom and a carbon atom,
r is 0, 1, 2 or 3 and
$R^a$ is chosen from a halogen atom, an amino group, a cyano group, a nitro group, an oxo group, a carboxy group, a $C_{1-4}$ alkyl group, a $C_{1-4}$ alkoxy group, —$CF_3$, —$OCF_3$, —$(CH_2)_p$—OH, —NH(CO)H, —NH—$SO_2$—$R^g$, —$SO_2NH_2$, —OC(O)H, —O(CO)—(4-methyl)phenyl, —O(CO)—N(CH_3)_2, —OC(O)NH_2, or —NH(CH_2)_{(1-2)}—$R^i$, wherein p is as defined above and $R^g$ and $R^i$ are independently chosen from a phenyl group optionally substituted with a one substituent chosen from a methyl group and a methoxy group,
$R^j$ is a halogen atom,
T is chosen from —$CH_2$— and —NH—,
Both X and Y are a hydrogen atom or X together with Y forms —$CH_2$—$CH_2$—, —CH═CH—, —$CH_2$—O—, or —S—, wherein in the case of —$CH_2$—O— the methylene group is bound to the carbonyl group holding X and the oxygen atom is bound to the carbon atom in the phenyl ring holding Y.

7. The compound according to claim 6, wherein Ar is formula (a) or (b) wherein:

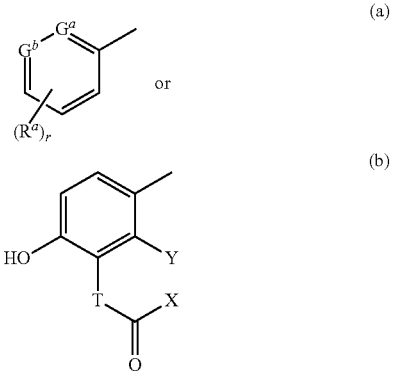

Both $G^a$ and $G^b$ are a carbon atom,
$R^a$ is chosen from halogen atom, amino group, cyano group, nitro group, —$(CH_2)_p$—OH, —NH(CO)H, —NH—$SO_2$—$CH_3$, —$SO_2NH_2$, —OC(O)H, —O(CO)-(4-methyl)phenyl, —O(CO)—N(CH_3)_2, —OC(O)NH_2, or —$CF_3$, wherein p is 0, 1 or 2,
T is —NH—,
Both X and Y are a hydrogen atom or X together with Y forms —CH═CH—, —$CH_2$—$CH_2$—, —$CH_2$—O—, or —S—, wherein in the case of —$CH_2$—O— the methylene group is bound to the carbon atom in the amido substituent holding X and the oxygen atom is bound to the carbon atom in the phenyl ring holding Y.

8. The compound according to claim 6, wherein Ar is chosen from 3-bromoisoxazol-5-yl, 3,4-dihydroxyl)henyl, 4-hydroxy-3-(methylsulfonamido)phenyl, 3,4-bis(4-methylbenzoyloxy)phenyl, 3,5-bis(dimethylcarbamoyloxy)phenyl, (5-hydroxy-6-hydroxymethyl)pyrid-2-yl, (4-amino-3,5-dichloro)phenyl, 4-hydroxyl)henyl, 4-hydroxy-3-(2-hydroxyethyl)phenyl, 4-hydroxy-3-(hydroxymethyl)phenyl, [4-amino-3-chloro-5-(trifluoromethyl)]phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl, 5-hydroxy-3-oxo-3,4-dihydro-2H-benzo[b][1,4]oxazin-8-yl and 4-hydroxy-2-oxo-2,3-dihydrobenzo[d]thiazol-7-yl.

9. The compound according to claim 7, wherein Ar is the compound of formula (b).

10. The compound according to claim 1, wherein Formula (I) is:

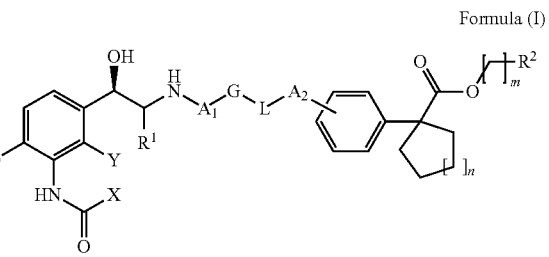

Formula (I)

wherein:
X and Y are both a hydrogen atom or X together with Y forms —CH═CH—, —$CH_2$—O—, or —S—, wherein in the case of —$CH_2$—O— the methylene group is bound to the carbon atom in the amido substituent holding X and the oxygen atom is bound to the carbon atom in the phenyl ring holding Y, $A_1$ and $A_2$ are independently chosen from a direct bond, a $C_{1-10}$ alkylene group, a $C_{2-10}$ alkenylene group, and a $C_{2-10}$ alkynylene group, wherein said groups are optionally substituted with one or more substituents chosen from a halogen atom, a hydroxy group, a linear or branched $C_{1-4}$ alkyl group, a linear or branched a $C_{1-4}$ alkoxy group, a $C_{5-6}$ aryl group, and a $C_{3-7}$ cycloalkyl group, G is chosen from a direct bond; a $C_{3-10}$ mono- or bicyclic cycloalkyl group; a $C_{5-14}$ mono- or bicyclic aryl group; a 3- to 14-membered saturated or unsaturated mono- or bicyclic heterocyclyl group having one or more heteroatoms chosen from N, S, and O; a 5- to 14-membered mono- or bicyclic heteroaryl group having one or more heteroatoms chosen from N, S, and O; and a bicyclic ring system consisting of two monocyclic ring systems which are linked between each other by a covalent bond wherein said monocyclic ring systems are independently chosen from a $C_{3-8}$ cycloalkyl group; a $C_{5-6}$ aryl group; a 3- to 8-membered saturated or unsaturated heterocyclyl group having one or more heteroatoms chosen from N, S, and O; and a 5- to 6-membered heteroaryl group having one or more heteroatoms chosen from N, S, and O; wherein the cyclic groups independently are optionally substituted with one or more substituents chosen from a halogen atom, a $C_{1-4}$ alkyl group, a $C_{1-4}$ alkoxy group, a carboxy, group, a cyano group, a nitro group, a hydroxy group, an oxo group, a trifluoromethyl group, and a trifluoromethoxy group, L is chosen from a direct bond, —O—, —NR$^c$—, —S—, —S(O)—, —SO$_2$—, —NR$^c$(CO)—, —(CO)NR$^c$—, —NR$^c$(CO)(CH$_2$)$_q$O—, —O(CH$_2$)$_q$(CO)NR$^c$—, —O(CH$_2$)$_q$(CO)O—, —O(CO)(CH$_2$)$_q$O—, —NR$^c$(CH$_2$)$_q$(CO)NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, —OC(O)—, —S(O)$_2$NR$^c$—, —NR$^c$S(O)$_2$—, —NR$^c$S(O)$_2$NR$^d$—, —C(O)NR$^c$S(O)$_2$—, or —S(O)$_2$NR$^c$C(O)—, wherein R$^c$ and R$^d$ are independently chosen from a hydrogen atom and a linear or branched C$_{1-4}$ alkyl group and q is 0, 1, 2, 3 or 4, n is 0, 1, 2 or 3, m is 0, 1 or 2, $R^2$ is a group of formula:

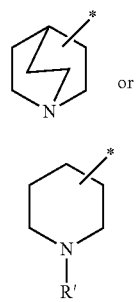

wherein:
R' is chosen from a hydrogen atom and a $C_{1-4}$ alkyl group, and
* is the point of attachment to the remainder of the molecule.

11. The compound according to claim 2, wherein $A_1$ and $A_2$ are independently chosen from $C_{1-6}$ alkylene group, $C_{2-6}$ alkenylene group, and $C_{2-6}$ alkynylene group, wherein said groups are optionally substituted with one or more substituents chosen from a halogen atom, a hydroxy group, a $C_{1-2}$ alkyl group, a $C_{1-2}$ alkoxy group, a $C_{5-6}$ aryl group, and a $C_{3-6}$ cycloalkyl group.

12. The compound according to claim 11, wherein $A_1$ and $A_2$ are independently a non-substituted $C_{1-4}$ alkylene group.

13. The compound according to claim 6, wherein X together with Y forms —CH=CH— or —CH$_2$—O—.

14. The compound according to claim 2, wherein L is chosen from a direct bond, —O—, —NR$^c$—, —S—, —S(O)—, —SO$_2$—, —NR$^c$(CO)—, —(CO)NR$^c$—, —NR$^c$(CO)(CH$_2$)$_q$O—, —O(CH$_2$)$_q$(CO)NR$^c$—, —O(CH$_2$)$_q$(CO)O—, —NR$^c$(CH$_2$)$_q$(CO)NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, —OC(O)—, —S(O)$_2$NR$^c$—, —NR$^c$S(O)$_2$—, —NR$^c$S(O)$_2$NR$^d$—, —C(O)NR$^c$S(O)$_2$—, or —S(O)$_2$NR$^c$C(O)—, wherein R$^c$ and R$^d$ are independently chosen from a hydrogen atom and a C$_{1-2}$ alkyl group and q is 0, 1, 2 or 3.

15. The compound according to claim 14, wherein L is chosen from a direct bond, —NR$^c$(CO)—, —(CO)NR$^c$—, —NR$^c$(CO)(CH$_2$)$_q$O—, —O(CH$_2$)$_q$(CO)NR$^c$—, or —C(O)O—, wherein R$^c$ is chosen from a hydrogen atom and a methyl group.

16. The compound according to claim 2, wherein G is chosen from a direct bond; a $C_{3-7}$ cycloalkyl group; a $C_{5-14}$ mono- or bicyclic aryl group; a 3- to 14-membered saturated or unsaturated mono- or bicyclic heterocyclyl group having one or more heteroatoms chosen from N, S, and O; a 5- to 14-membered mono- or bicyclic heteroaryl group having one or more heteroatoms chosen from N, S, and O; wherein the cyclic groups independently are optionally substituted with one or more substituents chosen from a halogen atom, a $C_{1-4}$ alkyl group, a $C_{1-4}$ alkoxy group, a carboxy, group, a cyano group, a nitro group, a hydroxy group, and an oxo group.

17. The compound according to claim 16, wherein G is a phenyl group substituted with two substituents chosen from a chlorine atom and methoxy group.

18. The compound according to claim 1, wherein R$^2$ is:

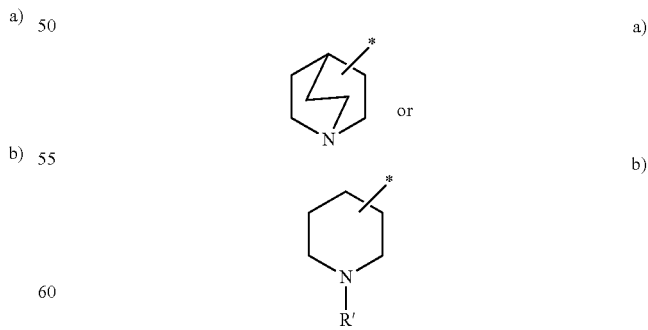

wherein R' is chosen from a hydrogen atom and a methyl group.

19. The compound according to claim 18, wherein R$^2$ is the quinuclidine derivative group of formula a):

wherein the asymmetric carbon atom of the quinuclidine ring to which the remaining molecule is attached is in the (R) Configuration.

20. The compound according to claim 6, wherein:
X together with Y form the group forms —CH=CH—,
$A_1$ and $A_2$ are independently a $C_{1-4}$ alkylene group,
G is a phenyl group substituted with two substituents chosen from a methoxy group and a chlorine atom,
L is chosen from —$NR^c(CO)$—, —$(CO)NR^c$—, —$O(CH_2)_q(CO)NR^c$— and —$C(O)O$—, and q is 1 or 2,
n is 2,
m is 0,
$R^2$ is the quinuclidine derivative group of formula a):

werein the asymmetric carbon atom of the quinuclidine ring to which the remaining molecule is attached is in (R) configuration.

21. The compound according to claim 1, wherein Formula (I) is:

Formula (I)

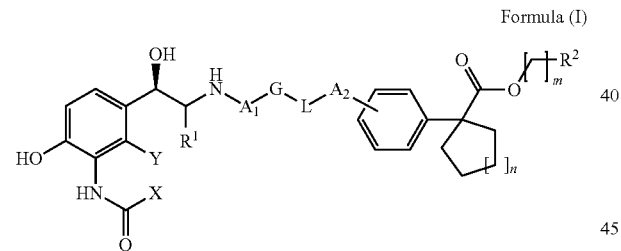

wherein:
X together with Y forms —CH=CH—,
$A_1$ and $A_2$ are independently a $C_{1-4}$ alkylene group,
$R^1$ is a hydrogen atom,
G is chosen from a direct bond; a cyclohexyl group; a phenyl group; a 6- to 10-membered saturated or unsaturated mono- or bicyclic heterocyclyl group having one or more heteroatoms chosen from N and O; a 5- to 10-membered mono- or bicyclic heteroaryl group having one or more heteroatoms chosen from N, S, and O; wherein the cyclic groups independently are optionally substituted with one or more substituents chosen from a chlorine atom, a methoxy group, a hydroxyl group, and an oxo group,
L is chosen from a direct bond, —O—, —$NR^c(CO)$—, —$(CO)NR^c$—, —$O(CH_2)_q(CO)NR^c$—, —$O(CH_2)_q(CO)O$—, —$NR^c(CH_2)_q(CO)NR^c$—, —$NR^c(CO)(CH_2)_qNR^c(CO)$—, —$C(O)$—, —$C(O)O$—,
wherein $R^c$ is chosen from a hydrogen atom and a methyl group and q is 0, 1 or 4, n is 1 or 2,
m is 0 or 1,
$R^2$ is:

a)

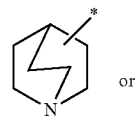 or b)

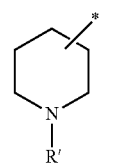

wherein:
R' represents a hydrogen atom and a methyl group, and
* is the point of attachment to the remainder of the molecule.

22. The compound according to claim 1 wherein Formula (Ia) is:

Formula (Ia)

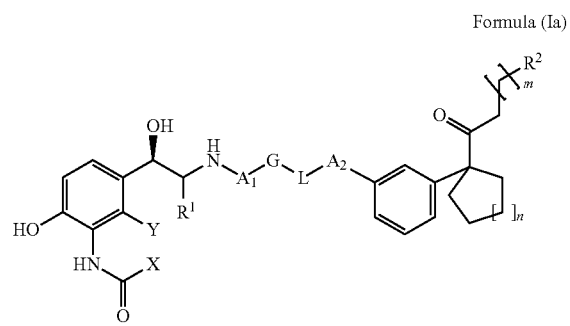

wherein:
X and Y are both a hydrogen atom or X together with Y forms —CH=CH—, —$CH_2$—O—, or —S—, wherein in the case of —$CH_2$—O— the methylene group is bound to the carbon atom in the amido substituent holding X and the oxygen atom is bound to the carbon atom in the phenyl ring holding Y,
$A_1$ and $A_2$ are independently a $C_{1-4}$ alkylene group,
$R^1$ is a hydrogen atom,
G is chosen from a direct bond; a cyclohexyl group; a phenyl group; a 6- to 10-membered saturated or unsaturated mono- or bicyclic heterocyclyl group having one or more heteroatoms chosen from N and O; a 5- to 10-membered mono- or bicyclic heteroaryl group having one or more heteroatoms chosen from N, S, and O; wherein the cyclic groups independently are optionally substituted with one or more substituents chosen from a chlorine atom, a methoxy group, a hydroxyl group, and an oxo group,
L is chosen from a direct bond, —O—, —$NR^c(CO)$—, —$(CO)NR^c$—, —$O(CH_2)_q(CO)NR^c$—, —$O(CH_2)_q(CO)O$—, —$NR^c(CH_2)_q(CO)NR^c$—, —$NR^c(CO)(CH_2)_qNR^c(CO)$—, —$C(O)$—, —$C(O)O$—, wherein R$^c$ is chosen from a hydrogen atom and a methyl group and q is 0, 1 or 4,
n is 1 or 2,
m is 0 or 1,
R$^2$ is:

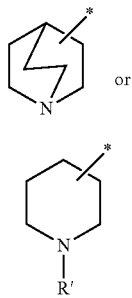

a) or b)

wherein:
R' represents a hydrogen atom and a methyl group, and
* is the point of attachment to the remainder of the molecule.

23. The compound according to claim 22, wherein X together with Y forms —CH=CH—.

24. The compound according to claim 1, wherein the compound is chosen from:
(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}phenyl)cyclohexanecarboxylate,
(3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxyl)henyl]amino}-4-oxobutyl)phenyl]cyclohexanecarboxylate,
(3R)-1-azabicyclo[2.2.2]oct-3-yl 1-[3-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)phenyl]cyclohexanecarboxylate,
(3R)-1-azabicyclo[2.2.2]oct-3-yl 1-(3-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]propyl}phenyl)cyclohexanecarboxylate,
(3R)-1-azabicyclo[2.2.2]oct-3-yl 1-(3-{4-[5-({[(2R)-2-hydroxy-2-(8-hydroxy-2-oxo-1,2-dihydroquinolin-5-yl)ethyl]amino}methyl)-1H-1,2,3-benzotriazol-1-yl]butyl}phenyl)cyclohexanecarboxylate,
(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxo-3,4-dihydroquinolin-1(2H)-yl]butyl}phenyl)cyclohexanecarboxylate,
(3R)-1-azabicyclo[2.2.2]oct-3-yl 1-(3-{4-[(5-{[(2R)-2-hydroxy-2-(8-hydroxy-2-oxo-1,2-dihydroquinolin-5-yl)ethyl]amino}pentyl)amino]-4-oxobutyl}phenyl)cyclohexanecarboxylate,
(3R)-1-azabicyclo[2.2.2]oct-3-yl 1-(3-{4-[6-({[(2R)-2-hydroxy-2-(8-hydroxy-2-oxo-1,2-dihydroquinolin-5-yl)ethyl]amino}methyl)-2-oxoquinolin-1(2H)-yl]butyl}phenyl)cyclohexanecarboxylate,
(3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)phenyl]cyclohexanecarboxylate,
(3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}oxy)propyl]phenyl}cyclohexanecarboxylate,
(3R)-1-azabicyclo[2.2.2]oct-3-yl 1-[3-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)phenyl]cyclohexanecarboxylate,
(3R)-1-azabicyclo[2.2.2]oct-3-yl 1-(3-{3-[[2-chloro-4-({[(2R)-2-hydroxy-2-(8-hydroxy-2-oxo-1,2-dihydroquinolin-5-yl)ethyl]amino}methyl)-5-methoxybenzoyl](methyl)amino]propyl}phenyl)cyclohexanecarboxylate,
3-[3-(1-{[(3R)-1-azabicyclo[2.2.2]oct-3-yloxy]carbonyl}cyclohexyl)phenyl]propyl 2-chloro-4-({[(2R)-2-hydroxy-2-(8-hydroxy-2-oxo-1,2-dihydroquinolin-5-yl)ethyl]amino}methyl)-5-methoxybenzoate,
(3R)-1-azabicyclo[2.2.2]oct-3-yl 1-(3-{[4-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}oxy)cyclohexyl]methyl}phenyl)cyclohexanecarboxylate,
3-[3-(1-{[(3R)-1-azabicyclo[2.2.2]oct-3-yloxy]carbonyl}cyclohexyl)phenyl]propyl 6-({[(2R)-2-hydroxy-2-(8-hydroxy-2-oxo-1,2-dihydroquinolin-5-yl)ethyl]amino}methyl)nicotinate,
(3R)-1-azabicyclo[2.2.2]oct-3-yl 1-(3-{4-[4-(2-{[(2R)-2-hydroxy-2-(8-hydroxy-2-oxo-1,2-dihydroquinolin-5-yl)ethyl]amino}ethyl)piperidin-1-yl]-4-oxobutyl}phenyl)cyclohexanecarboxylate,
(3R)-1-azabicyclo[2.2.2]oct-3-yl 1-(3-{4-(5-{[4-({[(2R)-2-hydroxy-2-(8-hydroxy-2-oxo-1,2-dihydroquinolin-5-yl)ethyl]amino}methyl)phenyl]amino}-5-oxopentyl)(methyl)amino]-4-oxobutyl}phenyl)cyclohexanecarboxylate,
1-azabicyclo[2.2.2]oct-4-ylmethyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate,
(3R)-1-azabicyclo[2.2.2]oct-3-yl 1-{3-[3-({[2-chloro-4-({[(2R)-2-hydroxy-2-(8-hydroxy-2-oxo-1,2-dihydroquinolin-5-yl)ethyl]amino}methyl)-5-methoxyphenoxy]acetyl}amino)propyl]phenyl}cyclohexanecarboxylate,
(3R)-1-azabicyclo[2.2.2]oct-3-yl 1-[3-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl)phenyl]cyclohexanecarboxylate,
(3R)-1-azabicyclo[2.2.2]oct-3-yl 1-{3-[4-({[6-({[(2R)-2-hydroxy-2-(8-hydroxy-2-oxo-1,2-dihydroquinolin-5-yl)ethyl]amino}methyl)pyridin-3-yl]carbonyl}amino)butyl]phenyl}cyclohexanecarboxylate,
4-[3-(1-{[(3R)-1-azabicyclo[2.2.2]oct-3-yloxy]carbonyl}cyclohexyl)phenyl]butyl 2-chloro-4-({[(2R)-2-hydroxy-2-(8-hydroxy-2-oxo-1,2-dihydroquinolin-5-yl)ethyl]amino}methyl)-5-methoxybenzoate,
(3R)-1-azabicyclo[2.2.2]oct-3-yl 1-(3-{4-[5-({[(2R)-2-hydroxy-2-(8-hydroxy-2-oxo-1,2-dihydroquinolin-5-yl)ethyl]amino}methyl)-1-oxo-1,3-dihydro-2H-isoindol-2-yl]butyl}phenyl)cyclohexanecarboxylate,
(3R)-1-azabicyclo[2.2.2]oct-3-yl 1-{3-[4-({[2-chloro-4-({[2-hydroxy-2-(8-hydroxy-2-oxo-1,2-dihydroquinolin-5-yl)ethyl]amino}methyl)-5-methoxyphenoxy]acetyl}amino)butyl]phenyl}cyclohexanecarboxylate,
(3R)-1-azabicyclo[2.2.2]oct-3-yl 1-{3-[3-({[6-({[(2R)-2-hydroxy-2-(8-hydroxy-2-oxo-1,2-dihydroquinolin-5- yl)ethyl]amino}methyl)pyridin-3-yl]carbonyl}amino)
propyl]phenyl}cyclohexanecarboxylate, (3R)-1-azabicyclo[2.2.2]oct-3-yl 1-(3-{4-[{[2-chloro-4-({[2-hydroxy-2-(8-hydroxy-2-oxo-1,2-dihydroquinolin-5-yl)ethyl]amino}methyl)-5-methoxyphenoxy]acetyl}(methyl)amino]butyl}phenyl)cyclohexanecarboxylate, (3R)-1-azabicyclo[2.2.2]oct-3-yl 1-[3-(4-{[5-({[(2R)-2-hydroxy-2-(8-hydroxy-2-oxo-1,2-dihydroquinolin-5-yl)ethyl]amino}methyl)-1,3-thiazol-2-yl]amino}-4-oxobutyl)phenyl]cyclohexanecarboxylate, piperidin-4-ylmethyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate, (1-methylpiperidin-4-yl)methyl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate, (3R)-1-azabicyclo[2.2.2]oct-3-yl 1-{3-[3-({N-[2-chloro-4-({[(2R)-2-hydroxy-2-(8-hydroxy-2-oxo-1,2-dihydroquinolin-5-yl)ethyl]amino}methyl)-5-methoxyphenyl]glycyl}amino)propyl]phenyl}cyclohexanecarboxylate, (3R)-1-azabicyclo[2.2.2]oct-3-yl 1-[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclohexanecarboxylate, and (3R)-1-azabicyclo[2.2.2]oct-3-yl 1-[3-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)phenyl]cyclopentanecarboxylate, or a pharmaceutically acceptable salt, or N-oxide, or isotopically-labeled derivate thereof.

25. A pharmaceutical composition comprising a compound according to claim 1 and a pharmaceutically acceptable diluent or carrier.

26. A method for treating a subject afflicted with a pathological condition or disease, wherein the pathological condition or disease is asthma and/or COPD, the method comprising administering to said subject an effective amount of a compound according to claim 1.

* * * * *

UNITED STATES PATENT AND TRADEMARK OFFICE
CERTIFICATE OF CORRECTION

PATENT NO. : 10,005,771 B2
APPLICATION NO. : 15/514294
DATED : June 26, 2018
INVENTOR(S) : Carlos Puig Duran et al.

It is certified that error appears in the above-identified patent and that said Letters Patent is hereby corrected as shown below:

In the Claims

Claim 8, Column 114, Line 32, "3,4-dihydroxyl)henyl" should read --3,4-dihydroxyphenyl--.

Claim 8, Column 114, Line 36, "4-hydroxyl)henyl" should read --4-hydroxyphenyl--.

Claim 24, Column 119, Line 37, "5-methoxyl)henyl]" should read --5-methoxyphenyl]--.

Signed and Sealed this
Eighteenth Day of September, 2018

Andrei Iancu
*Director of the United States Patent and Trademark Office*